(12) United States Patent
Gong et al.

(10) Patent No.: US 7,601,342 B2
(45) Date of Patent: *Oct. 13, 2009

(54) CELL FUSIONS AND METHODS OF MAKING AND USING THE SAME

(75) Inventors: Jianlin Gong, Brookline, MA (US); Donald Kufe, Wellesley, MA (US)

(73) Assignee: Dana Farber Cancer Institute, Boston, MA (US)

( * ) Notice: Subject to any disclaimer, the term of this patent is extended or adjusted under 35 U.S.C. 154(b) by 14 days.

This patent is subject to a terminal disclaimer.

(21) Appl. No.: 11/657,882

(22) Filed: Jan. 24, 2007

(65) Prior Publication Data

US 2007/0141704 A1    Jun. 21, 2007

Related U.S. Application Data

(63) Continuation of application No. 11/053,321, filed on Feb. 7, 2005, now abandoned, which is a continuation of application No. 09/782,492, filed on Feb. 12, 2001, now abandoned, which is a continuation-in-part of application No. 09/618,917, filed on Jul. 18, 2000, now Pat. No. 6,652,848, which is a continuation of application No. 09/060,603, filed on Apr. 15, 1998, now abandoned, application No. 11/657,882, which is a continuation-in-part of application No. 09/642,701, filed on Aug. 12, 2000, now abandoned, which is a continuation of application No. PCT/US99/01464, filed on Jan. 25, 1999, now abandoned.

(60) Provisional application No. 60/043,609, filed on Apr. 15, 1997, provisional application No. 60/088,357, filed on Jan. 26, 1998, provisional application No. 60/080,041, filed on Mar. 31, 1998, provisional application No. 60/181,822, filed on Feb. 11, 2000, provisional application No. 60/184,687, filed on Feb. 24, 2000.

(51) Int. Cl.
  *A01N 63/00* (2006.01)
  *C12N 5/00* (2006.01)

(52) U.S. Cl. .................. 424/93.2; 424/93.1; 424/93.7; 435/346; 435/347; 435/363; 435/365.1

(58) Field of Classification Search .................. None
See application file for complete search history.

(56) References Cited

U.S. PATENT DOCUMENTS

| | | | |
|---|---|---|---|
| 5,348,878 A | 9/1994 | Rock | 435/240.26 |
| 5,851,756 A | 12/1998 | Steinman et al. | 435/2 |
| 6,156,307 A | 12/2000 | Granucci | 424/93.21 |
| 6,306,388 B1 | 10/2001 | Nair et al. | 424/93.21 |
| 6,387,701 B1 | 5/2002 | Nair et al. | 435/455 |
| 6,652,848 B1 * | 11/2003 | Gong et al. | 424/93.1 |
| 6,670,186 B1 | 12/2003 | Nair et al. | 435/455 |

FOREIGN PATENT DOCUMENTS

| | | |
|---|---|---|
| WO | WO 93/20185 | 10/1993 |
| WO | WO 94/02156 | 2/1994 |
| WO | WO 94/28113 | 12/1994 |
| WO | WO 95/16775 | 6/1995 |
| WO | WO 96/07733 | 3/1996 |
| WO | WO 96/30030 | 10/1996 |
| WO | WO 98/17300 | 4/1998 |
| WO | WO 98/46785 | 10/1998 |
| WO | WO 00/57705 | 10/2000 |

OTHER PUBLICATIONS

Albert et al., *Nature*, 392:86-89 (1998).
Albert et al., *J. Exp. Med.*, 188(7):1359-1368 (1998).
Altenschmidt et al., *J. Immunol.*, 159:5509-5515 (1997).
Austyn, *Antigen-Presenting Cells*, IRL Press, New York, pp. 28-45 (1990).
Bakker et al., *Cancer Res.*, 55:5530-5534 (1995).
Banchereau et al., *Nature*, 392:246-252 (1998).
Bhardwaj et al., *J. Exp. Med.*, 175:267-273 (1992).
Bodey et al., "Failure of Cancer Vaccines: The Significant Limitations of this Approach to Immunotherapy", pp. 2665-2676 (2000).
Cao et al., *Immunol.*, 97:616-625 (1999).
Carbone et al., *Fundamental Immunology*, Second Edition, ed. by William E. Paul, Raven Press Ltd., New York, pp. 541-567 (1989).
Celluzzi et al., *J. Investig. Dermatol.*, Abstract No. 157, 108: 564 (1997).
Celluzzi et al., *J. Immunol.*, 160:3081-3085 (1998).
Chen et al., *Proc. Am. Assoc. Cancer Res.*, Abstract No. 72, 38:11 (1997).
Cohen et al., *J. Exp. Med.*, 154:1881-1898 (1981).

(Continued)

*Primary Examiner*—Q. Janice Li
(74) *Attorney, Agent, or Firm*—Mintz, Levin, Cohn, Ferris, Glovsky and Popeo PC; Ivor R. Elrifi; Christina K. Stock

(57) ABSTRACT

The invention is concerned with fusions of dendritic cells and antigen presenting cells. Also provided are methods of making and using these cell fusions, including methods of adoptive immunotherapy. The fusions according to the invention can also be used in methods for antigen discovery.

16 Claims, 15 Drawing Sheets

OTHER PUBLICATIONS

Delaney et al., *Therapeutic Immunol.*, 1:153-164 (1994).
Dunnion et al., *Eur. J. Immunol.*, 25(1):58 (1998).
Fahey et al., *Clin. Exp. Immunol.*, 88:1-5 (1992).
Fisher et al., *J. Immunol.*, 130:2666-2670 (1993).
Freeman et al., *Science*, 262:909-911 (1993).
Freudenthal et al., Proc. *Natl. Acad. Sci. USA*, 87:7698-7702 (1990).
Gimmi et al., *Nat. Med.*, 2:1367-1370 (1996).
Gong et al., *Proc. Am. Assoc. Cancer Res.*, Abstract No. 1797, 39:263 (1988).
Gong et al., *Gene Therapy*, 4:1023-1028 (1997).
Gong et al., *Proc. Am. Assoc. Cancer Res.*, Abstract No. 4137, 38:616 (1997).
Gong et al., *Proc. Am. Assoc. Cancer Res.*, Abstract No. 1777, 39:172 (1998).
Gong et al., *Nat. Med.*, 3:558-561 (1997).
Gong et al., *Proc. Natl. Acad. Sci. USA*, 95:6279-6283 (1998).
Gong et al., *J. Immunol.*, 165:1705-1711 (2000).
Gong et al., *Proc. Natl. Acad. Sci. USA*, 97:2715-2718 (2000).
Grabbe et al., *J. Immunol.*, 146:3656-3661 (1991).
Guo et al., *Science*, 263:518-520 (1994).
Houghton et al., *Nat. Med.*, 4:270-271 (1998).
Hsu et al., *Nat. Med.*, 2:52-58 (1996).
Hural et al., *J. Immunol.*, 169:557-565 (2002).
Inaba et al., *J. Exp. Med.*, 175:1157-1167 (1992).
Inaba et al., *J. Exp. Med.*, 176:1693-1702 (1992).
Inoue et al., *Cancer Res.*, 56:4702-4708 (1996).
Janeway Jr., *Immunol.* (2001).
Kawashima et al., *Int. J. Cancer*, 78:518-524 (1998).
Kikuchi et al., *Cancer Immunol. Immunother.*, 50:337-344 (2001).
Knight et al., *Proc. Natl. Acad. Sci. USA*, 82:4495-4497 (1985).
Komatsubara et al., *Microbiol. Immunol.*, 32:869-875 (1988).
Krause, *J. Immunol.*, 25:421-428 (2002).
Ladyman et al., *Monoclonal Antibodies: Production, Engineering and Clinical Application*, eds. Ritter and Ladyman, pp. 9, 15-17.
Lespagnard et al., *Int. J. Cancer*, 76:250-258 (1998).
Mayordomo et al., *Nat. Med.*, 1:1297-1302 (1995).

Moingeon et al., *Challenges and Issues in New Vaccine Development*, 23(4):173-175 (2002).
Mukherji et al., *Proc. Natl. Acad. Sci USA*, 92:8078-8082 (1995).
Nabavi et al., *Nature*, 360:266-268 (1992).
Ohnishi et al., *Immunol. Cell. Biol.*, 73:205-211 (1995).
Orscheschek et al., *Eur. J. Immunol.*, 24:2682-2690 (1994).
Paglia et al., *J. Exp. Med.*, 178:1893-1901 (1993).
Parkhurst et al., *J. Immunol.*, 170:5317-5325 (2003).
Powell et al., *J. Immunother. Emphasis Tumor Immunol.*, 17:209-221 (1995).
Radoja et al., "Cancer-Induced Defective Cytotoxic T Lymphocyte Effector Function: Another Mechanism how Antigenic Tumors Escape Immune-Mediated Killing", pp. 465-479 (2000).
Riddell et al., *Rev. Med. Virol.*, 7:181-192 (1997).
Romani et al., *J. Inv. Dermatol.*, 93:600-609 (1989).
Romani et al., *J. Exp. Med.*, 180:83-93 (1994).
Rosenberg et al., *Nat. Med.*, 4:321-327 (1998).
Rosenzwajg et al., *Blood*, 87:535-544 (1996).
Sallusto et al., *J. Exp. Med.*, 179:1109-1118 (1994).
Schiltz et al., *J. Immunother.*, 20:377-386 (1997).
Schuler et al., *J. Exp. Med.*, 161:526-546 (1985).
Steinman et al., *J. Exp. Med.*, 149:1-16 (1979).
Thomas et al., *J. Immunol.*, pp. 4016-4028 (1994).
Tsai et al., *J. Immunol.*, 158:1796-1802 (1997).
Wang et al., *J. Immunol.*, 161:5516-5524 (1998).
Yeh et al., *J. Invest. Dermatol.* 109:728-733 (1997).
Young et al., *J. Clin. Invest.*, 90:29-237 (1992).
Zitvogel et al., *J. Exp. Med.*, 183:87-97 (1996).
Peters, *Immunol.*, vol. 159(1/2), 14th International Leucocyte Conference, Heidelberg (1981).
Somasse et al., *Advances Exper. Med. Biol.*, 329:299-303 (1993).
Mannering et al., "HLA-DR1-restricted bcr-abl (b3a2)-specific CD4+ T lymphocytes respond to dendritic cells pulsed with b3a2 peptide and antigen-presenting cells exposed to b3a2 containing cell lysates", *Blood*, 90(1):290-297 (1997).

\* cited by examiner

CELL FUSIONS AND METHODS OF MAKING AND USING THE SAME

RELATED APPLICATIONS

This application is a continuation of U.S. Ser. No. 11/053,321, filed on Feb. 7, 2005 now abandoned, which is a continuation of U.S. Ser. No. 09/782,492, filed on Feb. 12, 2001 now abandoned, which is a continuation-in-part of U.S. Ser. No. 09/618,917, filed on Jul. 18, 2000 (now U.S. Pat. No. 6,652,848), which is a continuation of U.S. Ser. No. 09/060,603 (now abandoned), filed on Apr. 15, 1998, which in turn claims priority to provisional application U.S. Ser. No. 60/043,609 (now abandoned) filed on Apr. 15, 1997. This application also claims priority to provisional applications U.S. Ser. No. 60/181,822, filed on Feb. 11, 2000 (now abandoned), and U.S. Ser. No. 60/184,687, filed on Feb. 24, 2000 (now abandoned). This application is also a continuation-in-part of U.S. Ser. No. 09/642,701, filed Aug. 12, 2000 (now abandoned), which is a continuation of PCT/US99/01464 (now abandoned), filed Jan. 25, 1999, which in turn claims priority to provisional applications U.S. Ser. No. 60/088,357, filed on Jan. 26, 1998 (now abandoned), and U.S. Ser. No. 60/080,041, filed on Mar. 31, 1998 (now abandoned). Each of these is herein incorporated by reference in its entirety.

FIELD OF THE INVENTION

The invention relates to cellular immunology.

BACKGROUND OF THE INVENTION

Dendritic cells ("DC"s) are potent antigen-presenting cells ("APC"s) in the immune system. It has been shown that DCs provide all the signals required for T cell activation and proliferation. These signals can be categorized into two types. The first type, which gives specificity to the immune response, is mediated through interaction between the T-cell receptor/CD3 ("TCR/CD3") complex and an antigenic peptide presented by a major histocompatiblity complex ("MHC") class I or II protein on the surface of APCs. This interaction is necessary, but not sufficient, for T cell activation to occur. In fact, without the second type of signals, the first type of signals can result in T cell anergy. The second type of signals, call costimulatory signals, is neither antigen-specific nor MHC-restricted, and can lead to a full proliferation response of T cells and induction of T cell effector functions in the presence of the first type of signals.

Costimulatory signals are generated by interaction between receptor-ligand pairs expressed on the surface of APCs and T cells. One exemplary receptor-ligand pair is one of the B7 costimulatory molecules on the surface of DCs and its counter-receptor CD28 or CTLA-4 on T cells (Freeman et al., Science 262:909-11 (1993); Young et al., J. Clin. Invest. 90:229 (1992); Nabavi et al., Nature 360:266 (1992)).

DCs are minor constituents of various immune organs such as spleen, thymus, lymph node, epidermis, and peripheral blood. For instance, DCs represent merely about 1% of crude spleen (Steinman et al., J. Exp. Med. 149:1 (1979) or epidermal cell suspensions (Schuler et al., J. Exp. Med. 161:526 (1985); and Romani et al., J. Invest. Dermatol. 93:600 (1989)), and 0.1-1% of mononuclear cells in peripheral blood (Freudenthal et al., Proc. Natl. Acad. Sci. USA 87:7698 (1990)). Methods for generating dendritic cells from peripheral blood or bone marrow progenitors have been described (Inaba et al., J. Exp. Med. 175:1157 (1992); Inaba et al., J. Exp. Med. 176:1693-1702 (1992); Romani et al., J. Exp. Med. 180:83-93 (1994); and Sallusto et al., J. Exp. Med. 179:1109-1118 (1994)).

SUMMARY OF THE INVENTION

The invention features compositions for stimulating an immune system. Accordingly, the invention includes a hybrid cell (or progeny thereof), which is a fusion product of a dendritic cell, e.g., a non-follicular dendritic cell, and non-dendritic cell. The hybrid cell expresses B7 on its surface. Preferably, the hybrid cell also expresses other costimulatory molecules, MHC class I and class II molecules, and adhesion molecules Preferably, the dendritic cell fusion partner and the non-dendritic cell are derived from the same species. Examples include hybrid cells in which the non-dendritic cell fusion partner expresses a disease-associated antigen such as that derived from a tumor, a bacterium, or a virus. Alternatively, the non-dendritic cell is a tumor cell. The dendritic cell is autologous or allogeneic. The dendritic cell and the non-dendritic cell are preferably derived from the same individual, e.g., a human patient. A hybrid cell is a cell that contains cytoplasmic, membrane, or nuclear components from two or more cells. The dendritic cells are derived from a variety of tissues, e.g., myeloid or lymphoid tissue, and may be used at an early or late stage of maturity.

These compositions each contain a plurality of cells which contain fused cells, each of which fused cells is generated by fusion between at least one mammalian dendritic cell (e.g., a DC derived from a bone marrow culture or a peripheral blood cell culture) and at least one mammalian non-dendritic cell (e.g., a cancer cell or a transfected cell) that expresses a cell-surface antigen (e.g., a cancer antigen). By "cancer antigen" is meant an antigenic molecule that is expressed primarily or entirely by cancer cells, as opposed to normal cells in an individual bearing the cancer. The fused cells in the compositions express, in an amount effective to stimulate an immune system (e.g., to activate T cells), MHC class II molecules, B7, and the cell-surface antigen. By "B7" is meant any member (e.g., B7-1 or B7-2) of the B7 family of costimulatory molecules.

The parental cells used to generate the fused cells can be obtained from a single individual (e.g., a human, a mouse, or a rat). They can also be obtained from different individuals of the same species (e.g., *homo sapiens*), with matching or non-matching MHC molecules.

Also embraced by the invention are methods of producing fused cells. A method of making a hybrid cell, include the steps of contacting dendritic cell with a non-dendritic cell under a condition which allows formation of a fusion product. The fusion product is a hybrid cell expressing B7 on its surface. The method may also contain the step of contacting the hybrid cell with a second dendritic cell under conditions, which allow formation of a second fusion product. The second fusion product is a composite dendritic cell expressing B7 on its surface. In these methods, mammalian dendritic cells are fused with mammalian non-dendritic cells expressing a cell-surface antigen in the presence of a fusion agent (e.g., polyethylene glycol, electricity, or Sendai virus). After optionally culturing the post-fusion cell mixture in a medium (which optionally contains hypoxanthine, aminoptem, and thymidine) for a period of time, the cultured fused cells are separated from unfused parental non-dendritic cells, based on the different adherence properties of the two cell groups. For example, the fused cells are used directly after the dendritic and non-dendritic cells are joined or after one or more hours of in vitro culture. The unfused parental dendritic cells do not proliferate, and so die off. Even if they remain present in the therapeutic composition, they will not interfere with the effects of the fused cells. The isolated fused cells, which typically express (a) MHC class II protein, (b) B7, and (c) the cell-surface antigen on the non-dendritic parental cells, are useful for stimulating an immune system.

The invention also provides methods of maintaining the DC phenotype of a fused cell by re-fusing it one or more times with at least one additional mammalian dendritic cell. The re-fused cells express MHC class II molecules, B7, and the cell-surface antigen of the dendritic parental cells, and are useful for stimulating an immune system.

The compositions of the invention can be administered to an individual (e.g., a human) to stimulate the individual's immune system. This individual may need an immune stimulation due to infection, or susceptibility to infection, with an intracellular pathogen; cancer; or predisposition to develop cancer. The DCs used to generate fused cells can be obtained from this individual. If this individual has cancer, the individual's own cancer cells can be used for fusion with his or her own DCs to generate fused cells, which are then administered to the individual.

This invention provides a substantially pure population of educated, antigen-specific immune effector cells expanded in culture at the expense of hybrid cells, wherein the hybrid cells are antigen presenting cells (APCs) fused to cells that express one or more antigens.

Also provided by this invention is a method of producing antigen-specific immune effector cells, methods of adoptive immunotherapies and a method of identifying a gene encoding an antigen specifically recognized by the immune effector cells.

The invention also includes a population of activated immune effector cells. For example, the cells are activated ex vivo. The population contains a T cell and a hybrid cell. A substantially pure population of activated, antigen-specific immune effector cells is also within the invention. The cells are derived from a coculture of a patient-derived immune cell and a hybrid cell. Effector cells specifically kill autologous tumor cells. Effector cells generated as described above recognize a known or unknown tumor antigen and can therefore be used to identify unknown tumor antigens.

A method for producing an antigen-specific immune effector cell is carried out by contacting a T cell with the hybrid cell described above. The T cell is derived from a variety of sources such as peripheral blood or from a tumor site. The contacting step occurs in vivo or ex vivo. For example, a method for producing a population of activated immune effector cells specific for a target antigen is carried out by contacting a T cell with a hybrid cell for a period of time sufficient to activate said T cell and removing the hybrid cell from said T cell to yield a population of antigen-specific immune effector cells. Optionally, the population of effector cells is purified from other cells with which they naturally-occur or with which they were cultured Also within the invention is a vaccine, which contains a hybrid cell and a pharmaceutically acceptable carrier. Alternatively, the vaccine composition contains an activated antigen-specific effector cell, e.g., an effector cell, which is derived from a coculture of a patient-derived immune cell such as a T cell and a hybrid antigen presenting cell.

The invention also involves an instraspecies hybrid of a dendritic and a non-dendritic cell. This hybrid expresses known and unknown cell antigens from the non-dendritic cells, MHC class I and II molecules, and a B7 costimulatory molecule in an amount effective to stimulate a cytotoxic immune response against the non-dendritic cell antigens.

The invention also provides a method of making a population of cells comprising activated T cells comprising providing a plurality of cells, at least half of which are fused cells generated by fusion between at least one mammalian non-dendritic cells that expresses a cell-surface antigen. In this method, at least half of the fused cells express, in an amount effective to stimulate an immune response, a MHC class II molecule, B7, and the cell-surface antigen. A population of T cells is then contacted with this plurality of cells, which causes the activation of the T cells.

Unless otherwise defined, all technical and scientific terms used herein have the same meaning as commonly understood by one of ordinary skill in the art to which this invention belongs. All citations herein are incorporated by reference in their entirety.

Other features and advantages of the invention will be apparent from the following drawings, detailed description, and from the claims.

DETAILED DESCRIPTION OF THE INVENTION

Figure 1A:
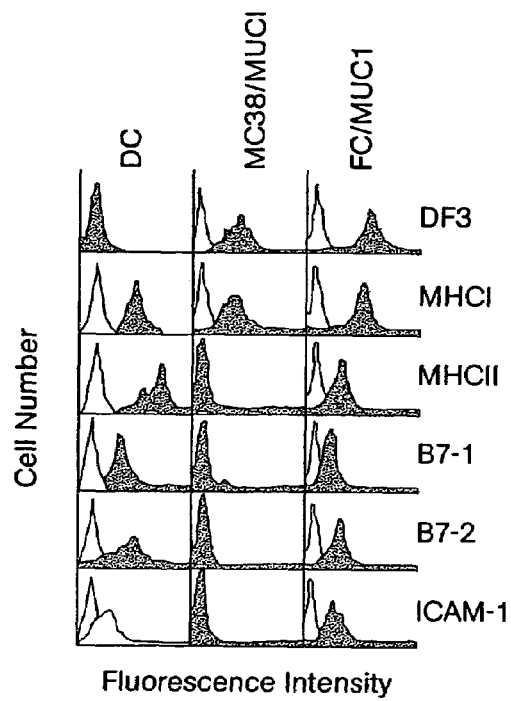
FIG. 1A is a graph showing the results of flow cytometric analysis of the indicated antigens on the surface of DCs (DC), MC38 cells (MC38/MUC1) and fused cells generated by fusion between DC's and MC38/MUC1 cells (FC/MUC1).
Figure 1B:
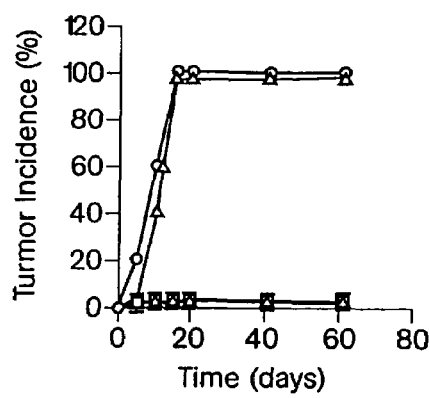
FIG. 1B is a graph showing tumor incidence in female C57BL/6 mice (10 per group) injected subcutaneously with $2 \times 10^5$ MC38/MUC1 cells (open triangle), $2 \times 10^6$ DCs mixed with $2 \times 10^5$ MC38/MUC1 cells (open circle), $2 \times 10^5$ FC/MUC1 cells (shaded circle), or $5 \times 10^5$ FC/MUC1 cells (shaded box). Tumor incidence (>3 mm in diameter) was monitored at the indicated days after injection. Similar results were obtained in three separate experiments.
Figure 1C:
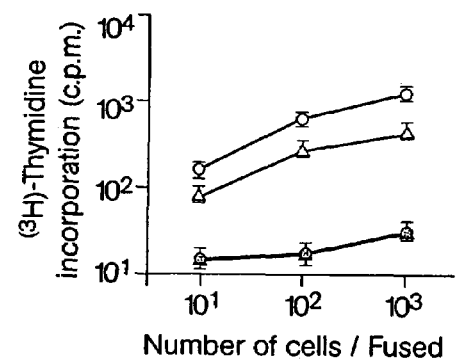
FIG. 1C is a graph showing [$^3$H]-thymidine incorporation in mixed leukocyte reactions. DCs (open circle), MC38/MUC1 cells (shaded circle), and FC/MUC1 cells (open triangle) were irradiated (30 Gy) and added at the indicated ratios to $1 \times 10^5$ allogeneic Balb/c T cells. [$^3$H]-Thymidine uptake at 6 h of incubation is expressed as the mean±s.e.m. of three determinations. Similar results were obtained in three separate experiments.
Figure 2A:
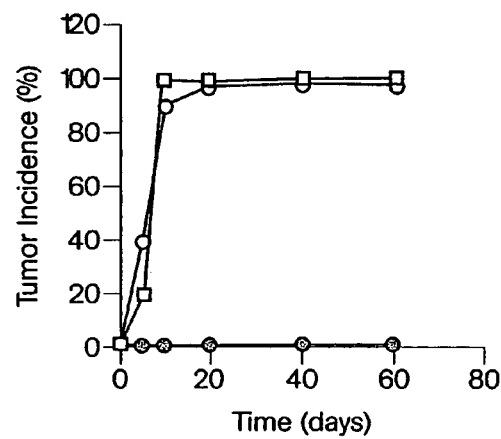
FIG. 2A is a graph showing induction of anti-tumor activity by FC/MUC1 in the form of percent tumor incidence. Groups of 10 mice were injected subcutaneously twice at 14-day intervals $3 \times 10^5$ DC (open circle), $3 \times 10^5$ FC/MUC1 (shaded circle), or PBS (open box). After 14 days, the mice were challenged subcutaneously with $2.5 \times 10^5$ MC38/MUC1 cells. Tumors >3 mm in diameter were scored as positive. Similar results were obtained in three separate experiments.
Figure 2B:
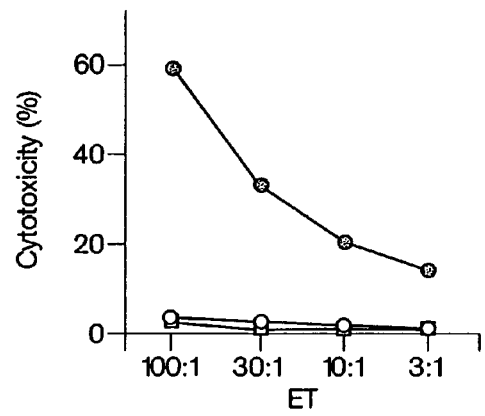
FIG. 2B is a graph showing induction of anti-tumor activity by FC/MUC1 in the form of cytotoxicity. Mice injected twice with DC (open circle), FC/MUC1 (shaded circle) or PBS (open box) were challenged with $2.5 \times 10^5$ MC38/MUC1 tumor cells. Splenocytes were isolated at 20 days after challenge and incubated at the indicated effector:target ratios with MC38/MUC1 target cells. Cytotoxic T lymphocyte ("CTL") activity (mean±s.e.m.) was determined by the 4-h LDH release assay. Similar results were obtained in three separate experiments.
Figure 2C:
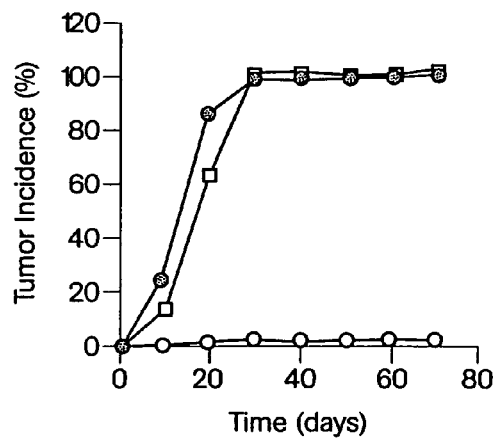
FIG. 2C is a graph showing induction of anti-tumor activity by FC/MUC1 in the form of percent tumor incidence. Mice (8 per group) were injected intravenously and intraperitoneally every other day with mAbs against CD4$^+$ (open box) and CD8$^+$ (shaded circle) cells beginning 4 days before the first of two immunizations with FC/MUC1 and continuing until 4 days before challenge with $5 \times 10^5$ MC38/MUC1 cells. Rat IgG (open circle) was injected as a control. Tumors of >3 mm were scored as positive. Similar results were obtained in two separate experiments.
Figure 2D:
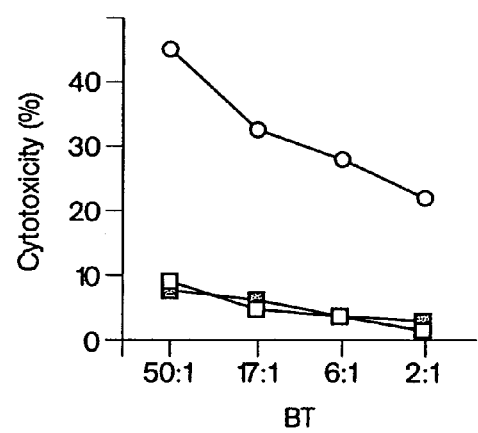
FIG. 2D is a line graph showing induction of anti-tumor activity by FC/MUC1 in the form of cytotoxicity. Mice were treated as above with mAbs against CD4$^+$ (open box) and CD8$^+$ (shaded circle), or rat IG (open circle), immunized with FC/MUC1 and then challenged with MC38/MUC1 cells. Splenocytes were harvested at 20 days after tumor challenge and incubated with MC38/MUC1 cells. CTL activity (mean±s.e.m.) was determined by the 4-h LDH release assay. Similar results were obtained in three separate experiments.
Figure 3A:
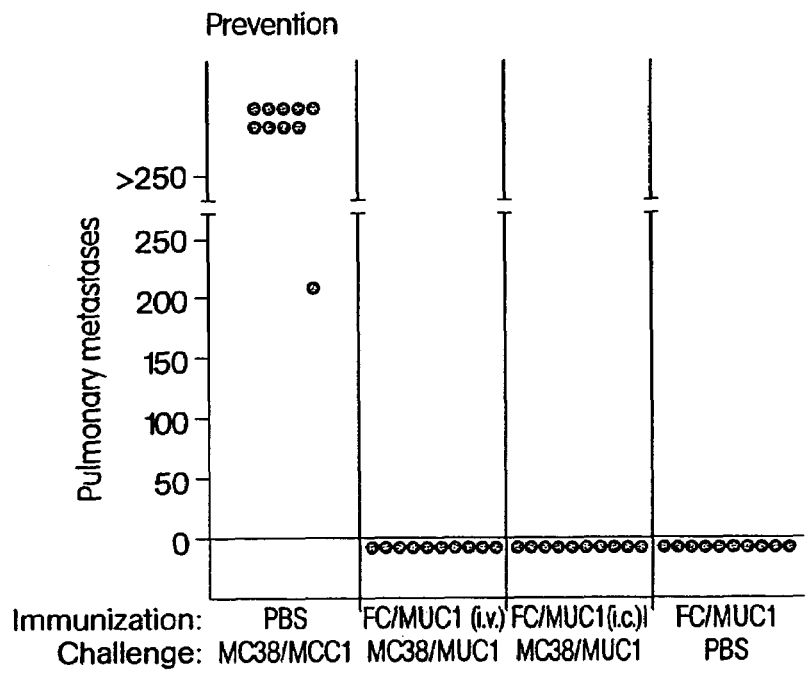
FIG. 3A is a graph showing prevention of MC38/MUC1 pulmonary metastases after immunization with FC/MUC1. Groups of 10 mice were injected twice with FC/MUC1 cells or PBS and then challenged after 14 days with intravenous administration of 1×10$^6$ MC38/MUC1 cells. The mice were sacrificed 28 days after challenge. Pulmonary metastases were enumerated after staining the lungs with India ink (Wexler, J. Natl. Cancer Inst. 36: 641-643, 1966).
Figure 3B:
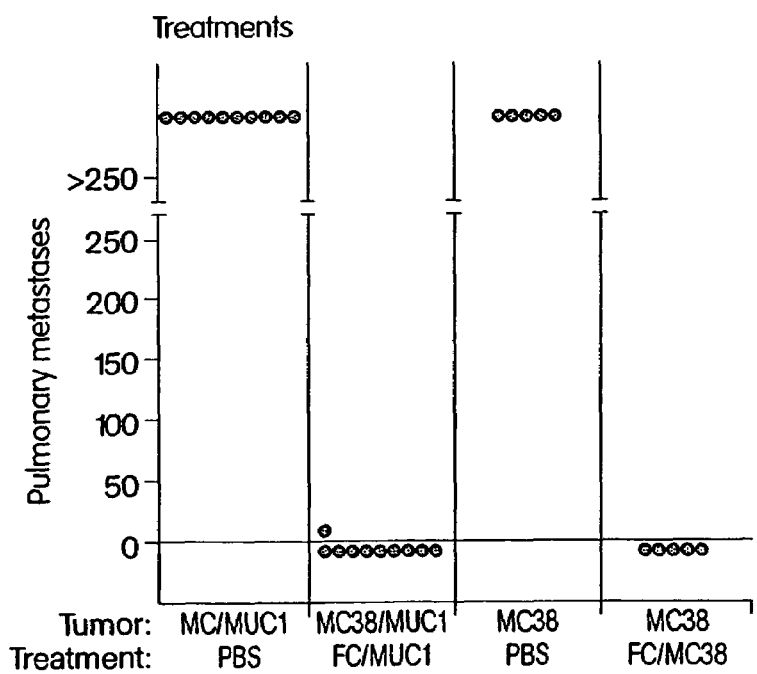
FIG. 3B is a graph showing treatment of MC38/MUC1 pulmonary metastases after immunization with FC/MUC1. Groups of 10 mice were injected intravenously with 1×10$^6$ MC38/MUC1 cells or MC38 cells. The mice were immunized with 1×10$^6$ FC/MUC1 or FC/MC38 at 4 and 18 days after tumor challenge and then sacrificed after an additional 10 days. Pulmonary metastases were enumerated for each mouse. Similar results were obtained in two separate experiments (10/10 mice treated with FC/MUC1 had no pulmonary metastases in the second experiment).
Figure 4A:
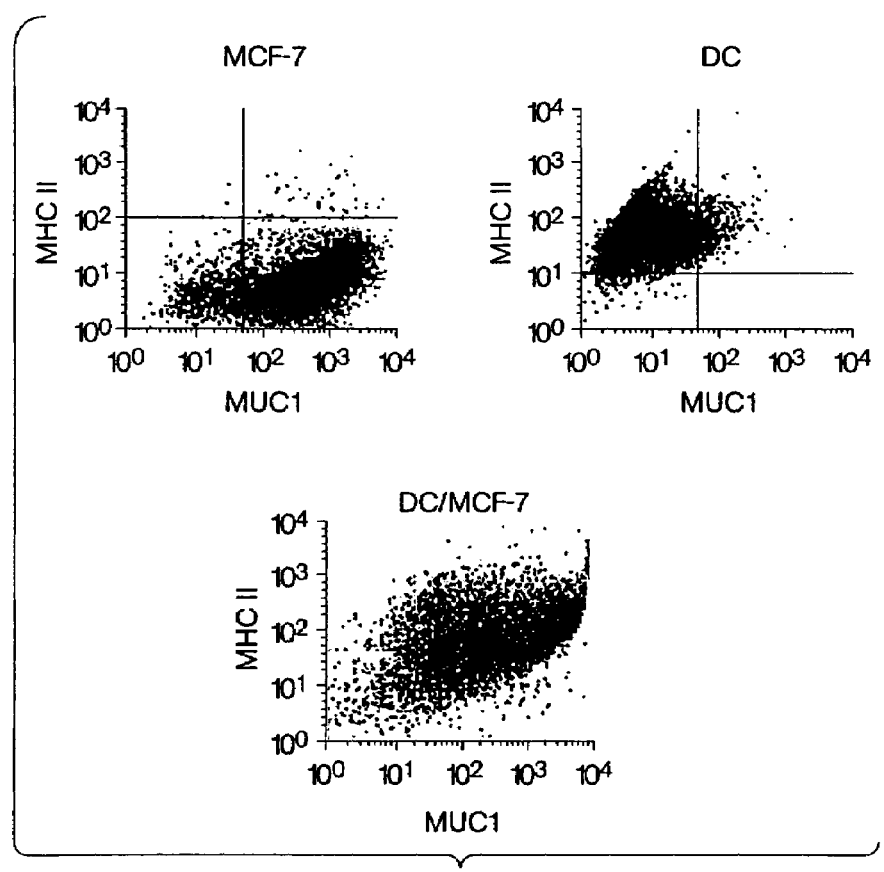
FIG. 4A is a series of bi-dimensional flow cytometry histograms showing expression of MUC1 and MHC class II on MCF-7 breast cancer cells, human dendritic cells, and fused DC/MCF-7 cells.
Figure 4B:
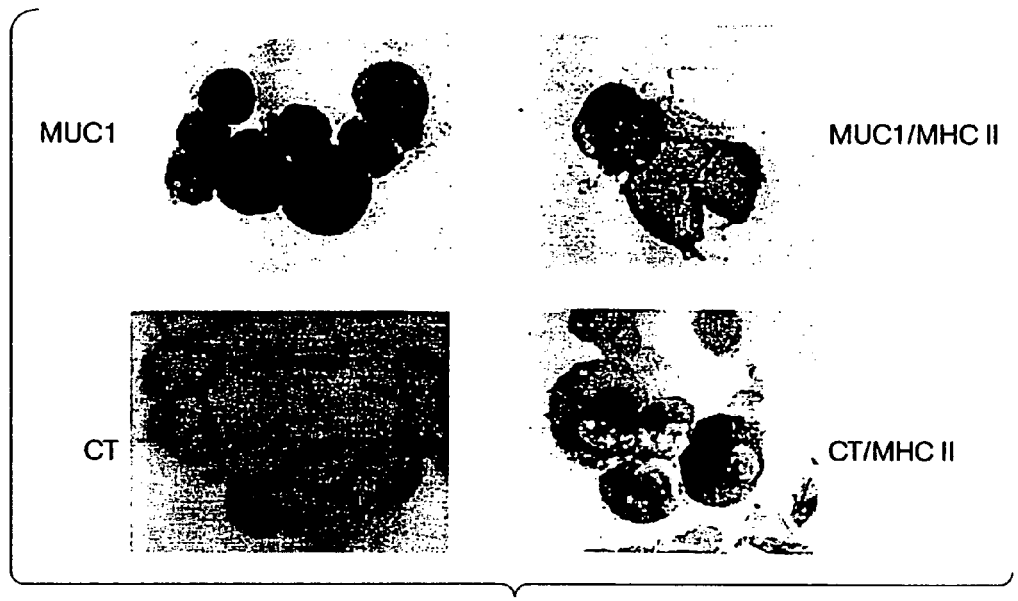
FIG. 4B is a series of photomicrographs showing expression of MUC1 (top left) and cytokeratin (CT) (bottom left) in primary human breast cancer cells and of MUC1 and MEC class II (top right) and cytokeratin and MHC class II (bottom right) in human DC/primary breast cancer fused cells.
Figure 4C:
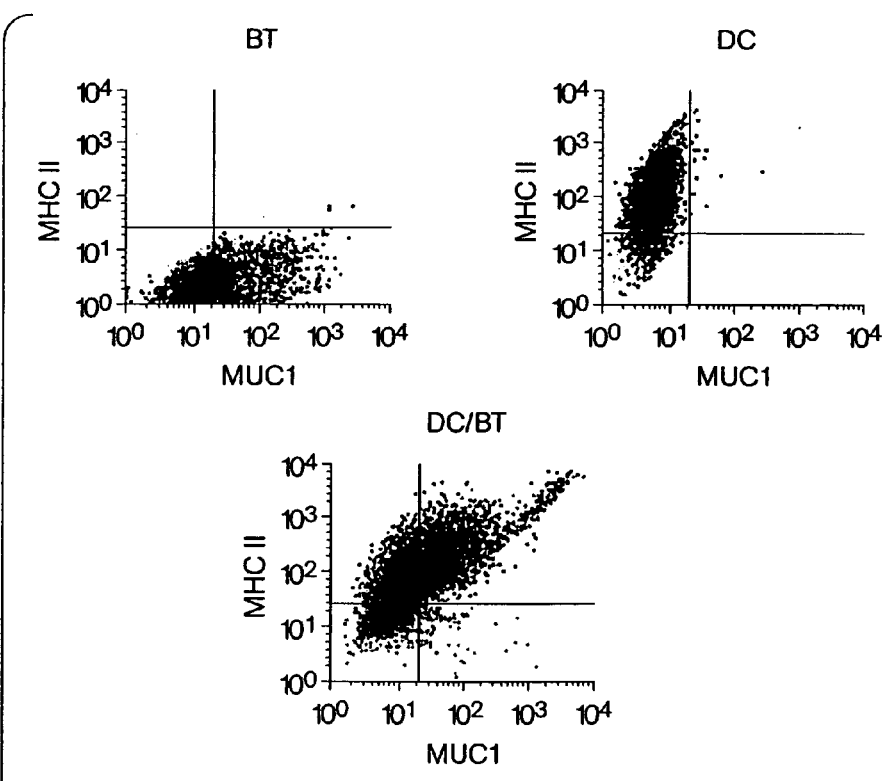
FIG. 4C is a series of bi-dimensional flow cytometry histograms showing expression of MHC class II and MUC1 on primary human breast cancer cells (BT), autologous human dendritic cells (DC), and BT/DC fused cells.
Figure 5A:
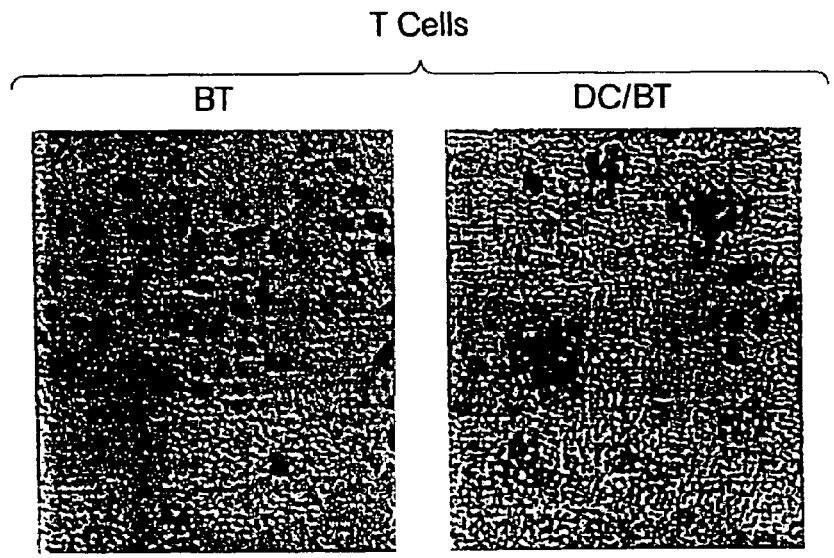
FIG. 5A is a pair of photomicrographs showing clustering of autologous T cells around BT/DC fused cells (right) but not BT cells (left).
Figure 5B:
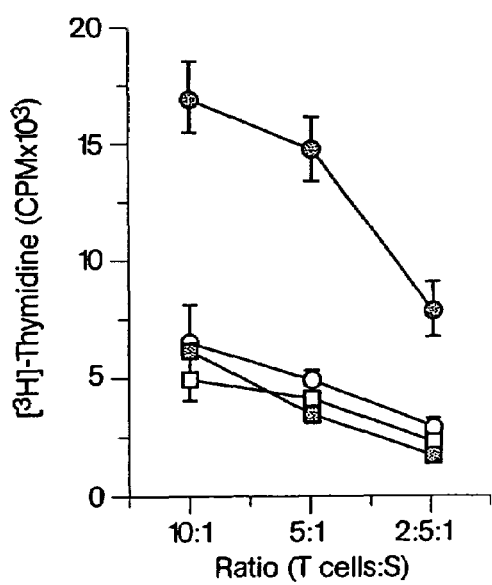
FIG. 5B is a line graph showing the proliferation of T cells in response to stimulation with DC (open circle), autologous BT cells (open box), autologous BT cells mixed with autologous DC (shaded box), or autologous BT/DC fusion cells (shaded circle) at the indicated ratios of T cells to stimulator cells (S).
Figure 5C:
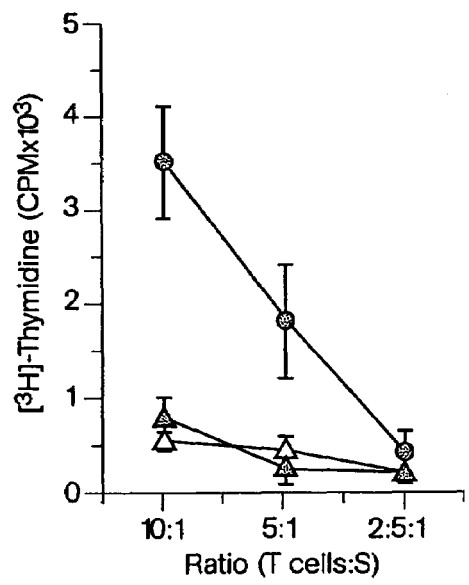
FIG. 5C is a line graph showing the proliferation of T cells in response to stimulation by PEG-treated autologous DC (open triangle), autologous DC fused to monocytes (shaded triangle), or autologous BT/DC fused cells (open circle).
Figure 6A:
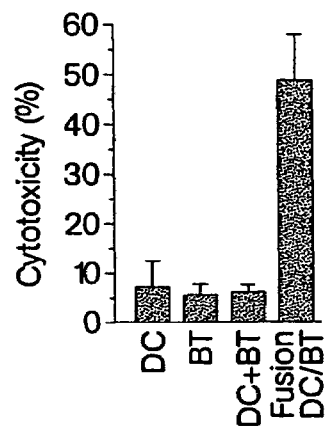
FIG. 6A is a bar graph showing the cytolysis of autologous BT target cells by T cells stimulated, in the presence of human IL-2, with autologous DC, autologous BT cells, autologous DC mixed with autologous BT cells (DC+BT), or autologous DC/BT fused cells.
Figure 6B:
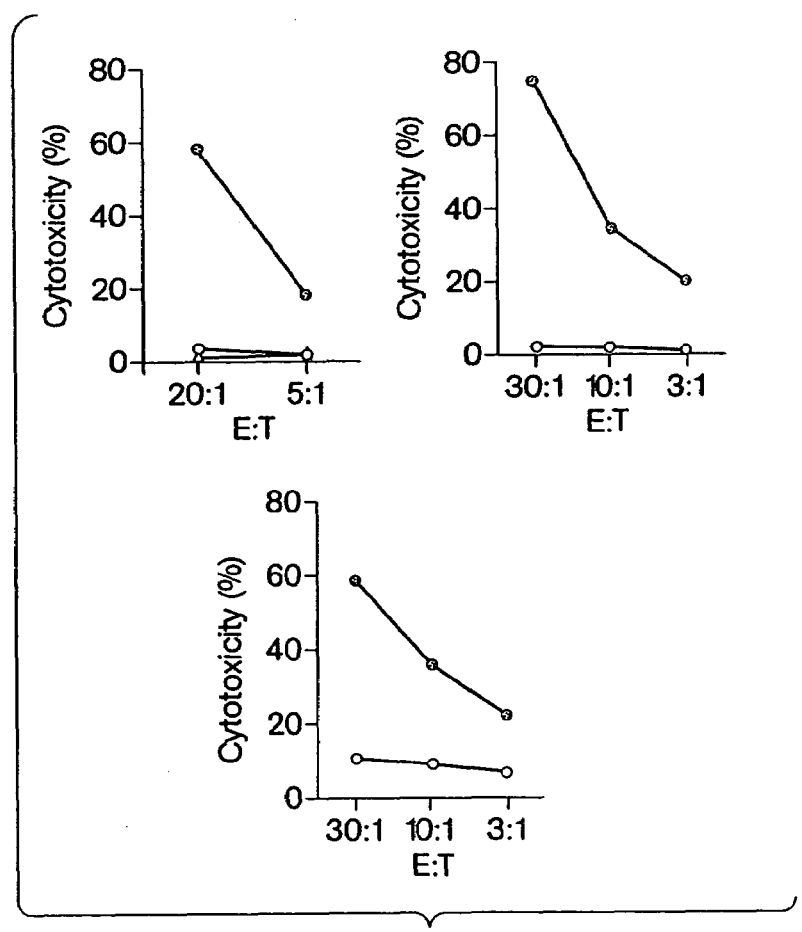
FIG. 6B is a set of three line graphs showing data obtained with cells from three different breast cancer patients. The graphs show the cytolysis of autologous BT target cells by T cells stimulated with either autologous BT cells (open circle) or DC/BT fusion cells (shaded circle).
Figure 7A:
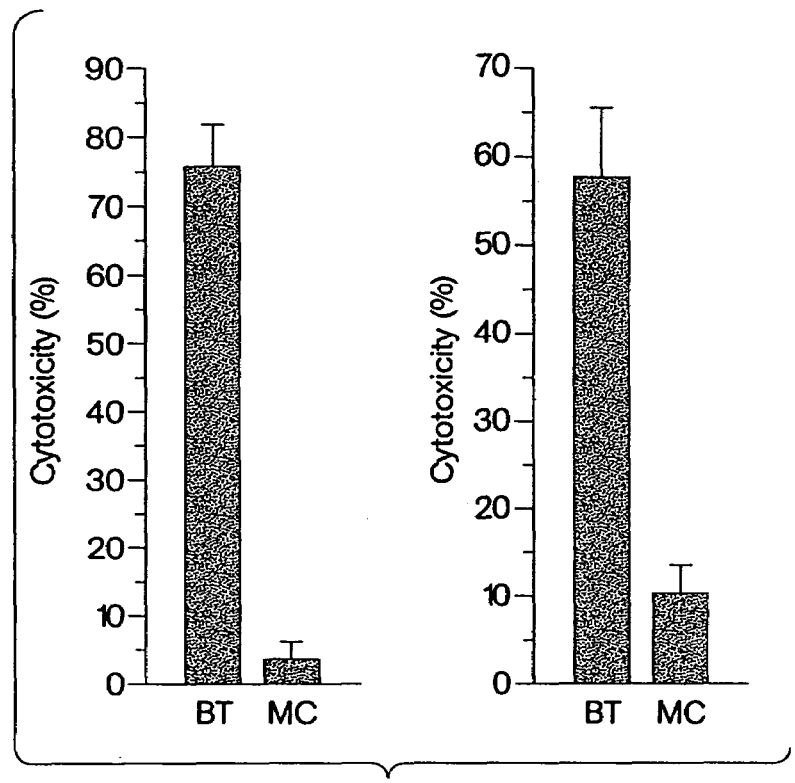
FIG. 7A is a pair of bar graphs showing data obtained with cells from two different breast cancer patients. The graphs show the cytolysis of autologous BT cells or autologous monocytes (MC) by T cells stimulated with autologous DC/BT fused cells.
Figure 7B:
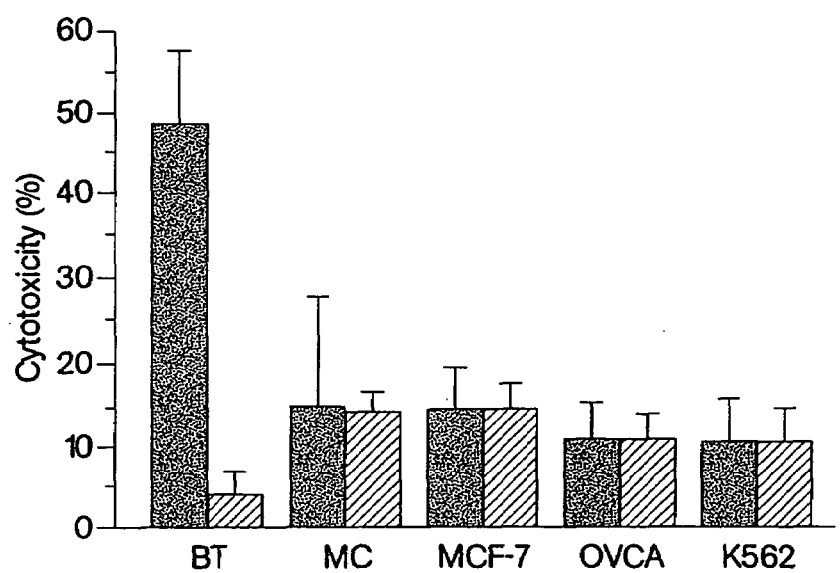
FIG. 7B is a bar graph showing the cytolysis, in the absence (solid bars) and presence (hatched bars) of antibody specific for human MHC class I molecules, of autologous BT cells, autologous MC, MCF-7 breast cancer cells, ovarian cancer cells (OVCA), and K562 cells by T cells stimulated with autologous DC/BT fused cells.
Figure 8A:
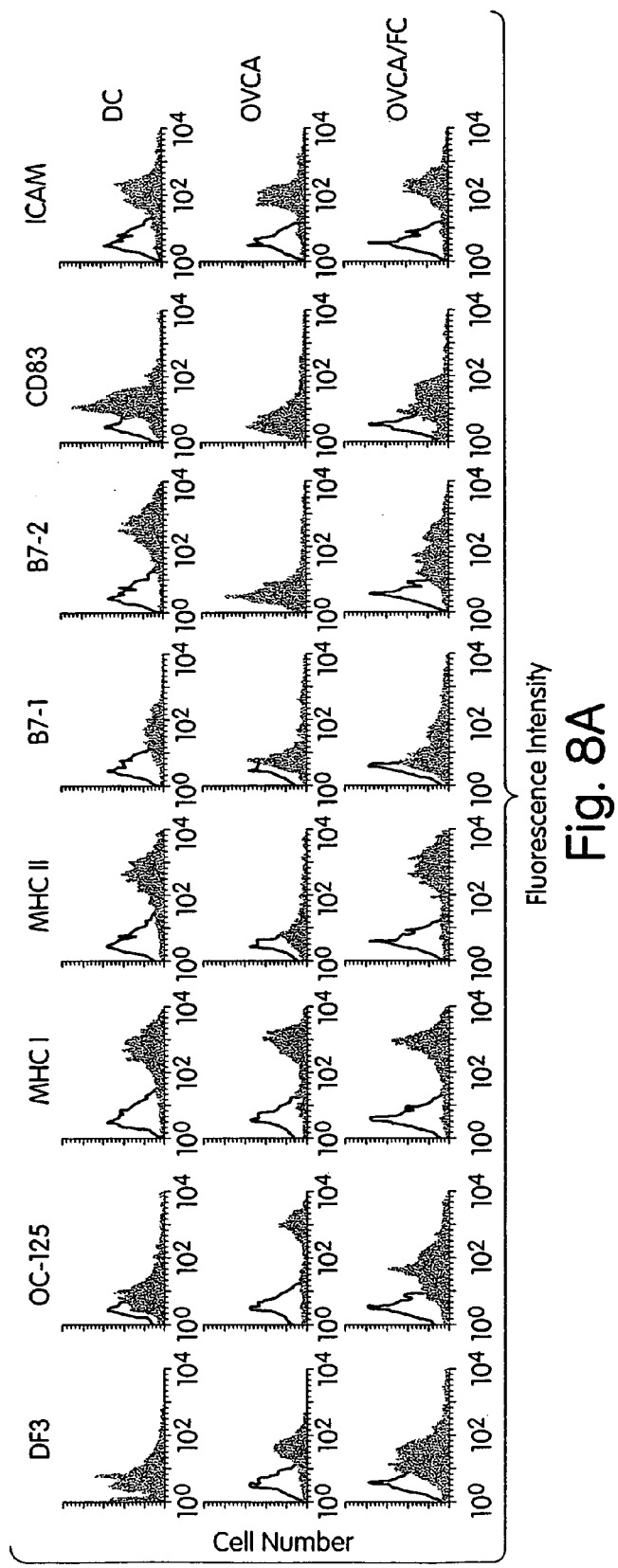
FIG. 8A is a series of flow cytometry histograms showing the expression of a variety of cell surface molecules on human DC, ovarian carcinoma cells (OVCA), and OVCA/DC fused cells (OVCA/FC).
Figure 8B:
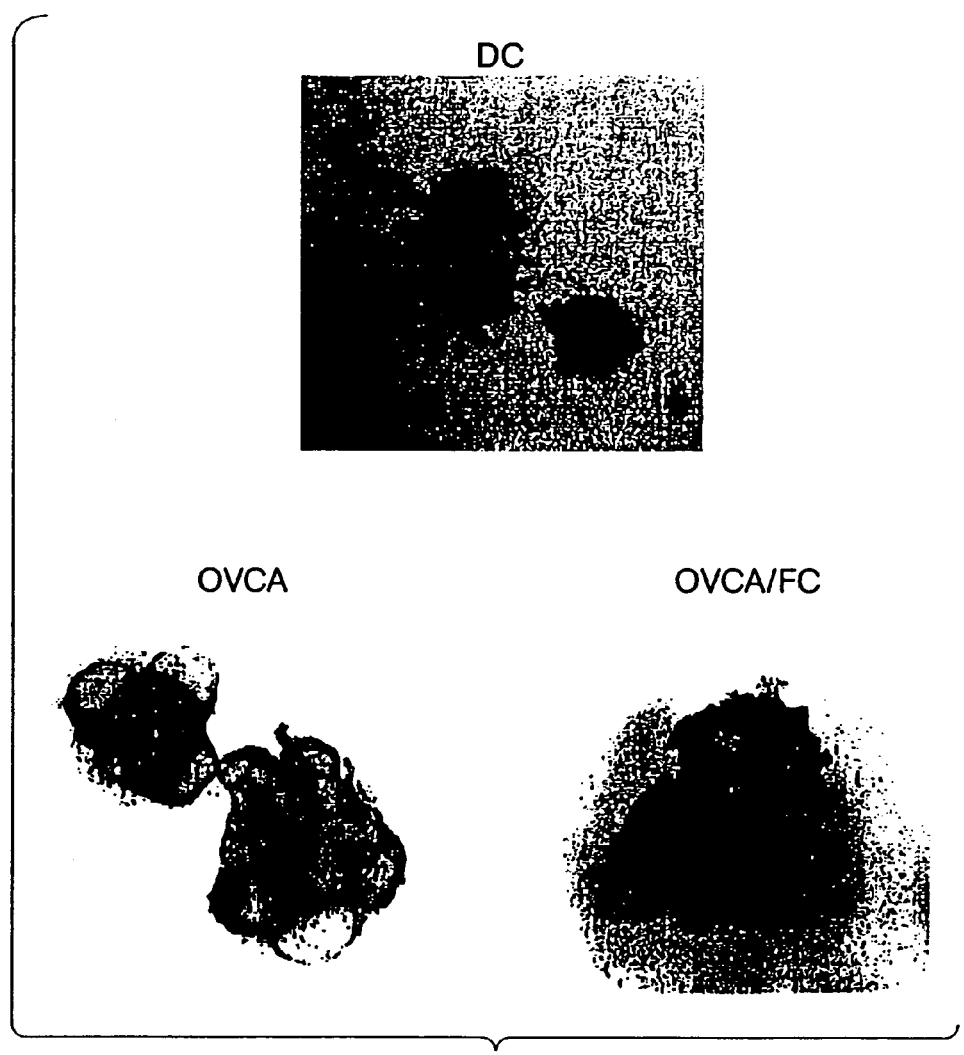
FIG. 8B is a series of photomicrographs showing expression of HLA-DR (MHC class II) in DC, OVCA, and OVCA/DC fused cells (OVCA/FC).
Figure 9:
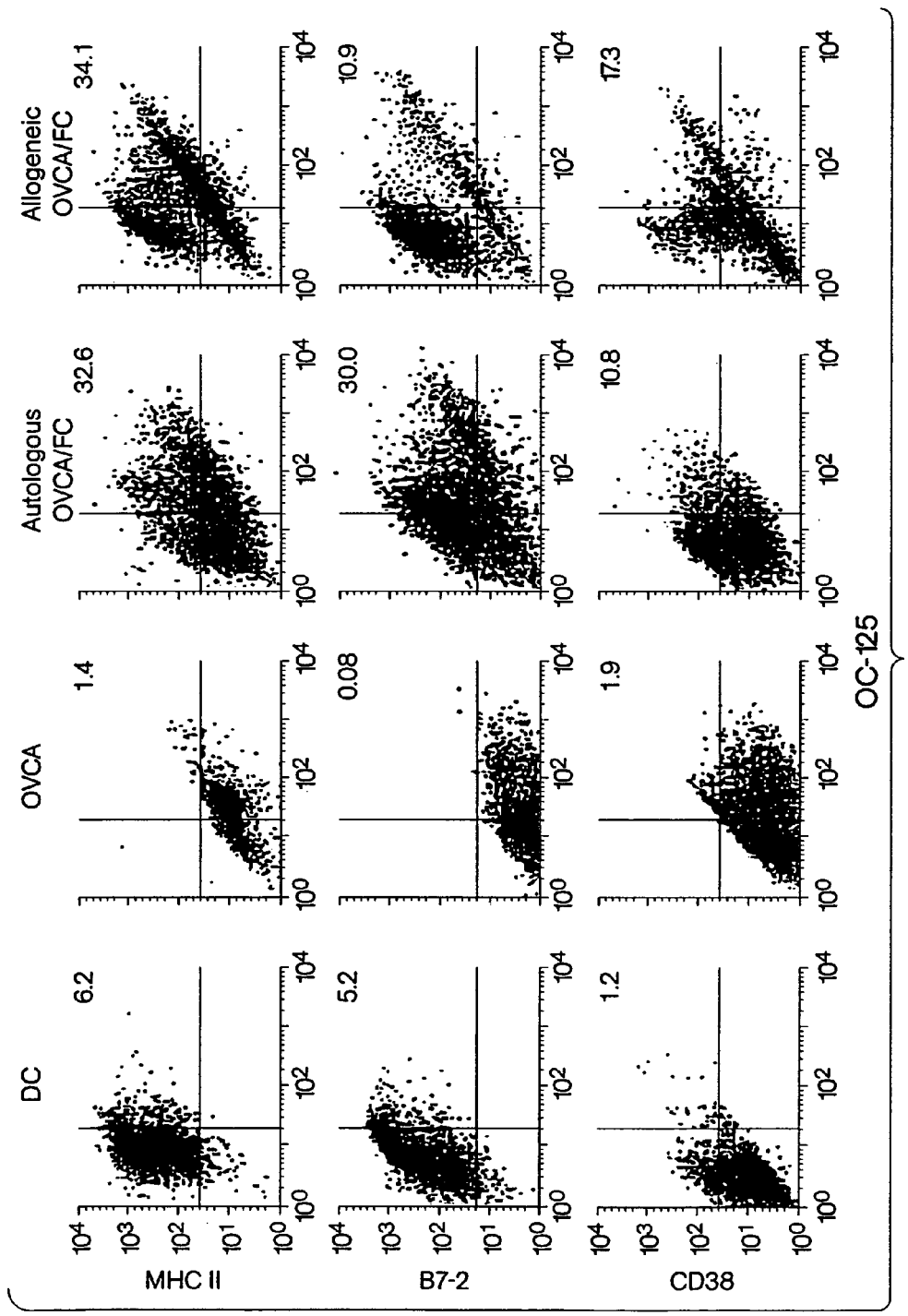
FIG. 9 is a series of bi-dimensional flow cytometry histograms showing expression of CA-125 (OC-125), MHC class II (MHC II), B7-2, and CD38 on DC, OVCA cells, autologous OVCA/DC fused cells (autologous OVCA/FC), and allogeneic OVCA/DC fusion cells (allogeneic OVCA/FC).
Figure 10A:
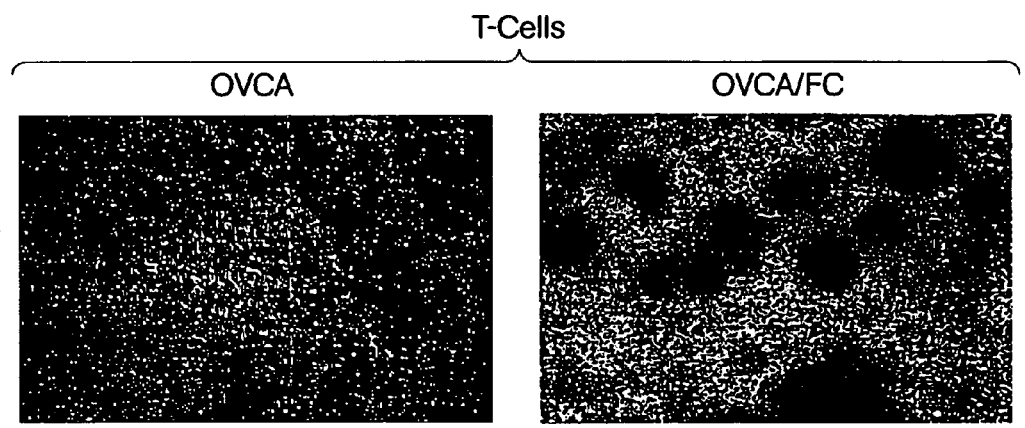
FIG. 10A is a pair of photomicrographs showing clustering of autologous T cells around OVCA/DC fused cells (OVCA/FC) (right) but not OVCA cells (left).
Figure 10B:
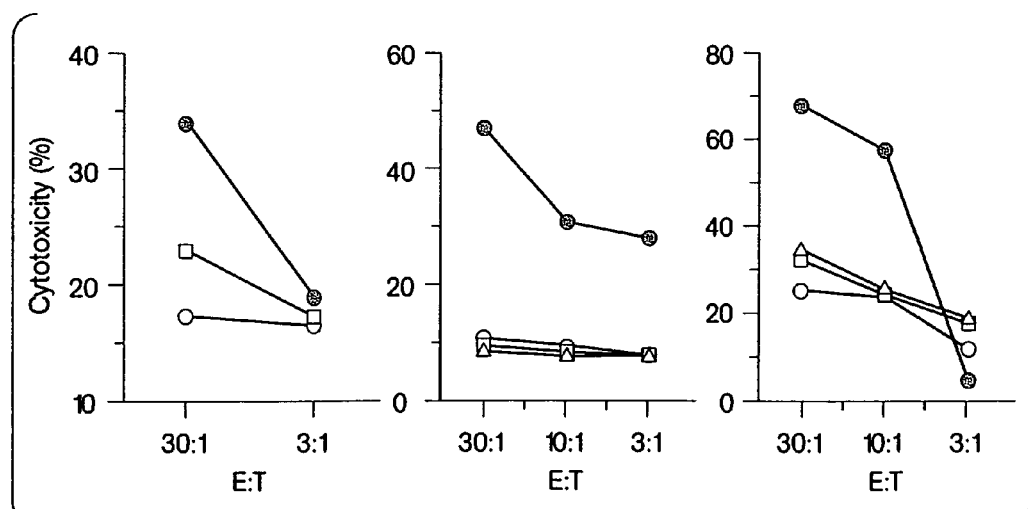
FIG. 10B is a set of three line graphs showing data obtained with cells from three different ovarian carcinoma patients. The graphs show the cytolysis of autologous OVCA target cells by T cells stimulated with either autologous DC (open circle), autologous OVCA cells (open box), autologous OVCA cells mixed with DC (open triangle), or OVCA/DC fused cells (shaded circle).
Figure 10C:
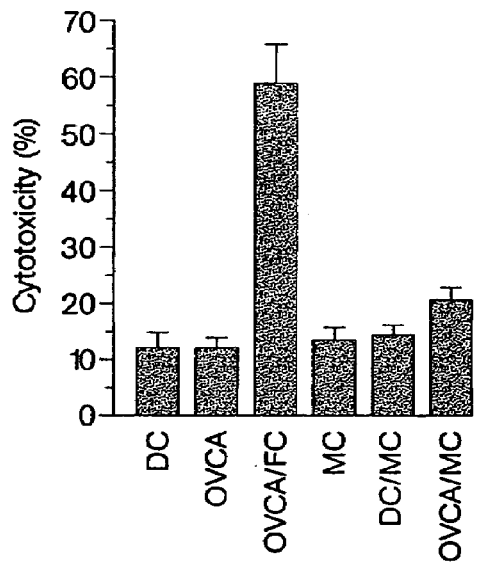
FIG. 10C is a bar graph showing cytolysis of autologous OVCA target cells by T cells stimulated with either autologous DC, autologous OVCA cells, autologous OVCA/DC fused cells (OVCA/FC), autologous monocytes (MC), autologous monocytes fused to autologous DC (DC/MC), or autologous OVCA cells fused to autologous monocytes (OVCA/MC).
Figure 11A:
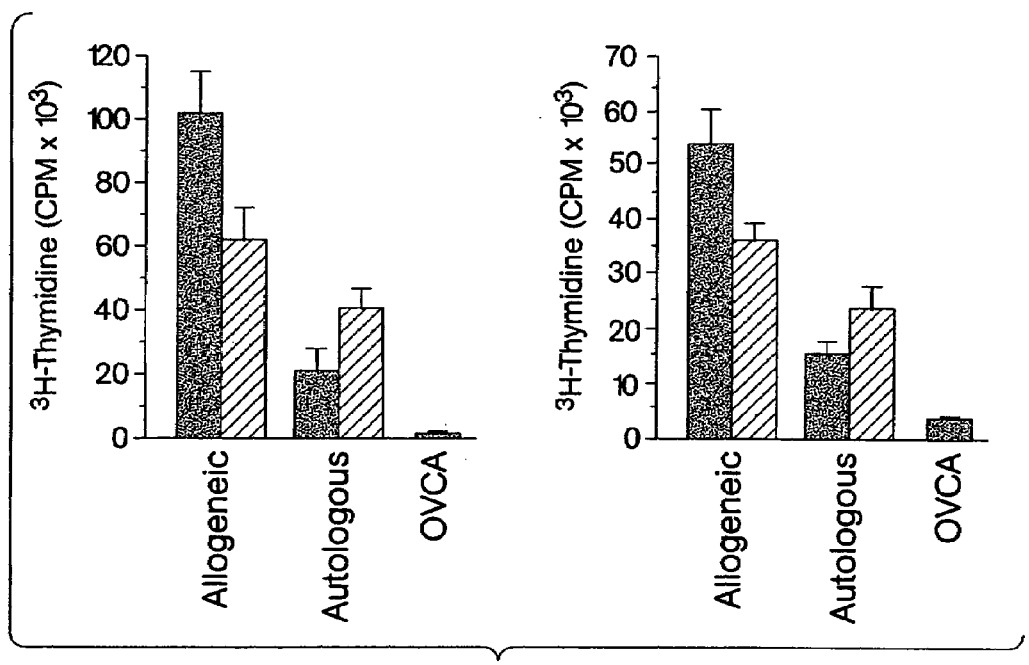
FIG. 11A is a pair of bar graphs showing data obtained with cells from two different breast cancer patients. The graphs proliferative responses the T cells stimulated with autologous or allogeneic DC (solid bar) or OVAC/DC fused cells (hatched bar) produced by fusion of autologous OVCA cells with the autologous or allogeneic DC.
Figure 11B:
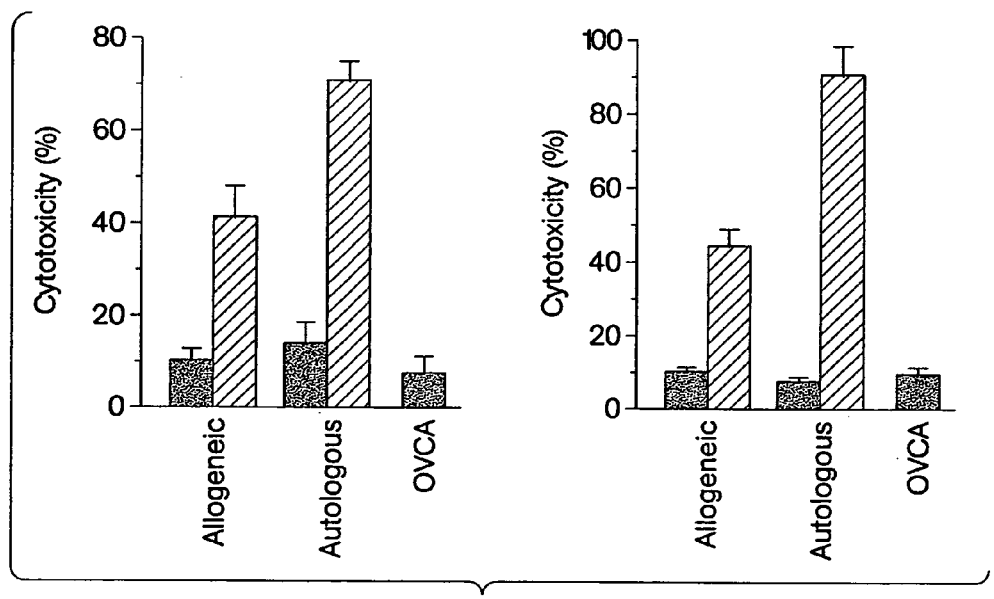
FIG. 11B is a pair of bar graphs showing data obtained with cells from two different breast cancer patients. The graphs show the cytolysis of autologous OVCA cells by T cells stimulated with autologous or allogeneic DC (solid bar), OVAC/DC fused cells (hatched bar) produced by fusion of autologous OVCA cells with the autologous or allogeneic DC, or autologous OVCA cells.
Figure 12A:
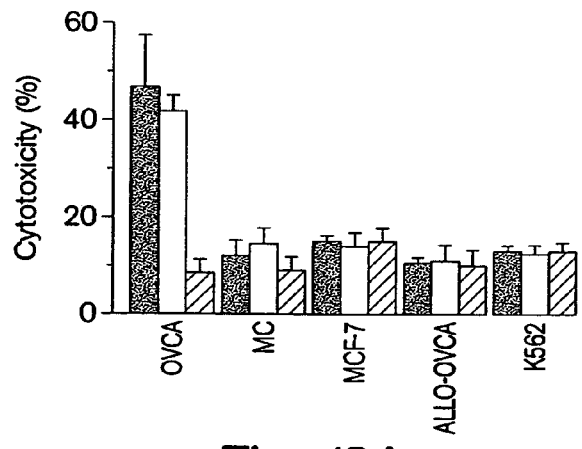
FIG. 12A is a bar graph showing the cytolysis, in the absence (solid bars) and presence (hatched bars) of antibody specific for human MHC class I molecules, of autologous OVCA cells, autologous monocytes (MC), MCF-7 breast cancer cells, allogeneic ovarian cancer cells (Allo-OVCA), and K562 cells by T cells stimulated with autologous OVCA/DC fused cells.
Figure 12B:
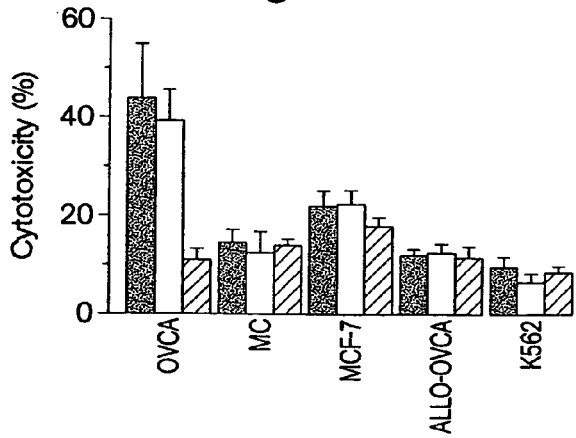
FIG. 12B is a bar graph showing the cytolysis, in the absence (solid bars) and presence (hatched bars) of antibody specific for human MHC class I molecules, of autologous OVCA cells, autologous monocytes (MC), MCF-7 breast cancer cells, allogeneic ovarian cancer cells (Allo-OVCA), and K562 cells by T cells stimulated with allogeneic OVCA/DC fused cells.
Figure 13:
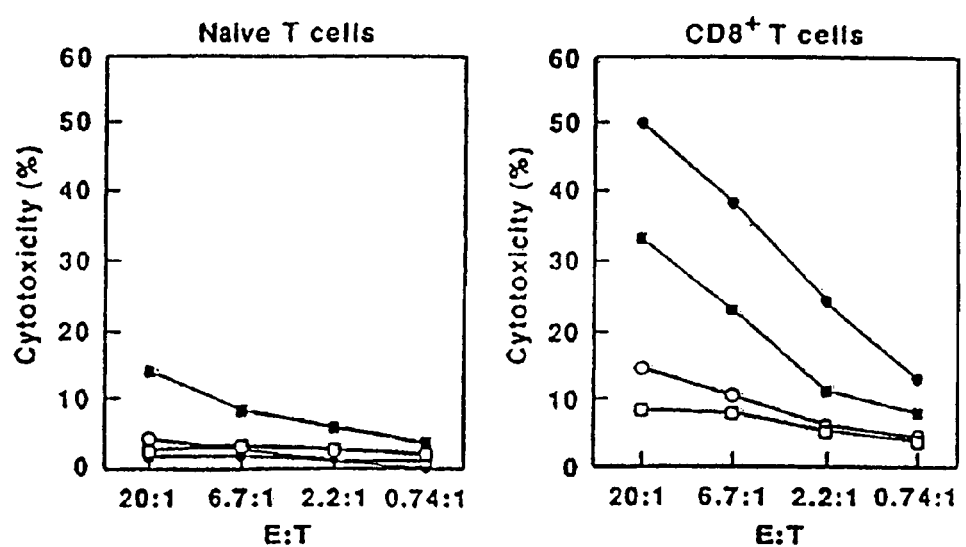
FIG. 13 shows the induction of MUC1-specific CTLs by FC/MUC1. Naïve lymph node cells isolated from unimmunized MUC1.Tg mice or CD8+ T cells isolated from FC/MUC1-immunized MUC1.Tg mice were incubated at the indicated effector:target ratios with $^{51}$Cr-labeled MC-38 (open circle), MC-38/MUC1 (shaded circle), MB49 (open box), and MB49/MUC1 (shaded box) target cells. CTL activity was determined by $^{51}$Cr-release.

Various publications, patents and published patent specifications are referenced within the specification by an identifying citation. The disclosures of these publications, patents and published patent specifications are hereby incorporated by reference into the present disclosure to more fully describe the state of the art to which this invention pertains.

Definitions

The practice of the present invention employs, unless otherwise indicated, conventional techniques of molecular biology, microbiology, cell biology and recombinant DNA, which are within the skill of the art. See, e.g., Sambrook, Fritsch and Maniatis, MOLECULAR CLONING: A LABORATORY MANUAL, 2$^{nd}$ edition (1989); CURRENT PROTOCOLS IN MOLECULAR BIOLOGY (F. M. Ausubel et al. eds., (1987)); the series METHODS IN ENZYMOLOGY (Academic Press, Inc.): PCR 2: A PRACTICAL APPROACH (Mi. MacPherson, B. D. Hames and G. R. Taylor eds. (1995)) and ANIMAL CELL CULTURE (Rd. Freshney, ed. (1987)).

As used herein, certain terms have the following defined meanings. As used in the specification and claims, the singular form "a", "an" and "the" include plural references unless the context clearly dictates otherwise. For example, the term "a cell" includes a plurality of cells, including mixtures thereof.

The term "immune effector cells" refers to cells that specifically recognize an antigen present, for example on a neoplastic or tumor cell. For the purposes of this invention, immune effector cells include, but are not limited to, B cells, monocytes, macrophages, NK cells and T cells such as cytotoxic T lymphocytes (CTLs), for example CTL lines, CTL clones, and CTLs from tumor, inflammatory sites or other infiltrates. "T-lymphocytes" denotes lymphocytes that are phenotypically CD3+, typically detected using an anti-CD3 monoclonal antibody in combination with a suitable labeling technique. The T-lymphocytes of this invention are also generally positive for CD4, CD8, or both. The term "naïve" immune effector cells refers to immune effector cells that have not encountered antigen and is intended to by synonymous with unprimed and virgin. "Educated" refers to immune effector cells that have interacted with an antigen such that they differentiate into an antigen-specific cell.

The terms "antigen presenting cells" or "APCs" includes both intact, whole cells as well as other molecules which are capable of inducing the presentation of one or more antigens, preferably with class I MHC molecules. Examples of suitable APCs are discussed in detail below and include, but are not limited to, whole cells such as macrophages, dendritic cells, B cells; purified MHC class I molecules complexed to β2-microglobulin; and foster antigen presenting cells.

Dendritic cells (DCs) are potent APCs. DCs are minor constituents of various immune organs such as spleen, thymus, lymph node, epidermis, and peripheral blood. For instance, DCs represent merely about 1% of crude spleen (Steinman et al. (1979) J. Exp. Med 149: 1) or epidermal cell suspensions (Schuler et al. (1985) J. Exp. Med 161:526; and Romani et al. J. Invest. Dermatol (1989) 93: 600), and 0.1-1% of mononuclear cells in peripheral blood (Freudenthal et al. Proc. Natl Acad Sci USA (1990) 87: 7698). The following references describe methods for isolating DCs from peripheral blood or bone marrow progenitors. Inaba et al. (1992) J. Exp. Med 175:1157; Inaba et al. (1992) J. Exp, Med 176: 1693-1702; Romani et al. (1994) J. Exp. Med. 180: 83-93; and Sallusto et al. (1994) J. Exp. Med 179: 1109-1118). The preferred methods for isolation and culturing of DCs are described in Bender et al. (1996) J. Immun. Meth. 196:121-135 and Romani et al. (1996) J. Immun. Meth 196:137-151.

"Foster antigen presenting cells" refers to any modified or naturally occurring cells (wild-type or mutant) with antigen presenting capability that are utilized in lieu of antigen presenting cells ("APC") that normally contact the immune effector cells they are to react with. In other words, they are any functional APCs that T cells would not normally encounter in vivo.

It has been shown that DCs provide all the signals required for T cell activation and proliferation. These signals can be categorized into two types. The first type, which gives specificity to the immune response, is mediated through interaction between the T-cell receptor/CD3 ("TCR/CD3") complex and an antigenic peptide presented by a major histocompatibility complex ("MHC") class I or II protein on the surface of APCs. This interaction is necessary, but not sufficient, for T cell activation to occur. In fact, without the second type of signals, the first type of signals can result in T cell anergy. The second type of signals, called costimulatory signals, are neither antigen-specific nor MHC restricted, and can lead to a full proliferation response of T cells and induction of T cell effector functions in the presence of the first type of signals.

Thus, the term "cytokine" refers to any of the numerous factors that exert a variety of effects on cells, for example, inducing growth or proliferation. Non-limiting examples of cytokines include, IL-2, stem cell factor (SCF), IL-3, IL-6, IL-12, G-CSF, GM-CSF, IL-1 alpha, IL-1 beta, MIP-1 alpha, LIF, c-kit ligand, TPO, and flt3 ligand. Cytokines are commercially available from several vendors such as, for example, Genzyme Corp. (Framingham, Mass.), Genentech (South San Francisco, Calif.), Amgen (Thousand Oaks, Calif.) and Immunex (Seattle, Wash.). It is intended, although not always explicitly stated, that molecules having similar biological activity as wild-type or purified cytokines (e.g., recombinantly produced) are intended to be used within the spirit and scope of the invention and therefore are substitutes for wild-type or purified cytokines.

"Costimulatory molecules" are involved in the interaction between receptor-ligand pairs expressed on the surface of antigen presenting cells and T cells. One exemplary receptor-ligand pair is the B7 co-stimulatory molecules on the surface of DCs and its counter-receptor CD28 or CTLA-4 on T cells (Freeman et al. (1993) Science 262:909-911; Young et al. (1992) J. Clin. Invest 90: 229; and Nabavi et al. Nature 360: 266). Other important costimulatory molecules are CD40, CD54, CD80, and CD86. These are commercially available from vendors identified above.

A "hybrid" cell refers to a cell having both antigen presenting capability and also expresses one or more specific antigens. In one embodiment, these hybrid cells are formed by fusing, in vitro, APCs with cells that are known to express the one or more antigens of interest.

A "control" cell refers to a cell that does not express the same antigens as the population of antigen-expressing cells.

The term "culturing" refers to the in vitro propagation of cells or organisms on or in media of various kinds, it is understood that the descendants 30 of a cell grown in culture may not be completely identical (i.e., morphologically, genetically, or phenotypically) to the parent cell. By "expanded" is meant any proliferation or division of cells.

An "effective amount" is an amount sufficient to effect beneficial or desired results. An effective amount can be administered in one or more administrations, applications or dosages. For purposes of this invention, an effective amount of hybrid cells is that amount which promotes expansion of the antigenic-specific immune effector cells, e.g., T cells.

An "isolated" population of cells is "substantially free" of cells and materials with which it is associated in nature. By "substantially free" or "substantially pure" is meant at least 50% of the population are the desired cell type, preferably at least 70%, more preferably at least 80%, and even more preferably at least 90%. An "enriched" population of cells is at least 5% fused cells. Preferably, the enriched population contains at least 10%, more preferably at least 20%, and most preferably at least 25% fused cells.

The term "autogeneic", or "autologous", as used herein, indicates the origin of a cell. Thus, a cell being administered to an individual (the "recipient") is autogeneic if the cell was derived from that individual (the "donor") or a genetically identical individual. An autogeneic cell can also be a progeny of an autogeneic cell. The term also indicates that cells of different cell types are derived from the same donor or genetically identical donors. Thus, an effector cell and an antigen presenting cell are said to be autogeneic if they were derived from the same donor or from an individual genetically identical to the donor, or if they are progeny of cells derived from the same donor or from an individual genetically identical to the donor.

Similarly, the term "allogeneic", as used herein, indicates the origin of a cell. Thus, a cell being administered to an individual (the "recipient") is allogeneic if the cell was derived from an individual not genetically identical to the recipient; in particular, the term relates to non-identity in expressed MHC molecules. An allogeneic cell can also be a progeny of an allogeneic cell. The term also indicates that cells of different cell types are derived from genetically non-identical donors, or if they are progeny of cells derived from genetically non-identical donors. For example, an APC is said to be allogeneic to an effector cell if they are derived from genetically non-identical donors.

A "subject" is a vertebrate, preferably a mammal, more preferably a human. Mammals include, but are not limited to, murines, simians, humans, farm animals, sport animals, and pets.

As used herein, a "genetic modification" refers to any addition, deletion or disruption to a cell's endogenous nucleotides.

A "viral vector" is defined as a recombinantly produced virus or viral particle that comprises a polynucleotide to be delivered into a host cell, either in vivo, ex vivo or in vitro. Examples of viral vectors include retroviral vectors, adenovirus vectors, adeno-associated virus vectors and the like. In aspects where gene transfer is mediated by a retroviral vector, a vector construct refers to the polynucleotide comprising the retroviral genome or part thereof, and a therapeutic gene.

As used herein, "retroviral mediated gene transfer" or "retroviral transduction" carries the same meaning and refers to the process by which a gene or a nucleic acid sequence is stably transferred into the host cell by virtue of the virus entering the cell and integrating its genome into the host cell genome. The virus can enter the host cell via its normal mechanism of infection or be modified such that it binds to a different host cell surface receptor or ligand to enter the cell.

Retroviruses carry their genetic information in the form of RNA; however, once the virus infects a cell, the RNA is reverse-transcribed into the DNA form that integrates into the genomic DNA of the infected cell. The integrated DNA form is called a provirus.

In aspects where gene transfer is mediated by a DNA viral vector, such as a adenovirus (Ad) or adeno-associated virus (AAV), a vector construct refers to the polynucleotide comprising the viral genome or part thereof, and a therapeutic gene. Adenoviruses (Ads) are a relatively well characterized, homogenous group of viruses, including over 50 serotypes. (see, e.g., WO 95/27071) Ads are easy to grow and do not integrate into the host cell genome. Recombinant Ad-derived vectors, particularly those that reduce the potential for recombination and generation of wild-type virus, have also been constructed. (see, WO 95/00655; WO 95/11984). Wild-type AAV has high infectivity and specificity integrating into the host cells genome. (Hermonat and Muzyczka (1984) PNAS USA 81:6466-6470; Lebkowski et al., (1988) Mol Cell Biol 8:3988-3996).

Vectors that contain both a promoter and a cloning site into which a polynucleotide can be operatively linked are well known in the art. Such vectors are capable of transcribing R.NA in vitro or in vivo, and are commercially available from sources such as Stratagene (La Jolla, Calif.) and Promega Biotech (Madison, Wis.). In order to optimize expression and/or in vitro transcription, it may be necessary to remove, add or alter 5' and/or 3' untranslated portions of the clones to eliminate extra, potential inappropriate alternative translation initiation codons or other sequences that may interfere with or reduce expression, either at the level of transcription or translation. Alternatively, consensus ribosome binding sites can be inserted immediately 5' of the start codon to enhance expression. Examples of vectors are viruses, such as baculovirus and retrovirus, bacteriophage, cosmid, plasmid, fungal vectors and other recombination vehicles typically used in the art which have been described for expression in a variety of eucaryotie and prokaryotic hosts, and may be used for gene therapy as well as for simple protein expression.

Among these are several non-viral vectors, including DNA/liposome complexes, and targeted viral protein DNA complexes. To enhance delivery to a cell, the nucleic acid or proteins of this invention can be conjugated to antibodies or binding fragments thereof which bind cell surface antigens, e.g., TCR, CD3 or CD4. Liposomes that also comprise a targeting antibody or fragment thereof can be used in the methods of this invention. This invention also provides the targeting complexes for use in the methods disclosed herein.

Polynucleotides are inserted into vector genomes using methods well known in the art. For example, insert and vector DNA can be contacted, under suitable conditions, with a restriction enzyme to create complementary ends on each molecule that can pair with each other and be joined together with a ligase. Alternatively, synthetic nucleic acid linkers can be ligated to the termini of restricted polynucleotide. These synthetic linkers contain nucleic acid sequences that correspond to a particular restriction site in the vector DNA. Additionally, an oligonucleotide containing a termination codon and an appropriate restriction site can be ligated for insertion into a vector containing, for example, some or all of the following: a selectable marker gene, such as the neomycin gene for selection of stable or transient transfectants in mammalian cells; enhancer/promoter sequences from the immediate early gene of human CMV for high levels of transcription; transcription termination and RNA processing signals from SV4O for mRNA stability; SV40 polyoma origins of replication and ColEI for proper episomal replication; versatile multiple cloning sites; and T7 and SP6 RNA promoters for in vitro transcription of sense and antisense RNA. Other means are well known and available in the art.

As used herein, "expression" refers to the process by which polynucleotides are transcribed into mRNA and translated into peptides, polypeptides, or proteins. If the polynucleotide is derived from genomic DNA, expression may include splicing of the mRNA, if an appropriate eucaryotic host is selected. Regulatory elements required for expression include promoter sequences to bind RNA polymerase and transcription initiation sequences for ribosome binding. For example, a bacterial expression vector includes a promoter such as the lac promoter and for transcription initiation the Shine-Dalgamo sequence and the start codon AUG (Sambrook et al. (1989), supra). Similarly, a eucaryotic expression vector includes a heterologous or homologous promoter for RNA polymerase II, a downstream polyadenylation signal, the start codon AUG, and a termination codon for detachment of the ribosome. Such vectors can be obtained commercially or assembled by the sequences described in methods well known in the art, for example, the methods described above for constructing vectors in general.

The terms "major histocompatibility complex" or "MHC" refers to a complex of genes encoding cell-surface molecules that are required for antigen presentation to immune effector cells such as T cells and for rapid graft rejection. In humans, the MHC complex is also known as the HLA complex. The proteins encoded by the MHC complex are known as "MHC molecules" and are classified into class I and class II MHC molecules. Class I MHC molecules include membrane heterodimeric proteins made up of an α chain encoded in the MHC associated noncovalently with β2-microglobulin. Class I MHC molecules are expressed by nearly all nucleated cells and have been shown to function in antigen presentation to CD8+ T cells. Class I molecules include HLA-A, -B, and -C in humans. Class 11 MHC molecules also include membrane heterodimeric proteins consisting of noncovalently associated and J3 chains. Class II M}ICs are known to function in CD4+ T cells and, in humans, include HLA-DP, -DQ, and DR. The term "MHC restriction" refers to a characteristic of T cells that permits them to recognize antigen only after it is processed and the resulting antigenic peptides are displayed in association with either a class I or class II MHC molecule. Methods of identifying and comparing MHC are well known in the art and are described in Allen M. et al. (1994) Human Imm. 40:25-32; Santamaria P. et al. (1993) Human Imm. 37:39-50; and Hurley C. K. et al. (1997) Tissue Antigens 50:401-415.

The term "sequence motif" refers to a pattern present in a group of 15 molecules (e.g., amino acids or nucleotides). For instance, in one embodiment, the present invention provides for identification of a sequence motif among peptides present in an antigen. In this embodiment, a typical pattern may be identified by characteristic amino acid residues, such as hydrophobic, hydrophilic, basic, acidic, and the like.

The term "peptide" is used in its broadest sense to refer to a compound of two or more subunit amino acids, amino acid analogs, or peptidomimetics. The subunits may be linked by peptide bonds. In another embodiment, the subunit may be linked by other bonds, e.g. ester, ether, etc.

As used herein the term "amino acid" refers to either natural and/or 25 unnatural or synthetic amino acids, including glycine and both the D or L optical isomers, and amino acid analogs and peptidomimetics. A peptide of three or more amino acids is commonly called an oligopeptide if the peptide chain is short. If the peptide chain is long, the peptide is commonly called a polypeptide or a protein.

As used herein, "solid phase support" is used as an example of a "carrier" and is not limited to a specific type of support. Rather a large number of supports are available and are known to one of ordinary skill in the art. Solid phase supports include silica gels, resins, derivatized plastic films, glass beads, cotton, plastic beads, alumina gels. A suitable solid phase support may be selected on the basis of desired end use and suitability for various synthetic protocols. For example, for peptide synthesis, solid phase support may refer to resins such as polystyrene (e.g., PAM-resin obtained from Bachem Inc., Peninsula Laboratories, etc.), POLYHIPE® resin (obtained from Aminotech, Canada), polyamide resin (obtained from Peninsula Laboratories), polystyrene resin grafted with polyethylene glycol (TentaGel®, Rapp Polymere, Tubingen, Germany) or polydimethylacrylamide resin (obtained from . MilligenlBiosearch, California). In a preferred embodiment for peptide synthesis, solid phase support refers to polydimethylacrylamide resin.

The term "aberrantly expressed" refers to polynucleotide sequences in a cell or tissue which are differentially expressed (either over-expressed or under-expressed) when compared to a different cell or tissue whether or not of the same tissue type, i.e., lung tissue versus lung cancer tissue.

A "tag" or "SAGE tag" is a short polynucleotide sequence, generally under about 20 nucleotides, that occur in a certain position in messenger RNA. The tag can be used to identify the corresponding transcript and gene from which it was transcribed. A "ditag" is a dimer of two sequence tags.

"Host cell" or "recipient cell" is intended to include any individual cell or cell culture which can be or have been recipients for vectors or the incorporation of exogenous nucleic acid molecules, polynucleotides and/or proteins. It also is intended to include progeny of a single cell, and the progeny may not necessarily be completely identical (in morphology or in genomic or total DNA complement) to the original parent cell due to natural, accidental, or deliberate mutation. The cells may be procaryotic or eucaryotic, and include but are not limited to bacterial cells, yeast cells, animal cells, and mammalian cells, e.g., murine, rat, simian or human.

An "antibody" is an immunoglobulin molecule capable of binding an antigen. As used herein, the term encompasses not only intact immunoglobulin molecules, but also anti-idiotypic antibodies, mutants, fragments, fusion proteins, humanized proteins and modifications of the immunoglobulin molecule that comprise an antigen recognition site of the required specificity.

An "antibody complex" is the combination of antibody (as defined above) and its binding partner or ligand.

A native antigen is a polypeptide, protein or a fragment containing an epitope, which induces an immune response in the subject.

The term "isolated" means separated from constituents, cellular and otherwise, in which the polynucleotide, peptide, polypeptide, protein, antibody, or fragments thereof, are normally associated with in nature. As is apparent to those of skill in the art, a non-naturally occurring polynucleotide, peptide, polypeptide, protein, antibody, or fragments thereof, does not require "isolation" to distinguish it from its naturally occurring counterpart. In addition, a "concentrated", "separated" or "diluted" polynucleotide, peptide, polypeptide, protein, antibody, or fragments thereof, is distinguishable from its naturally occurring counterpart in that the concentration or number of molecules per volume is greater than "concentrated" or less than "separated" than that of its naturally occurring counterpart. A polynucleotide, peptide, polypeptide, protein, antibody, or fragments thereof, which differs from the naturally occurring counterpart in its primary sequence or for example, by its glycosylation pattern, need not be present in its isolated form since it is distinguishable from its naturally occurring counterpart by its primary sequence, or alternatively, by another characteristic such as glycosylation pattern. Although not explicitly stated for each of the inventions disclosed herein, it is to be understood that all of the above embodiments for each of the compositions disclosed below and under the appropriate conditions, are provided by this invention. Thus, a non-naturally occurring polynucleotide is provided as a separate embodiment from the isolated naturally occurring polynucleotide. A protein produced in a bacterial cell is provided as a separate embodiment from the naturally occurring protein isolated from a eucaryotic cell in which it is produced in nature.

A "composition" is intended to mean a combination of active agent and another compound or composition, inert (for example, a detectable agent, carrier, solid support or label) or active, such as an adjuvant.

A "pharmaceutical composition" is intended to include the combination of an active agent with a carrier, inert or active, making the composition suitable for diagnostic or therapeutic use in vitro, in vivo or ex vivo.

As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin, REMINGTON'S PHARM. SCI, 15th Ed. (Mack Publ. Co., Easton (1975)).

As used herein, the term "inducing an immune response in a subject" is a term well understood in the art and intends that an increase of at least about 2-fold, more preferably at least about 5-fold, more preferably at least about 10-fold, more preferably at least about 100-fold, even more preferably at least about 500-fold, even more preferably at least about 1000-fold or more in an immune response to an antigen (or epitope) can be detected (measured), after introducing the antigen (or epitope) into the subject, relative to the immune response (if any) before introduction of the antigen (or epitope) into the subject. An immune response to an antigen (or epitope), includes, but is not limited to, production of an antigen-specific (or epitope-specific) antibody, and production of an immune cell expressing on its surface a molecule which specifically binds to an antigen (or epitope). Methods of determining whether an immune response to a given antigen (or epitope) has been induced are well known in the art. For example, antigen specific antibody can be detected using any of a variety of immunoassays known in the art, including, but not limited to, ELISA, wherein, for example, binding of an antibody in a sample to an immobilized antigen (or epitope) is detected with a detectably-labeled second antibody (e.g., enzyme-labeled mouse anti-human Ig antibody). Immune effector cells specific for the antigen can be detected any of a variety of assays known to those skilled in the art, including, but not limited to, FACS, or, in the case of CTLs, 51CR-release assays, or 3H-thymidine uptake assays.

Fusions

The invention features (1) immune system-stimulating compositions that contain fused cells formed by fusion between DCs and non-dendritic cells; (2) methods of stimulating an immune system with the compositions; and (3) methods of generating the fused cells.

DCs can be obtained from bone marrow cultures, peripheral blood, spleen, or other appropriate tissue of a mammal using protocols known in the art. Bone marrow contains DC progenitors, which, upon treatment with cytokines such as granulocyte-macrophage colony-stimulating factor ("GM-CSF") and interleukin 4 ("IL-4"), proliferate and differentiate into DCs. Tumor necrosis cell factor (TNF) is optionally used alone or in conjunction with GM-CSF and/or IL-4 to promote maturation of DCs. DCs obtained from bone marrow are relatively immature (as compared to, for instance, spleen DCs). GM-CSF/IL-4 stimulated DC express MHC class I and class II molecules, B7-1, B7-2, ICAM, CD40 and variable levels of CD83. These immature DCs are more amenable to fusion (or antigen uptake) than the more mature DCs found in spleen, whereas more mature DCs are relatively more effective antigen presenting cells. Peripheral blood also contains relatively immature DCs or DC progenitors, which can propagate and differentiate in the presence of appropriate cytokines such as GM-CSF and-which can also be used in fusion.

The non-dendritic cells used in the invention can be derived from any tissue or cancer (e.g., breast cancer, lung, pancreatic cancer, prostate cancer, bladder cancer, neurological cancers, genitourinary cancers, hematological cancers, melanoma and other skin cancers, and gastrointestinal cancers) by well known methods and can be immortalized. Non-dendritic cells expressing a cell-surface antigen of interest can be generated by transfecting the non-dendritic cells of a desired type with a nucleic acid molecule that encodes a polypeptide comprising the antigen. Exemplary cell-surface antigens are MUCI, $\alpha$-fetoprotein, $\gamma$-fetoprotein, carcinoembryonic antigen, fetal sulfoglycoprotein antigen, $\alpha_2$H-ferroprotein, placental alkaline phosphatase, and leukemia-associated membrane antigen. Methods for transfection and identifying antigens are well known in the art.

If the non-dendritic cells die or at least fail to proliferate in the presence of a given reagent and this sensitivity can be overcome by the fusion with DCs, the post-fusion cell mixtures containing the fused as well as the parental cells may optionally be incubated in a medium containing this reagent for a period of time sufficient to eliminate most of the unfused cells. For instance, a number of tumor cell lines are sensitive to HAT due to lack of functional hypoxanthine-guanine phosphoribosyl transferase ("HGPRT"). Fused cells formed by DCs and these tumor cell lines become resistant to HAT, as the DCs contribute functional HGPRT. Thus, a HAT selection can be performed after fusion to eliminate unfused parental cells. Contrary to standard HAT selection techniques, the HAT selection generally should not last for more than 12 days, since Applicants find that lengthy culturing leads to loss of MHC class II protein and/or B7 costimulatory molecules on the fused cells. The fusion product is used directly after the fusion process (e.g., in antigen discovery screening methods or in therapeutic methods) or after a short culture period.

Fused cells are optionally irradiated prior to clinical use. Irradiation induces expression of cytokines, which promote immune effector cell activity.

In the event that the fused cells lose certain DC characteristics such as expression of the APC-specific T-cell stimulating molecules, they (i.e., primary fused cells) can be refused with dendritic cells to restore the DC phenotype. The refused cells (i.e., secondary fused cells) are found to be highly potent APCs. The fused cells can be refused with the dendritic or non-dendritic parental cells as many times as desired.

Fused cells that express MHC class II molecules, B7, or other desired T-cell stimulating molecules can also be selected by panning or fluorescence-activated cell sorting with antibodies against these molecules.

Cells infected with an intracellular pathogen can also be used as the non-dendritic partner of the fusion for treatment of the disease caused by that pathogen. Examples of pathogens include, but are not limited to, viruses (e.g., human immunodeficiency virus, hepatitis A, B, or C virus, papilloma virus, herpes virus, or measles virus), bacteria (e.g., *Corynebacterium diphtheria, Bordetella pertussis*), and intracellular eukaryotic parasites (e.g., *Plasmodiuin* spp., *Schistosoina* spp., *Leishmania* spp., *Trypanosoma* spp., or *Mycobacterium lepre*).

Alternatively, non-dendritic cells transfected with one or more nucleic acid constructs each of which encodes one or more identified cancer antigens or antigens from a pathogen can be used as the non-dendritic partner in fusion. These antigens need not be expressed on the surface of the cancer cells or pathogens, so long as the antigens can be presented by a MHC class I or II molecule on the fused cells.

Methods of Making the Fusions

Fusion between the DCs and the non-dendritic cells can be carried out with well-known methods such as those using polyethylene glycol ("PEG"), Sendai virus, or electrofusion. DCs are autologous or allogeneic. The ratio of DCs to non-dendritic cells in fusion can vary from 1:100 to 1000:1, with a ratio higher than 1:1 being preferred where the nondendritic cells proliferate heavily in culture. After fusion, unfused DCs usually die off in a few days in culture, and the fused cells can be separated from the unfused parental non-dendritic cells by the following two methods, both of which yield fused cells of approximately 50% or higher purity, i.e., the fused cell preparations contain less than 50%, and often less than 30%, unfused cells.

The second method of separating unfused cells from fused cells is based on the different adherence properties between the fused cells and the non-dendritic parental cells. It has been found that the fused cells are generally lightly adherent to tissue culture containers. Thus, if the non-dendritic parental cells are much more adherent, e.g., in the case of carcinoma cells, the post-fusion cell mixtures can be cultured in an appropriate medium (HAT is not needed but may be added if it slows the growth of unfused cells) for a short period of time (e.g., 5-10 days). Subsequently, the fused cells can be gently dislodged and aspirated off, while the unfused cells grow firmly attached to the tissue culture containers. Conversely, if the non-dendritic parental cells grow in suspension, after the culture period, they can be gently aspirated off while leaving the fused cells loosely attached to the containers. Fused cells obtained by the above-described methods typically retain the phenotypic characteristics of DCs. For instance, these fused cells express T-cell stimulating molecules such as MHC class II protein, B7-1, B7-2, and adhesion molecules characteristic of APCs such as ICAM-1. The fused cells also continue to express cell-surface antigens of the parental non-dendritic cells, and are therefore useful for inducing immunity against the cell-surface antigens. Notably, when the non-dendritic fusion partner is a tumor cell, the tumorigenicity of the fused cell is often found to be attenuated in comparison to the parental tumor cell.

In the event that the fused cells lose certain DC characteristics such as expression of the APC-specific T-cell stimulating molecules, they (i.e., primary fused cells) can be re-fused with dendritic cells to restore the DC phenotype. The re-fused cells (i.e., secondary fused cells) are found to be highly potent APCs, and in some cases, have even less tumorigenicity than primary fused cells. The fused cells can be re-fused with the dendritic or non-dendritic parental cells as many times as desired.

Alternatively, non-dendritic cells transfected with one or more nucleic acid constructs, each of which encodes one or more identified cancer antigens or antigens from a pathogen, can be used as the non-dendritic partner in fusion. These antigens need not be expressed on the surface of the cancer cells or pathogens, so long as the antigens can be presented by a MHC class I or II molecule on the fused cells.

Methods of Using the Fusions

The invention also features: (1) methods of activating CTL and HTL using fused cells formed by fusion between DCs and non-dendritic cells; (2) CTL and HTL generated by these methods; (3) methods of treatment involving administration of these CTL and/or HTL to subjects having diseases with symptoms that can be decreased by the action of CTL and/or HTL; (4) methods of identifying antigenic peptides recognized by the CTL and/or HTL; and (5) methods of inducing an immune response in a mammal (e.g., a human patient) by administering to the mammal either antigenic peptides identified as in (4), or polypeptide antigens of which such peptides are fragments.

The fused cells of the invention can be used to stimulate the immune system of a mammal for treatment or prophylaxis of a disease. For instance, to treat a tumor (primary or metastatic) in a human, a composition containing fused cells formed by his own DCs and tumor cells can be administered to him, e.g., at a site near the lymphoid tissue. The composition may be given multiple times (e.g., three to five times) at an appropriate interval (e.g., every two to three weeks) and dosage (e.g., approximately $10^5$-$10^8$, e.g., about $0.5 \times 10^6$ to $1 \times 10^6$, fused cells per administration). For prophylaxis (i.e., vaccination) against cancer, non-syngeneic fused cells such as those formed by syngeneic DCs and allogeneic or xenogeneic cancer cells, or by allogeneic DCs and cancer cells, can be administered. To monitor the effect of vaccination, cytotoxic T lymphocytes obtained from the treated individual can be tested for their potency against cancer cells in cytotoxic assays. Multiple boosts may be needed to enhance the potency of the cytotoxic T lymphocytes. Example I below demonstrates that fusion cells formed by tumor cells and syngeneic DCs can prevent and treat tumors in animal models. Example III further demonstrates that such fusion cells may even activate anergized T cells that are specific for tumor antigens.

Compositions containing the appropriate fused cells are administered to an individual (e.g., a human) in a regimen determined as appropriate by a person skilled in the art. For example, the composition may be given multiple times (e.g., three to five times) at an appropriate interval (e. g., every two to three weeks) and dosage (e.g., approximately $10^5$-$10^8$, and preferably about $10^7$ fused cells per administration).

Fused cells generated by DCs and these transfected cells can be used for both treatment and prophylaxis of cancer or a disease caused by that pathogen. By way of example, fusion cells expressing MUC1 can be used to treat or prevent breast cancer, ovarian cancer, pancreatic cancer, prostate gland cancer, lung cancer, and myeloma; fusion cells expressing α-fetoprotein can be used to treat or prevent hepatoma or chronic hepatitis, where α-fetoprotein is often expressed at elevated levels; and fusion cells expressing prostate-specific antigen can be used to treat prostate cancer. Administration of compositions containing the fused cells so produced is as described above.

Educated T Cells

This invention also provides a population of educated, antigen-specific immune effector cells expanded in culture at the expense of hybrid cells, wherein the hybrid cells comprise antigen presenting cells (APCs) fused to cells that express one or more antigens. In one embodiment, the APC are dendritic cells (DCs) and the hybrid cells are expanded in culture. In another embodiment, the cells expressing the antigen(s) are tumor cells and the immune effector cells are cytotoxic T lymphocytes (CTLs). The DCs can be isolated from sources such as blood, skin, spleen, bone marrow or tumor. Methods for preparing the cell populations also are provided by this invention.

Any or all of the antigen-specific immune effector cells or the hybrid cells of the invention can be or have been genetically modified by the insertion of an exogenous polynucleotide. As an example, the polynucleotide introduced into the cell encodes a peptide, a ribozyme, or an antisense sequence.

The cells expressing the antigen(s) and the immune effector cells may have been enriched from a tumor. In a further embodiment, the immune effector cells are cytotoxic T lymphocytes (CTLs). The method also provides the embodiment wherein the APCs and the antigen-expressing cells are derived from the same subject or from different subjects (autologous or allogeneic).

In a further modification of this method, the immune effector cells are cultured in the presence of a cytokine, e.g., IL-2 or GM-CSF and/or a costimulatory molecule.

Methods of Making Educated T Cells

The hybrid cells used in the present invention may be formed by any suitable method known in the art. In one embodiment, a tumor biopsy sample is minced and a cell suspension created. Preferably, the cell suspension is separated into at least two fractions—one enriched for immune effector cells, e.g., T cells, and one enriched for tumor cells. Immune effector cells also can be isolated from bone marrow, blood or skin using methods well known in the art.

In general, it is desirable to isolate the initial inoculation population from neoplastic cells prior to culture. Separation of the various cell types from neoplastic cells can be performed by any number of methods, including the use of cell sorters, magnetic beads, and packed columns. Other procedures for separation can include, but are not limited to, physical separation, magnetic separation, using antibody-coated magnetic beads, affinity chromatography, cytotoxic agents joined to a monoclonal antibody or used in conjunction with a monoclonal antibody, including, but not limited to, complement and cytotoxins, and "panning" with antibody attached to a solid matrix, e.g., plate, elutriation or any other convenient technique.

The use of physical separation techniques include, but are not limited to, those based on differences in physical (density gradient centrifugation and counter-flow centrifugal elutriation), cell surface (lectin and antibody affinity), and vital staining properties (mitochondria-binding dye rho 123 and DNA-binding dye Hoechst 33342). These procedures are well known to those of skill in this art.

Monoclonal antibodies are another useful reagent for identifying markers associated with particular cell lineages and/or stages of differentiation can be used. The antibodies can be attached to a solid support to allow for crude separation. The separation techniques employed should maximize the retention of viability of the fraction to be collected. Various techniques of different efficacy can be employed to obtain "relatively crude" separations. Such separations are up to 10%, usually not more than about 5%, preferably not more than about 1%, of the total cells present not having the marker can remain with the cell population to be retained. The particular technique employed will depend upon efficiency of separation, associated cytotoxicity, ease and speed of performance, and necessity for sophisticated equipment and/or technical skill.

Another method of separating cellular fractions is to employ culture conditions, which allow for the preferential proliferation of the desired cell populations. For example, the fraction enriched for antigen expressing cells is then fused to APCs, preferably dendritic cells. Fusion between the APCs and antigen-expressing cells can be carried out with any suitable method, for example using polyethylene glycol (PEG), electrofusion, or Sendai virus. The hybrid cells are created using the PEG procedure described by Gong et al. (1997) Nat. Med 3(5):558-561, or other methods known in the art.

DCs can be obtained from bone marrow cultures, peripheral blood, spleen, or other appropriate tissue of a mammal using protocols known in the art. Bone marrow contains DC progenitors, which, upon treatment with cytokines such as granulocyte-macrophage colony-stimulating factor ("GM-CSF") and interleukin 4 ("IL-4"), proliferate and differentiate into DCs. DCs so obtained are relatively immature (as compared to, for instance, spleen DCs). These immature DCs may be more amenable to fusion than the more mature DCs found in spleen.

Peripheral blood also contains relatively immature DCs or DC progenitors, which can propagate and differentiate in the presence of appropriate cytokines such as GM-CSF and which can also be used in fusion. Alternatively, TNF is used to promote maturity of DCs.

Precommitted DCs are isolated, for example using metrizamide gradients; nonadherence/adherence techniques (Freduenthal, PS et al. (1990) PNAS 87:7698-7702); percoll gradient separations (Mehta-Damani et al (1994) J. Immunol 153:996-1003) and fluorescence-activated cell sorting techniques (Thomas et al. (1993) J. Immunol 151:6840-6852). In one embodiment, the DCs are isolated essentially as described in WO 96/23060 by FACS techniques. Although there is no specific cell surface marker for human DCs, a cocktail of 20 markers (e.g. HLA-DR, B7.2, CD 13/33, etc) are known to be present on DCs. In addition, DCs are known to lack CD3, CD20, CD56 and CD14 antigens. Therefore, combining negative and positive FACS techniques provides a method of isolating DCs.

The APCs and cells expressing one or more antigens may be autologous, i.e., derived from the same subject from which that tumor biopsy was obtained. The APCs and cells expressing the antigen may also be allogeneic, i.e., derived from a different subject, since dendritic cells are known to promote the generation of primary immune responses.

Preferably, the ratio of APCs:antigen-expressing cells is between about 1:100 and about 1000:1. Most preferably, the ration is 1:1, 5:1, or 10:1. Typically, unfused cells will die off after a few days in culture, therefore, the fused cells can be separated from the parent cells simply by allowing the culture to grow for several days. In this embodiment, the hybrid cells both survive more and, additionally, are only lightly adherent to tissue culture surfaces. The parent cells are strongly adherent to the containers. Therefore, after about 5 to 10 days in culture, the hybrid cells can be gently dislodged and transferred to new containers, while the unfused cells remained attached. Alternatively, the cell hybrids are used directly without an in vitro cell culturing step.

Alternatively, it has been shown that fused cells lack functional hypoxanthine-guanine phosphoribosyl transferase ("HGPRT") enzyme and are, therefore, resistant to treatment with the compound HAT. Accordingly, to select these cells HAT can be added to the culture media. However, unlike conventional HAT selection, hybrid cell cultures should not be exposed to the compound for more than 12 days.

Hybrid cells typically retain the phenotypic characteristics of the APCs. Thus, hybrids made with dendritic cells will express the same MHC class II proteins and other cell surface markers. Moreover, the hybrids will express those antigens expressed on the cells from which they were formed.

Expansion of Antigen-Specific Cells

The present invention makes use of these hybrid cells to stimulate production of an enriched population of antigen-specific immune effector cells. The antigen-specific immune effector cells are expanded at the expense of the hybrid cells, which die in the culture. The process by which naïve immune effector cells become educated by other cells is described essentially in Coulie (1997) Molec. Med Today 261-268.

The hybrid cells prepared as described above are mixed with naïve immune effector cells. Preferably, the immune effector cells specifically recognize tumor cells and have been enriched from the tumor biopsy sample as described above. Optionally, the cells may be cultured in the presence of a cytotokine, for example IL-2. Because DCs secrete potent immunostimulatory cytokines, such as IL-12, it may not be necessary to add supplemental cytokines during the first and successive rounds of expansion. However, if fused cells are not making IL-12, this cytokine is added to the culture. In any event, the culture conditions are such that the antigen-specific immune effector cells expand (i.e., proliferate) at a much higher rate than the hybrid cells. Multiple infusions of hybrid cells and optional cytokines can be performed to further expand the population of antigen-specific cells.

Using the hybrid cells as described, a potent antigen-specific population of immune effector cells can be obtained. These cells can be T cells that are specific for tumor-specific antigens.

Methods of Using Educated T Cells

Further provided by this invention is adoptive immunotherapy comprising administering an effective amount of the antigen-specific immune effector cells described herein, effective to induce an immune response.

Host cells containing the polynucleotides of this invention are useful for the recombinant replication of the polynucleotides and for the recombinant production of peptides. Alternatively, the cells may be used to induce an immune response in a subject in the methods described herein. When the host cells are antigen-presenting cells, they can be used to expand a population of immune effector cells such as tumor infiltrating lymphocytes which in turn are useful in adoptive immunotherapies.

An effective amount of the cells is administered to a subject to provide adoptive immunotherapy. An effective amount of cytokine or costimulatory molecule also can be coadministered to the subject.

Adoptive Immunotherapy

The expanded populations of antigen-specific immune effector cells of the present invention also find use in adoptive immunotherapy regimes and as vaccines.

Adoptive immunotherapies involve, in one aspect, administering to a subject an effective amount of a substantially pure population of educated, antigen-specific immune effector cells made by culturing naï immune effector cells with hybrid cells, wherein the hybrid cells are antigen presenting cells (APCs) fused to cells that express one or more antigens and wherein the educated, antigen-specific immune effector cells are expanded at the expense of the hybrid cells. Preferably, the APCs are DCs.

The cells can be autologous or allogeneic. In one embodiment, the adoptive immunotherapy methods described herein are autologous. In this case, the hybrid cells are made using parental cells isolated from a single subject. The expanded population also employs T cells isolated from that subject. Finally, the expanded population of antigen-specific cells is administered to the same patient.

In another embodiment, the adoptive immunotherapy methods are allogeneic or autologous. Here, cells from two or more patients are used to generate the hybrid cells, and stimulate production of the antigen-specific cells. For instance, cells from other healthy or diseased subjects can be used to generate antigen-specific cells in instances where it is not possible to obtain autologous T cells and/or dendritic cells from the subject providing the biopsy. The expanded population can be administered to any one of the subjects from whom cells were isolated, or to another subject entirely.

Antigen Discovery

Identifying Polynucleotides

Methods of transfection and identifying antigens are well known in the art. This invention also provides use of the population of antigen-specific immune effector cells prepared by the above method to further identify a polynucleotide fragment of a gene that encodes an antigen recognized by the population of antigen-specific immune effector cells. The method comprises the steps of: a) obtaining a set of polynucleotides fragments or "tags" representing gene expression in an antigen-expressing population of first cells recognized by the immune effector cells of this invention; b) obtaining a set of polynucleotides fragments or "tags" representing gene expression in a second set of cells lacking the antigen of the first cells; and c) identifying a unique tag between the polynucleotides obtained from the first and second cells, the unique tag representing a fragment of a gene that is differentially or aberrantly expressed in the population of antigen-expressing cells as compared to the second cells. In a further embodiment, the gene corresponding to the unique polynucleotide or "tag" is isolated and cloned.

The method of step, (c) (above) may, in one embodiment, be performed prior to step (b). The first and second cells are animal cells that include, but are not limited to human, murine, rat or simian cells. They can be autologous or allogeneic as defined above.

Many methods are known in the art to identify differentially expressed polynucleotides and each can be used to provide the polynucleotides in the above method. As used herein, the term "polynucleotide fragment" includes SAGE tags (defined above) as well as any other nucleic acid obtained from any methods that yield quantitative/comparative gene expression data. Such methods include, but are not limited to cDNA subtraction, differential display and expressed sequence tag methods. Techniques based on cDNA subtraction or differential display can be quite useful for comparing gene expression differences between two cell types (Hedrick et al. (1984) Nature 308:149 and Lian and Pardee (1992) Science 257:967). The expressed sequence tag (EST) approach is another valuable tool for gene discovery (Adams et al. (1991) Science 252:165 1), like Northern blotting, RNase protection, and reverse transcriptase-polymerase chain reaction (RT-PCR) analysis (Alwine et al. (1977) PNAS 74:5350; Zinn et al. (1983) Cell 34:865; and Veres et al. (1987) Science 237:415). A further method is differential display coupled with real time PCT and representational difference analysis (Lisitisyn and Wigler (1995) Meth. Enzymol 254:291-304). Another approach requires the steps of: (a) providing complementary deoxyribonucleic acid (cDNA)

polynucleotides from an antigen expressing cell recognized by the immune effector cells of this invention; (b) providing cDNA polynucleotides from cells having a compatible major histocompatability complex (MHC) to the cells of step (a) but which do not express antigen; (e) determining and analyzing the cDNAs that are aberrantly expressed by the first cells as compared to the second cells. The cDNA polynucleotides may in one embodiment, be obtained using a method identified herein as SAGE and described in U.S. Pat. No. 5,695,937.

The polynucleotides identified in steps (b) and (c) are compared to identify those polynucleotides or the polynucleotides corresponding to the genes, or fragments of the genes, that are common to the polynucleotides of the first and second cells. The common polynucleotides represent fragments of the genes that encode antigens recognized by the immune effector cells of this invention. The biological activity of the peptides encoded by the invention polynucleotides can be confirmed using methods described herein.

This method identifies polynucleotides that have the potential to encode the peptidic sequences or motifs that are antigenic or a fragment of the antigenic protein or polypeptide. Thus, the method further encompasses confirmation that the expression product encodes the antigen of interest by introducing into a cell the polynucleotide under conditions that it is expressed and presented by an APC by a compatible MHC. Methods for recognition by immune effector cells are well known in the art.

Alternatively, the genes may be identified by providing one or more immune effector cells having an identified major histocompatibility and identifying a peptide sequence motif in the antigen recognized by an immune effector cells of this invention. The polynucleotide that encodes the gene is then identified. In a further embodiment, the gene encoding the antigen that contains or comprises the peptide sequence motif is isolated and cloned. The method comprises:

(a) providing a first cell that expresses an antigen recognized by the immune effector cell of this invention and having an identified major histocompatibility complex (MHC) restriction and one or more second cells having a compatible major histocompatibility complex (MHC) to the first cell but which does not express antigen;

(b) identifying polynucleotides encoding a peptide, a sequence motif in the antigen displayed by antigen presenting cells and recognized by the immune effector cell of this invention;

(c) identifying polynucleotides which are aberrantly expressed by the first cells as compared one or more to second cells; and (d) comparing the polynucleotides identified in step (c) with the polynucleotides encoding the peptide sequence motifs identified in step (b) to identify the fragment of the gene encoding the antigen recognized by the immune effector cell of this invention. The method of step, (c) (above) may, in one embodiment, be performed prior to step (b). The first and second cells are animal cells that include, but are not limited to human, murine, rat or simian cells. They can be autologous or allogeneic.

This method identifies polynucleotides that have the potential to encode the peptide sequences or motifs that are antigenic or a fragment of the antigenic protein or polypeptide. Thus, the method further encompasses confirmation that the expression product encodes the antigen of interest by introducing into a cell the polynucleotide under conditions that it is expressed and presented by an APC by a compatible MHC. Methods for recognition by immune effector cells are provided below.

The "first cell" must satisfy two criteria: 1) it must express an antigen recognized by an immune effector cell; and 2) it must have an identified major histocompatibility complex restriction. The first and second cell populations are preselected to have compatible MHC restriction. Methods of identifying and comparing MHC are well known in the art and are described in Allen M. et al. (1994) Human Imm. 40:25-32; Santamaria P. et al. (1993) Human Imm. 37:39-50 and Haley C. K. et al. (1997) Tissue Antigens 50:401-415. Methods of determining whether the antigen is recognized by an immune effector cell are well known in the art, and include methods such as $^3$H-thymidine incorporation; metabolic activity detected by conversion of MiT to formazan blue; increased cytokine mRNA expression; increased cytokine protein production; and chromium release by target cells.

Any cell or population of cells that presents antigen recognized by immune effector cells is useful and within the scope of this invention. Such cells include, but are not limited to antigen presenting cells (defined above), cells having a purified MHC class I molecule complexed to a 132-microglobulin, dendritic cells, intact antigen presenting cells or foster antigen presenting cells. Methods for isolating and culturing these cells are well known in the art Immune effector cells recognize the APCs. Immune effector cells are prepared by the method of this invention. These methods may utilize CTLs and cells isolated from a site of viral infection, a site of autoimmune infiltration, a site of transplantation rejection, a site of inflammation, a site of lymphocyte infiltration and a site of leukocyte infiltration. Suitable CTLs include, but are not limited to polyclonal T cells isolated from one individual, polyclonal T cells isolated from two or more individuals sharing the same MHC restriction, two or more CTLs or any combination thereof. A second cell that does not express antigen can be, a foster antigen presenting cell that lacks antigen processing activity and expresses MHC molecules free of bound peptides.

After preselection of the first and second cell(s), the polynucleotides that encode a peptide sequence motif in the antigen displayed by the antigen presenting cells (the first cell population) is then identified. In one embodiment, the peptide sequence motif is first identified, from which the polynucleotide is then derived. Any of the various methods that identify peptide sequence motifs in antigens recognized by immune effector cells are useful to perform this step of the invention. Briefly, such methods include, but are not limited to the "phage method" (Scott and Smith (1990) Science 249:386-390; Cwirla et al. (1990) PNAS 87:6378-6382; and Devlin et al. (1990) Science 249:404-406), the Geysen method (Geysen et al. (1986) Molecular Immunology 23:709-715; and Geysen et al. (1987) J. Immunologic Method 102:259-274), the method of Fodor et al. (1991) Science 251:767-773), methods to test peptides that are agonists or antagonists as described in Furka et al. (1988) 14th International Congress of Biochemistry, Volume 5. Abstract FR:013; Furka, (1991) Int. J. Peptide Protein Res. 37:487-493); Houghton (U.S. Pat. No. 4,631,211 issued December 1986); and Rutter et al. (U.S. Pat. No. 5,101,175, issued Apr. 23, 1991), the method utilizing synthetic libraries (Needels et al. (1993) PNAS 90:10700-4; Ohlmeyer et at. (1993) PNAS 90:10922-10926; and Lam et al., International Patent Publication No. WO 92/00252), the method that utilizes indexed combinatorial peptide displays (Ohlmeyer et al. (1993) PNAS 90:10922-26), and the pepscan technique by Van der Zee (1989) Eur. .J. Immunol 19:43-47. In one embodiment, the method utilizes SPHERE (described in PCT WO 97135035).

Briefly, SPHERE is an empirical screening method for the identification of MHC Class I-restricted CTL epitopes that utilizes peptide libraries synthesized on a solid support (e.g., plastic beads) where each bead contains approximately 200 picomoles of a unique peptide that can be released in a controlled manner. The synthetic peptide library is tailored to a particular HLA restriction by fixing anchor residues that confer high-affinity binding to a particular HLA allele (e.g., HLA-A2) but contain a variable TCR epitope repertoire by randomizing the remaining positions. Roughly speaking, 50 96-well plates with 10,000 beads per well will accommodate a library with a complexity of approximately $5 \times 10^7$. In order to minimize both the number of CTL cells required per screen and the amount of manual manipulations, the eluted peptides can be further pooled to yield wells with any desired complexity. Based on experiments with soluble libraries, it should be possible to screen $10^7$ peptides in 96-well plates (10,000 peptides per well) with as few as $2 \times 10^6$ CTL cells. After cleaving a percentage of the peptides from the beads and incubating them with 51Cr-labeled APCs (e.g., foster antigen presenting cells or T2 cells) and the CTL line(s), peptide pools containing reactive species can be determined by measuring $^{51}$Cr-release according to standard methods known in the art. Alternatively, cytokine production (e.g., interferon-γ) or proliferation (e.g., incorporation of 3H-thymidine) assays may be used. After identifying reactive 10,000-peptide mixtures, the beads corresponding to those mixtures are separated into smaller pools and distributed to new 96-well plates (e.g., 100 beads per well). An additional percentage of peptide is released from each pool and reassayed for activity by one of the methods listed above. Upon identification of reactive 100-peptide pools, the beads corresponding those peptide mixtures are redistributed at 1 bead per well of a new 96-well plate.

Once again, an additional percentage of peptide is released and assayed for reactivity in order to isolate the single beads containing the reactive library peptides. The sequence of the peptides on individual beads can be determined by sequencing residual peptide bound to the beads by, for example, N-terminal Edman degradation or other analytical techniques known to those of skill in the art.

Degenerate polynucleotide sequences that encode the peptide motif or motifs are then determined.

As described above, an alternate embodiment further comprises identifying the gene that encodes an antigen that is specifically recognized by the immune effector cell population. Expression cloning of genes expressed in the antigen expressing cells is one means to identify the gene. In this approach (described in Kawakami Y. et al. (1994) PNAS91 (9):3515-3519) mRNA is isolated from the cells that bear a given antigen. The mRNA is converted into cDNA. The resulting cDNA fragments are inserted into plasmids or other appropriate expression vectors. The cDNA is amplified in eucaryotic (yeast, mammalian or insect cells) or procaryotic (e.g., bacteria) or another appropriate host cell. The DNA is then introduced or transfected into host cells such as COS cells (a permanent cell culture derived from African green monkey kidney cells) together with DNA encoding the appropriate HLA molecule. The tumor-specific immune effector cell clone is then added to the transfected host cells. If some of the host cells express the antigen (because they received the right cDNA), the CTL will be stimulated to produce an identifying cytokine such as IFN-γ or tumor necrosis factor (TNF), which can be detected in the culture medium. In order to screen all the mRNA molecules present in the sample cells such as tumor, approximately $10^5$ DNA containing vectors have to be tested, in pools of 100 different molecules. The pool of DNA found to be positive for T-cell stimulation can then be divided and the transfection procedure repeated until the preparation of a single species of DNA is found that can transfer the expression of the antigen.

The isolated polynucleotides and the genes corresponding to the isolated polynucleotides are also provided by this invention. As used herein, the term "polynucleotide" encompasses DNA, RNA and nucleic acid mimetics. In addition to the polynucleotides and their complements, this invention also provides the anti-sense polynucleotide stand, e.g. antisense RNA to these sequences or their complements. One can obtain an antisense RNA using the sequences provided by this invention and the methodology described in Vander Krol et at. (1988) BioTechniques 6:958.

The polynucleotides can be conjugated to a detectable marker, e.g., an enzymatic label or a radioisotope for detection of nucleic acid and/or expression of the gene in a cell. A wide variety of appropriate detectable markers are known in the art, including fluorescent, radioactive, enzymatic or other ligands, such as avidin/biotin, which are capable of giving a detectable signal. One of skill in the art can employ a fluorescent label or an enzyme tag, such as urease, alkaline phosphatase or peroxidase, instead of radioactive or other environmental undesirable reagents. In the case of enzyme tags, colorimetric indicator substrates are known which can be employed to provide a means visible to the human eye or spectrophotometrically, to identify specific hybridization with complementary nucleic acid-containing samples. Briefly, this invention further provides a method for detecting a single-stranded or its complement, by contacting target single-stranded polynucleotides with a labeled, single-stranded polynucleotide (a probe), which is at least 4, and more preferably at least 5 or 6 and most preferably at least 10 contingent nucleotides of this invention under conditions permitting hybridization (preferably moderately stringent hybridization conditions) of complementary single-stranded polynucleotides, or more preferably, under highly stringent hybridization conditions. Hybridized polynucleotide pairs are separated from un-hybridized, single-stranded polynucleotides. The hybridized polynucleotide pairs are detected using methods well known to those of skill in the art and set forth, for example, in Sambrook et al. (1989) supra. The polynucleotides can be provided in kits with appropriate reagents and instructions for their use as probes or primers.

The polynucleotides of this invention can be replicated using PCR. PCR technology is the subject matter of U.S. Pat. Nos. 4,683,195; 4,800,159; 4,754,065; and 4,683,202 and described in PCR: THE POLYMERASE CHAIN REACTION (Mullis et al. eds, Birkhauser Press, Boston (1994)) and references cited therein.

Alternatively, one of skill in the art can use the sequences provided herein and a commercial DNA synthesizer to replicate the DNA. Accordingly, this invention also provides a process for obtaining the polynucleotides of this invention by providing the linear sequence of the polynucleotide, appropriate primer molecules, chemicals such as enzymes and instructions for their replication and chemically replicating or linking the nucleotides in the proper orientation to obtain the polynucleotides. In a separate embodiment, these polynucleotides are further isolated. Still further, one of skill in the art can insert the polynucleotide into a suitable replication vector and insert the vector into a suitable host cell (procaryotic or eucaryotic) for replication and amplification. The DNA so amplified can be isolated from the cell by methods well known to those of skill in the art. A process for obtaining polynucleotides by this method is further provided herein as well as the polynucleotides so obtained.

RNA can be obtained by first inserting a DNA polynucleotide into a suitable host cell. The DNA can be inserted by any appropriate method, e.g., by the use of an appropriate gene delivery vehicle (e.g., liposome, plasmid or vector) or by electroporation. When the cell replicates and the DNA is transcribed into RNA; the RNA can then be isolated using methods well known to those of skill in the art, for example, as set forth in Sambrook et al. (1989) supra. For instance, mRNA can be isolated using various lytic enzymes or chemical solutions according to the procedures set forth in Sambrook et al. (1989) supra or extracted by nucleic acid-binding resins following the accompanying instructions provided by manufactures.

Method of Screening Candidate Peptide and Peptides for Antigenic Activity

The CTL and HTL ("effector cells") described above can be used to identify antigens expressed by the non-dendritic cell partners of the fused cells used to generate the effector cells of the invention, by a number of methods used in the art. In brief, the effector cell-containing cell population is cultured together with a candidate peptide or polypeptide and either an appropriate target cell (where cytotoxicity is assayed) or antigen presenting cell (APC) (where cell proliferation, or cytokine production is assayed) and the relevant activity is determined. A peptide that induces effector activity will be an antigenic peptide, which is recognized by the effector cells. A polypeptide that induces effector activity will be an antigenic polypeptide, a peptide fragment of which is recognized by the effector cells.

Cytotoxic activity can be tested by a variety of methods known in the art (e.g., $^{51}$Cr or lactate dehydogenase (LDH) release assays described in Examples I and III-V). Target cells can be any of a variety of cell types, e.g., fibroblasts, lymphocytes, lectin (e.g., phytohemagglutinin (PHA), concanavalin A (ConA), or lipopolysaccharide (LPS)) activated lymphocyte blasts, macrophages, monocytes, or tumor cell lines. The target cells should not naturally express the candidate antigens being tested for antigenic activity, though they could express them recombinantly. The target cells should, however, express at least one type of MEC class I molecule or MHC class II molecule (depending on the restriction of the relevant CTL), in common with the CTL. The target cells can endogenously express an appropriate MHC molecule or they can express transfected polynucleotides encoding such molecules. The chosen target cell population can be pulsed with the candidate peptide or polypeptide prior to the assay or the candidate peptide or polypeptide can be added to the assay vessel, e.g., a microtiter plate well or a culture tube, together with the CTL and target cells. Alternatively, target cells transfected or transformed with an expression vector containing a sequence encoding the candidate peptide or polypeptide can be used. The CTL-containing cell population, the target cells, and the candidate peptide or polypeptide are cultured together for about 4 to about 24 hours. Lysis of the target cells is measured by, for example, release of $^{51}$Cr or LDH from the target cells. A peptide that elicits lysis of the target cells by the CTL is an antigenic peptide that is recognized by the CTL. A polypeptide that elicits lysis of the target cells by the CTL is an antigenic polypeptide, a peptide fragment of which is recognized by the CTL.

Candidate peptides or polypeptides can be tested for their ability to induce proliferative responses in both CTL and HTL. The effector cells are cultured together with a candidate peptide or polypeptide in the presence of APC expressing an appropriate MHC class I or class II molecule. Such APC can be B-lymphocytes, monocytes, macrophages, or dendritic cells, or whole PBMC. APC can also be immortalized cell lines derived from B-lymphocytes, monocytes, macrophages, or dendritic cells. The APC can endogenously express an appropriate MEC molecule or they can express a transfected expression vector encoding such a molecule. In all cases, the APC can, prior to the assay, be rendered non-proliferative by treatment with, e.g., ionizing radiation or mitomycin-C. The effector cell-containing population is cultured with and without a candidate peptide or polypeptide and the cells' proliferative responses are measured by, e.g., incorporation of [$^3$H]-thymidine into their DNA.

As an alternative to measuring cell proliferation, cytokine production by the effector cells can be measured by procedures known to those in art. Cytokines include, without limitation, interleukin-2 (IL-2), IFN-, IL-4, IL-5, TNF-, interleukin-3 (IL-3), interleukin-6 (IL-6), interleukin-10 (IL-b), interleukin-12 (IL-12), interleukin-15 (IL-15) and transforming growth factor (TGF) and assays to measure them include, without limitation, ELISA, and bio-assays in which cells responsive to the relevant cytokine are tested for responsiveness (e.g., proliferation) in the presence of a test sample. Alternatively, cytokine production by effector cells can be directly visualized by intracellular immunofluorescence staining and flow cytometry.

Choice of candidate peptides and polypeptides to be tested for antigenicity will depend on the non-dendritic cells that were used to make the fused cells. Where the non-dendritic cells are tumor cells, candidate polypeptides will be those expressed by the relevant tumor cells. They will preferably be those expressed at a significantly higher level in the tumor cells than in the normal cell equivalent of the tumor cells. Candidate peptides will be fragments of such polypeptides. Thus, for example, for melanoma cells, the candidate polypeptide could be tyrosinase or a member of the MART family of molecules; for colon cancer, carcinoembryonic antigen; for prostate cancer, prostate specific antigen; for breast or ovarian cancer, HER2/neu; for ovarian cancer, CA-125; or for most carcinomas, mucin-1 (MUC1).

On the other hand, where the non-dendritic cells used to generate the fused cells were infected cells or cells genetically engineered to express a pathogen-derived polypeptide, the candidate polypeptide will be one expressed by the appropriate infectious microorganism or that expressed by the transfected cells, respectively. Examples of such polypeptides include retroviral (e.g., HIV or HTLV) membrane glycoproteins (e.g., gp160) or gag proteins, influenza virus neuraminidase or hemagglutinin, *Mycobacterium tuberculosis* or *leprae* proteins, or protozoan (e.g., *Plasmodium* or *Trypanosoma*) proteins. Polypeptides can also be from other microorganisms listed herein. Peptides to be tested can be, for example, a series of peptides representing various segments of a full-length polypeptide of interest, e.g., peptides with overlapping sequences that, in tow, cover the whole sequence. Peptides to be tested can be any length. When testing MHC class I restricted responses of effector cells, they will preferably be 7-20 (e.g., 8-12) amino acids in length. On the other hand, in MHC class II restricted responses, the peptides will preferably be 10-30 (e.g., 12-25) amino acids in length.

Alternatively, a random library of peptides can be tested. By comparing the sequences of those eliciting positive responses in the appropriate effector cells to a protein sequence database, polypeptides containing the peptide sequence can be identified. Relevant polypeptides or the identified peptides themselves would be candidate therapeutic or vaccine agents for corresponding diseases (see below).

Polypeptides and peptides can be made by a variety of means known in the art. Smaller peptides (less than 50 amino acids long) can be conveniently synthesized by standard chemical means. In addition, both polypeptides and peptides can be produced by standard in vitro recombinant DNA techniques, and in vivo genetic recombination (e.g., transgenesis), using nucleotide sequences encoding the appropriate polypeptides or peptides. Methods well known to those skilled in the art can be used to construct expression vectors containing relevant coding sequences and appropriate transcriptional/translational control signals. See, for example, the techniques described in Maniatis et al., Molecular Cloning: A Laboratory Manual [Cold Spring Harbor Laboratory, N.Y., 1989), and Ausubel et al., Current Protocols in Molecular Biology, [Green Publishing Associates and Wiley Interscience, N.Y., 1989).

A variety of host-expression vector systems can be used to express the peptides and polypeptides. Such host-expression systems represent vehicles by which the polypeptides of interest can be produced and subsequently purified, but also represent cells that can, when transformed or transfected with the appropriate nucleotide coding sequences, produce the relevant peptide or polypeptide in situ. These include, but are not limited to, microorganisms such as bacteria, e.g., *E. coli* or *B. subtilis*, transformed with recombinant bacteriophage DNA, plasmid or cosmid DNA expression vectors containing peptide or polypeptide coding sequences; yeast, e.g., *Saccharomyces* or *Pichia*, transformed with recombinant yeast expression vectors containing the appropriate coding sequences; insect cell systems infected with recombinant virus expression vectors, e.g., baculovirus; plant cell systems infected with recombinant virus expression vectors, e.g., cauliflower mosaic virus (CaMV) or tobacco mosaic virus (TMV), or transformed with recombinant plasmid expression vectors, e.g., Ti plasmids, containing the appropriate coding sequences; or mammalian cell systems, e.g., COS, CHO, BHK, 293 or 3T3, harboring recombinant expression constructs containing promoters derived from the genome of mammalian cells, e.g., metallothionein promoter, or from mammalian viruses, e.g., the adenovirus late promoter or the vaccinia virus 7.5K promoter.

Peptides of the invention include those described above, but modified for in vivo use by the addition, at either or both the amino- and carboxyl-terminal ends, of a blocking agent to facilitate survival of the relevant peptide in vivo. This can be useful in those situations in which the peptide termini tend to be degraded by proteases prior to cellular or mitochondrial uptake. Such blocking agents can include, without limitation, additional related or unrelated peptide sequences that can be attached to the amino and/or carboxyl terminal residues of the peptide to be administered. This can be done either chemically during the synthesis of the peptide or by recombinant DNA technology by methods familiar to artisans of average skill. Alternatively, blocking agents such as pyroglutamic acid or other molecules known in the art can be attached to the amino and/or carboxyl terminal residues, or the amino group at the amino terminus or carboxyl group at the carboxyl terminus can be replaced with a different moiety. Likewise, the peptides can be covalently or noncovalently coupled to pharmaceutically acceptable "carrier" proteins prior to administration.

Also of interest are peptidomimetic compounds that are designed based upon the amino acid sequences of the peptides or polypeptides. Peptidomimetic compounds are synthetic compounds having a three-dimensional conformation (i.e., a "peptide motif") that is substantially the same as the three-dimensional conformation of a selected peptide. The peptide motif provides the peptidomimetic compound with the ability to activate T cells in a manner qualitatively identical to that of the peptide or polypeptide from which the peptidomimetic was derived. Peptidomimetic compounds can have additional characteristics that enhance their therapeutic utility, such as increased cell permeability and prolonged biological half-life.

The peptidomimetics typically have a backbone that is partially or completely non-peptide, but with side groups that are identical to the side groups of the amino acid residues that occur in the peptide on which the peptidomimetic is based. Several types of chemical bonds, e.g., ester, thioester, thioamide, retroamide, reduced carbonyl, dimethylene and ketomethylene bonds, are known in the art to be generally useful substitutes for peptide bonds in the construction of protease-resistant peptidomimetics.

Methods Using the Effector Cells, Polypeptides, and Peptides of the Invention

The effector cells (CTL and HTL), polypeptides, and peptides of the invention can be used in basic research studies of tumor and infection immunology. They can be used in studies, for example, to further elucidate the mechanisms of antigen processing, antigen presentation, antigen recognition, signal transduction in CTL and HTL, and HTL-CTL interactions. In addition to other uses, they can be used as positive or negative controls in appropriate assays. They could also be used for diagnosis. For example, the ability of T cells from a test subject to respond to a polypeptide or peptide of the invention would be an indication that the test subject has or is susceptible to a disease associated with expression of the relevant peptide or polypeptide. CTL and HTL of the invention would be valuable "positive controls" for an appropriate diagnostic assay. Furthermore, the effector cells, polypeptides, and peptides can be used in methods of therapy and vaccination. These methods of the invention fall into 2 basic classes, i.e., those using in vivo approaches and those using ex vivo approaches.

In Vivo Approaches

In one in vivo approach, a polypeptide, peptide or peptidomimetic is administered to a subject by any of the routes listed above. It is preferably delivered directly to an appropriate lymphoid tissue (e.g. spleen, lymph node, or mucosal-associated lymphoid tissue (MALT)). The subject can have or be suspected of having any of the diseases disclosed herein. The immune response generated in the subject by administration of the polypeptide, peptide or peptidomimetic can either completely abrogate of decrease the symptoms of the disease. Alternatively, the polypeptide, peptide or peptidomimetic can be administered to a subject as a vaccine, i.e., with the object of preventing or delaying onset of a relevant disease.

The dosage required depends on the choice of polypeptide, peptide or peptidomimetic, the route of administration, the nature of the formulation, the nature of the patient's illness, and the judgment of the attending physician. Suitable dosages are in the range of 0.1-100.0 g/kg. Wide variations in the needed dosage are to be expected in view of the variety of polypeptides, peptides, or peptidomimetics of the invention available and the differing efficiencies of various routes of administration. For example, oral administration would be expected to require higher dosages than administration by i.v. injection. Variations in these dosage levels can be adjusted using standard empirical routines for optimization as is well understood in the art.

Ex Vivo Approaches

In one ex vivo approach, populations of cells containing effector cells (CTL and/or HTL generated as described above using the fused cells of the invention) can be administered to a subject having or suspected of having any of the diseases described herein. The lymphoid cells used to generate the effector cells can have been obtained from the subject or a second subject, preferably of the same species, more preferably with no or a single MHC locus (class I or class II) incompatibility with the first subject. For example, donor lymphocyte infusion (DLI), in which allogeneic cells (e.g., PBMC) containing T lymphocytes are infused into a subject, has been shown to decrease tumor load or even result in full remission in a variety of cancers. The therapeutic activity has been attributed to graft-versus-tumor activity of donor T-cells activated by MHC and/or non-MHC alloantigens of the recipient subject. The effector function of the cells used for DLI can be enhanced by exposing them (singly or multiply) (e.g., in vitro) to appropriate fused cells of the invention prior to infusion into the recipient subject. Preferably, but not necessarily, the fused cells will have been generated from dendritic cells and non-dendritic cells from the recipient subject. DLI is usually, but not necessarily, performed after nonmyeloablative bone marrow transplantation. DLI and non-myeloablative bone marrow transplantation methodologies are known in the art.

In a second ex vivo approach, lymphoid cells are isolated from the subject, or another subject; and are exposed (e.g., in vitro) to a polypeptide or peptide identified by the method of the invention in the presence of appropriate APC. The lymphoid cells can be exposed once or multiply (e.g., 2, 3, 4, 6, 8, or 10 times). The cytolytic, proliferative, or cytokine-producing ability of the stimulated lymphoid cells can be monitored after one or more exposures. Once the desired level of effector activity is attained, the cells can be introduced into the subject via any of the routes listed herein. Naturally, cells to be used for DLI could, instead of being activated by the fused cells of the invention, be activated by the peptides or polypeptides identified as described above.

In any of therapeutic or prophylactic methods of the invention, administration of cells, polypeptides, peptides, or peptidomimmetic can be accompanied by administration of any of the immunoregulatory cytokines (e.g., IL-2) disclosed herein.

The therapeutic or prophylatic methods of the invention can be applied to any of the diseases and species listed herein. Methods to test whether a peptide or polypeptide is therapeutic for or prophylactic against a particular disease are known in the art. Where a therapeutic effect is being tested, a test population displaying symptoms of the disease (e.g., cancer patients or experimental animals with cancer) is treated with a test effector cell-containing cell population, peptide, or polypeptide, using any of the above described strategies. A control population, also displaying symptoms of the disease, is treated, using the same methodology, with a placebo.

Disappearance or a decrease of the disease symptoms in the test subjects would indicate that the polypeptide or peptide was an effective therapeutic agent.

By applying the same strategies to subjects prior to onset of disease symptoms (e.g., human or experimental subjects with a genetic predisposition to the disease), effector cell-containing cell populations, polypeptides or peptides of the invention can be tested for efficacy in inducing immune responses or as prophylactic agents, i.e., vaccines. In this situation, prevention of or delay in onset of disease symptoms is tested. Alternatively, the levels of immune responses induced in the experimental arid control groups can be compared.

Methods of Using the Polynucleotides of the Invention

The polynucleotides can be used as probes or primers. Host cells containing polynucleotides of this invention also are within the scope of this invention. It is known in the art that a "perfectly matched" probe is not needed for a specific hybridization. Minor changes in probe sequence achieved by substitution, deletion or insertion of a small number of bases do not affect the hybridization specificity. In general, as much as 20% base-pair mismatch (when optimally aligned) can be tolerated. Preferably, a probe useful for detecting the aforementioned mRNA is at least about 80% identical to the homologous region of comparable size contained in the polynucleotides of this invention. More preferably, the probe is 85% identical to the corresponding gene sequence after alignment of the homologous region; even more preferably, it exhibits 90% identity.

These probes can be used in radioassays (e.g. Southern and Northern blot analysis) to detect or monitor various cells or tissue containing these cells. The probes also can be attached to a solid support or an array such as a chip for use in high throughput screening assays for the detection of expression of the gene corresponding to one or more polynucleotide(s) of this invention. Accordingly, this invention also provides at least one probe as defined above of the transcripts or the complement of one of these sequences, attached to a solid support such as a chip for use in high throughput screens.

In a further embodiment, the polynucleotide or gene sequence can also be compared to a sequence database, for example, using a computer method to match a sample sequence with known sequences. Sequence identity can be determined by a sequence comparison using, i.e., sequence alignment programs that are known in the art, such as those described in CURRENT PROTOCOLS IN MOLECULAR BIOLOGY (F. M. Ausubel et al., eds., 1987) Supplement 30, section 7.7.18, Table 7.7.1. A preferred alignment program is ALIGN Plus (Scientific and Educational Software, Pennsylvania), preferably using default parameters, which are as follows: mismatch=2; open gap=0; and extend gap=2. Another preferred program is the BLAST program for alignment of two nucleotide sequences, using default parameters as follows: open gap=50; extension gap=2 penalties; gap× dropoff=0; expect=10; word size=11. The BLAST program is available at the following Internet address: http://www.ncbi.nim.nih.gov. As noted above, alternatively, hybridization under conditions of high, moderate and low stringency can also indicate degree of sequence identity.

The polynucleotides of the present invention also can serve as primers for the detection of genes or gene transcripts that are expressed in APC, for example, to confirm transduction of the polynucleotides into host cells. In this context, amplification means any method employing a primer-dependent polymerase capable of replicating a target sequence with reasonable fidelity. Amplification may be carried out by natural or recombinant DNA-polymerases such as T7 DNA polymerase, Klenow fragment of *E.coli* DNA polymerase, and reverse transcriptase. A preferred length of the primer is the same as that identified for probes, above.

The invention further provides the isolated polynucleotide operatively linked to a promoter of RNA transcription, as well as other regulatory sequences for replication and/or transient or stable expression of the DNA or RNA. As used herein, the term "operatively linked" means positioned in such a manner that the promoter will direct transcription of RNA off the DNA molecule. Examples of such promoters are SP6, T4 and T7. In certain embodiments, cell-specific promoters are used for cell-specific expression of the inserted polynucleotide. Vectors which contain a promoter or a promoter/enhancer, with termination codons and selectable marker sequences, as well as a cloning site into which an inserted piece of DNA can be operatively linked to that promoter are well known, in the art and commercially available. For general methodology and cloning strategies, see GENE EXPRESSION TECHNOLOGY (Goeddel ed., Academic Press, Inc. (1991)) and references cited therein and VECTORS: ESSENTIAL DATA SERIES (Gaeesa and Ramji, eds., John Wiley & Sons, N.Y. (1994)), which contains maps, functional properties, commercial suppliers and a reference to GenEMBL accession numbers for various suitable vectors. Preferable, these vectors are capable of transcribing RNA in vitro or in vivo.

Expression vectors containing these nucleic acids are useful to obtain host vector systems to produce proteins and polypeptides. It is implied that these expression vectors must be replicable in the host organisms either as episomes or as an integral part of the chromosomal DNA. Suitable expression vectors include plasmids, viral vectors, including adenoviruses, adeno-associated viruses, retroviruses, cosmids, etc. Adenoviral vectors are particularly useful for introducing genes into tissues in vivo because of their high levels of expression and efficient transformation of cells both in vitro and in vivo. When a nucleic acid is inserted into a suitable host cell, e.g., a procaryotic or a eucaryotic cell and the host cell replicates, the protein can be recombinantly produced. Suitable host cells will depend on the vector and can include mammalian cells, animal cells, human cells, simian cells, insect cells, yeast cells, and bacterial cells constructed using well known methods. See Sambrook et al. (1989) supra. In addition to the use of viral vector for insertion of exogenous nucleic acid into cells, the nucleic acid can be inserted into the host cell by methods well known in the art such as transformation for bacterial cells; transfection using calcium phosphate precipitation for mammalian cells; or DEAE-dextran; electroporation; or microinjection. See Sambrook et al. (1989) supra for this methodology. Thus, this invention also provides a host cell, e.g. a mammalian cell, an animal cell (rat or mouse), a human cell, or a procaryotic cell such as a bacterial cell, containing a polynucleotide encoding a protein or polypeptide or antibody.

When the vectors are used for gene therapy in vivo or ex vivo, a pharmaceutically acceptable vector is preferred, such as a replication-incompetent, retroviral or adenoviral vector. Pharmaceutically acceptable vectors containing the nucleic acids of this invention can be further modified for transient or stable expression of the inserted polynucleotide. As used herein, the term "pharmaceutically acceptable vector" includes, but is not limited to, a vector or delivery vehicle having the ability to selectively target and introduce the nucleic acid into dividing cells. An example of such a vector is a "replication incompetent" vector defined by its inability to produce viral proteins, precluding spread of the vector in the infected host cell. An example of a replication-incompetent retroviral vector is LNL6 (Miller, A. D. et al. (1989) BioTechniques 7:980-990). The methodology of using replication-incompetent retroviruses for retroviral-mediated gene transfer of gene markers is well established (Correll et al. (1989) PNAS86:8912; Bordignon (1989) PNASS6:8912-52; Culver K. (1991) PNAS 88:3155; and Rill D. R. (1991) Blood 79(1O):2694-700.

The methods of this invention are used to also monitor expression of the genes, which specifically hybridize to the probes of this invention in response to defined stimuli, such as a drug.

The hybridized nucleic acids are detected by detecting one or more labels attached to the sample nucleic acids. The labels may be incorporated by any of a number of means well known to those of skill in the art. However, in one aspect, the label is simultaneously incorporated during the amplification step in the preparation of the sample nucleic acid. Thus, for example, polymerase chain reaction (PCR) with labeled primers or labeled nucleotides will provide a labeled amplification product. In a separate embodiment, transcription amplification, as described above, using a labeled nucleotide (e.g. fluorescein-labeled UTP and/or CTP) incorporates a label in to the transcribed nucleic acids.

Alternatively, a label may be added directly to the original nucleic acid sample (e.g., mRNA, polyA, mRNA, cDNA, etc.) or to the amplification product after the amplification is completed. Means of attaching labels to nucleic acids are well known to those of skill in the art and include, for example nick translation or end-labeling (e.g. with a labeled RNA) by kinasing of the nucleic acid and subsequent attachment (ligation) of a nucleic acid linker joining the sample nucleic acid to a label (e.g., a fluorophore).

The polynucleotide also can be modified prior to hybridization to a high density probe array in order to reduce sample complexity thereby decreasing background signal and improving sensitivity of the measurement using the methods disclosed in WO 97/103 65. They also can be attached to a chip for use in diagnostic and analytical assays. Results from the chip assay are typically analyzed using a computer software program. See, for example, EP 0717 113 A2 and WO 95/2068 1. The hybridization data is read into the program, which calculates the expression level of the targeted gene(s). This figure is compared against existing data sets of gene expression levels for diseased and healthy individuals.

Also provided by this invention are antibodies that specifically react with the peptides and proteins of this invention. Such antibodies include, but are not limited to polyclonal antibodies, monoclonal antibodies, chimeric antibodies, humanized antibodies and antibody fragments. These can be combined with detectable labels and used to identify antigens and fragments thereof using well-known methods. Alternatively, they can be combined with pharmaceutically acceptable carriers and administered therapeutically to a subject in need of such treatment kits containing the antibodies, reagents and instructions for use are further provided by this invention.

Thus, it should be understood, although not always explicitly stated, that the compositions of this invention can be combined with a pharmaceutically acceptable carrier prior to administration or combined with a carrier for in vitro use. These in vitro carriers, include, but are not limited, beads for use in cell separation methodologies.

Genetic Modifications

The methods of this invention are intended to encompass any method of gene transfer into either the hybrid cells or the antigen-specific population of cells derived using the hybrid cells as stimulators. Examples of genetic modifications includes, but are not limited to viral mediated gene transfer, liposome mediated transfer, transformation, transfection and transduction, e.g., viral mediated gene transfer such as the use of vectors based on DNA viruses such as adenovirus, adeno-associated virus and herpes virus, as well as retroviral based vectors. The methods are particularly suited for the integration of a nucleic acid contained in a vector or construct lacking a nuclear localizing element or sequence such that the nucleic acid remains in the cytoplasm. In these instances, the nucleic acid or therapeutic gene is able to enter the nucleus during M (mitosis) phase when the nuclear membrane breaks down and the nucleic acid or therapeutic gene gains access to the host cell chromosome. Genetic modification is performed ex vivo and the modified (i.e. transduced) cells are subsequently administered to the recipient. Thus, the invention encompasses treatment of diseases amenable to gene transfer into antigen-specific cells, by administering the gene ex vivo or in vivo by the methods disclosed herein.

The expanded population of antigen-specific cells can be genetically modified. In addition, the hybrid cells can also be genetically modified, for example, to supply particular secreted products including, but not limited to, hormones, enzymes, interferons, growth factors, or the like. By employing an appropriate regulatory initiation region, inducible production of the deficient protein can be achieved, so that production of the protein will parallel natural production, even though production will be in a different cell type from the cell type that normally produces such protein. It is also possible to insert a ribozyme, antisense or other message to inhibit particular gene products or susceptibility to diseases, particularly hematolymphotropic diseases.

Suitable expression and transfer vectors have been described above.

Therapeutic genes that encode dominant inhibitory oligonucleotides and peptides as well as genes that encode regulatory proteins and oligonucleotides also are encompassed by this invention. Generally, gene therapy will involve the transfer of a single therapeutic gene although more than one gene may be necessary for the treatment of particular diseases. The therapeutic gene is a dominant inhibiting mutant of the wild-type immunosuppressive agent. Alternatively, the therapeutic gene could be a wild-type, copy of a defective gene or a functional homolog.

More than one gene can be administered per vector or alternatively, more than one gene can be delivered using several compatible vectors. Depending on the genetic defect, the therapeutic gene can include the regulatory and untranslated sequences. For gene therapy in human patients, the therapeutic gene will generally be of human origin although genes from other closely related species that exhibit high homology and biologically identical or equivalent function in humans may be used, if the gene product does not induce an adverse immune reaction in the recipient. The therapeutic gene suitable for use in treatment will vary with the disease.

A marker gene can be included in the vector for the purpose of monitoring successful transduction and for selection of cells into which the DNA has been integrated, as against cells, which have not integrated the DNA construct. Various marker genes include, but are not limited to, antibiotic resistance markers, such as resistance to 0418 or hygromycin. Less conveniently, negative selection may be used, including, but not limited to, where the marker is the HSV-tk gene, which will make the cells sensitive to agents such as acyclovir and gancyclovir. Alternatively, selections could be accomplished by employment of a stable cell surface marker to select for transgene expressing cells by FACS sorting. The NeoR (neomycin/0418 resistance) gene is commonly used but any convenient marker gene whose sequences are not already present in the recipient cell, can be used.

The viral vector can be modified to incorporate chimeric envelope proteins or nonviral membrane proteins into retroviral particles to improve particle stability and expand the host range or to permit cell type-specific targeting during infection. The production of retroviral vectors that have altered host range is taught, for example, in WO 92/1 4829 and WO 93/14188. Retroviral vectors that can target specific cell types in vivo are also taught, for example, in Kasahara et al. (1994) Science 266:1373-1376. Kasahara et al. describe the construction of a Moloney leukemia virus (MOMLV) having a chimeric envelope protein consisting of human erythropoietin (EPO) fused with the viral envelope protein. This hybrid virus shows tissue tropism for human red blood progenitor cells that bear the receptor for EPO, and is therefore useful in gene therapy of sickle cell anemia and thalassemia. Retroviral vectors capable of specifically targeting infection of cells are preferred for in vivo gene therapy.

Expression of the transferred gene can be controlled in a variety of ways depending on the purpose of gene transfer and the desired effect. Thus, the introduced gene may be put under the control of a promoter that will cause the gene to be expressed constitutively, only under specific physiologic conditions, or in particular cell types.

Examples of promoters that may be used to cause expression of the introduced sequence in specific cell types include Granzyme A for expression in T-cells and NK cells, the CD34 promoter for expression in stem and progenitor cells, the CD8 promoter for expression in cytotoxic T-cells, and the CD11b promoter for expression in myeloid cells.

Inducible promoters may be used for gene expression under certain physiologic conditions. For example, an electrophile response element may be used to induce expression of a chemoresistance gene in response to electrophilic molecules. The therapeutic benefit may be further increased by targeting the gene product to the appropriate cellular location, for example the nucleus, by attaching the appropriate localizing sequences.

After viral transduction, the presence of the viral vector in the transduced cells or their progeny can be verified such as by PCR. PCR can be performed to detect the marker gene or other virally transduced sequences. Generally, periodic blood samples are taken and PCR conveniently performed using e.g. NeoR probes if the NeoR gene is used as marker. The presence of virally transduced sequences in bone marrow cells or mature hematopoietic cells is evidence of successful reconstitution by the transduced cells. PCR techniques and reagents are well known in the art, See, generally, PCR PROTOCOLS, A GUIDE TO METHODS AND APPLICATIONS. Innis, Gelfand, Sninsky & White, eds. (Academic Press, Inc., San Diego, 1990) and commercially available (Perkin-Elmer).

Vaccines

The populations and methods described herein can also be used to develop cell-based vaccines. Further provided by this invention are vaccines comprising antigen-specific immune effector cells according to the present invention. Still further provided by this invention is a vaccine comprising an antigen or a fragment thereof such as an epitope or sequence motif utilizing the antigen specific immune effector cells described herein. Methods of administering vaccines are known in the art and the vaccines may be combined with an acceptable pharmaceutical carrier. An effective amount of a cytokine and/or costimulatory molecule also can be administered.

The polynucleotides, genes and encoded peptides and proteins according to the invention can be further cloned and expressed in vitro or in vivo. The proteins and polypeptides produced and isolated from the host cell expression systems are also within the scope of this invention. Expression and cloning vectors as well as host cells containing these polynucleotides and genes are claimed herein as well as methods of administering them to a subject in an effective amount. Peptides corresponding to these sequences can be generated by recombinant technology and they may be administered to a subject as a vaccine or alternatively, introduced into APC which in turn, are administered in an effective amount to a subject. The genes may be used to produce proteins which in turn may be used to pulse APC. The APC may in turn be used to expand immune effector cells such as CTLs. The pulsed APC and expanded effector cells can be used for immunotherapy by administering an effective amount of the composition to a subject.

Antigen Identification

The populations described herein can also be used to identify novel antigens and the genes encoding these antigens using a variety of methods, such as that described in PCT WO 97/35035. In another embodiment, a SAGE analysis (described in U.S. Pat. No. 5,695,937) can be employed to identify the antigens recognized by the expanded populations. SAGE analysis involves identifying nucleotide sequences aberrantly or differentially expressed in the antigen-expressing cells. Briefly, SAGE analysis begins with providing complementary deoxyribonucleic acid (cDNA) from (1) the antigen-expressing population and (2) cells not expressing that antigen. Both cDNAs can be linked to primer sites. Sequence tags are then created, for example, using the appropriate primers to amplify the DNA. By measuring the differences in these tags between the two cell types, sequences which are aberrantly expressed in the antigen-expressing cell population can be identified.

Alternatively, mass-spectrophotometric analysis of the peptides eluted from the tumor cell:MHC complexes can be used. Other techniques of identifying antigens will be known to those of skill in the art.

The following examples are meant to illustrate, but not limit, the compositions and methods of the invention.

EXAMPLE I

Fusion of Mouse Dendritic Cells and Non-Dendritic Cells

Cell Culture and Fusion

Murine (C57BL/6) MC38 adenocarcinoma cells were stably transfected with the DF3/MUC1 cDNA to generate the MC38/MUC1 cell line (Siddiqui et al., Proc. Natl. Acad. Sci. USA 85:2320-2323, 1988; Akagi et al., J. Immunother. 20:38-47, 1997). MC38, MC38/MUC1 and the syngeneic MB49 bladder cancer cells were maintained in DMEM supplemented with 10% heat-inactivated fetal calf serum ("FCS"), 2 mM glutamine, 100 U/ml penicillin and 100 µ/ml streptomycin.

DCs were obtained from bone marrow culture using a method described by Inaba et al. (J. Exp. Med. 176: 1693-1702, 1992) with modifications. In brief, bone marrow was flushed from long bones, and red cells were lysed with ammonium chloride. Lymphocytes, granulocytes, and Ia$^+$ cells were depleted from the bone marrow cells by incubation with the following monoclonal antibodies ("mAb"s):

(1) 2.43, anti-CD8 [TIB 210; American Type Culture Collection (ATCC), Rockville, Md.];
(2) GK1.5, anti-CD4 (TIB 207, ATCC);
(3) RA3-3A1/6.1, anti B220/CD45R (TIB 146, ATCC);
(4) B21-2, anti-Ia (TIB 229, ATCC); and
(5) RB6-8C5, anti-Gr-1 (Pharmingen, San Diego, Calif.);

and then complement. The unlysed cells were plated in six-well culture plates in RPMI 1640 medium supplemented with 5% heat-inactivated FCS, 50 µM 2-mercaptoethanol, 1 mM HEPES (pH 7.4), 2 mM glutamine, 10 U/ml penicillin, 10 µg/ml streptomycin and 500 U/ml recombinant murine GM-CSF (Boehringer Mannheim, Indiana). At day 7 of culture, nonadherent and loosely adherent cells were collected and replated in 100-mm petri dishes ($10^6$ cells/ml; 8 ml/dish). The nonadherent cells were washed away after 30 min of incubation and RPMI medium containing GM-CSF was added to the adherent cells. After 18 hours in culture, the nonadherent cell population was removed for fusion with MC38/MUC1 cells or MC38.

Fusion was carried out by incubating cells with 50% PEG in Dulbecco's phosphate buffered saline ("PBS") without $Ca^{2+}$ or $Mg^{2+}$ at pH 7.4. The ratio of DCs to tumor cells in the fusion was from 15:1 to 20:1. After fusion, the cells were plated in 24-well culture plates in a medium containing HAT (Sigma) for 10-14 days. Because MC38 cells are not very sensitive to HAT, HAT was used to slow the proliferation of, rather than kill, MC38/MUC1 and MC38 cells. MC38/MUC1 and MC38 cells grow firmly attached to the tissue culture flask, while the fused cells were dislodged by gentle pipetting.

Flow Cytometry

Cells were washed with PBS and incubated with mAb DF3 (anti-MUC1), mAb M1/42/3.9.8 (anti-MHC class I), mAb M5/114 (anti-MHC class II), mAb 16-10A1 (anti-B7-1), mAb GL1 (anti-B7-2) and MAb $3E^2$ (anti-ICAM-1) for 30 min on ice. After washing with PBS, fluorescein isothiocyanate ("FITC")-conjugated anti-hamster, -rat and -mouse IgG was added for another 30 min on ice. Samples were then washed, fixed and analyzed by FACSCAN (Becton Dickinson, Mount View, Calif.).

Cytotoxic T Cell Activity

Cytotoxic T cell ("CTL") activity was determined by the release of lactate dehydrogenase ("LDH") (CytoTox, Promega, Madison, Wis.).

Mixed Leukocyte Reactions

The DCs, MC38/MUC1 and FC/MUC1 cells were exposed to ionizing radiation (30 Gy) and added to $1 \times 10^5$ syngeneic or allogeneic T cells in 96-well flat-bottomed cultured plates for 5 days. The T cells were prepared by passing spleen suspensions through nylon wool to deplete residual APCs and plated to 90 min in 100 mm tissue culture dishes. $^3$[H]-thymidine uptake in nonadherent cells was measured at 6 h after a pulse of 1 µCi/well (GBq/mmol; Du Pont-New England Nuclear, Wilmington, Del.). Each reaction was performed in triplicate.

In Vivo Depletion of Immune Cell Subsets

Mice were injected both intravenously and intraperitoneally every other day with mAb GK1.5 (anti-CD4), mAb 2.43 (anti-CD8) or rat IgG 4 days before the first of two immunizations with FC/MUC1 through 4 days before challenge with MC38/MUC1 cells. The splenocytes were harvested for flow cytometry and analysis of CTL activity.

Murine MC38 adenocarcinoma cells were fused to bone marrow-derived DCs. To demonstrate successful fusions, MC38 cells that stably express the DF3/MUC1 tumor-associated antigen were first used (Siddiqui et al., Proc. Natl. Acad. Sci. USA 75: 5132-5136, 1978). The fusion cells (FC/MUC1) expressed DF3/MUC1, as well as MHC class I and II, B7-1, B7-2 and ICAM-1.

Moreover, most of the fusion cells exhibited a DC morphology with veiled processes and dendrites. Fusions of MC38 cells with DCs (FC/MC38) resulted in similar patterns of cell-surface antigen expression with the exception of no detectable DF3/MUC1 antigen. Injection of MC38/MUC1 cells in mice resulted in the formation of subcutaneous tumors. Similar findings were obtained with MC38/MUC1 cells mixed with DCs or after mixing MC38 cells with DCs.

However, the finding that no tumors formed in mice injected with FC/MUC1 indicated that the fusion cells are not tumorigenic.

Dendritic cells are potent stimulators of primary MLRs; Steinman et al., Proc. Natl. Acad. Sci. U.S.A. 75: 5132-5136, 1978; van Voorhis et al., J. Exp. Med. 158: 174-191, 1983) and induce the proliferation of allogeneic CD8$^+$ T cells in vitro (Inaba et al., J. Exp. Med. 166: 182-194, 1987; Young et al., J. Exp. Med. 171: 1315-1332, 1990). To characterize in part the function of FC/MUC1 cells, their effect in primary allogeneic MLRs was compared with the effect of DC and MC38/MUC1 cells. The results demonstrate that, like DCs, FC/MUC1 cells exhibit a stimulatory function in allogeneic MLR. By contrast, MC38/MUC1 cells had little effect on T cell proliferation.

Mice were immunized twice with FC/MUC1 cells to assess in vivo function. Tumors developed in mice that had been immunized twice with $10^6$ irradiated MC38/MUC1 cells and subsequently challenged with MC38/MUC1 cells (Table 1). In contrast, after immunization with $2.5 \times 10^5$ FC/MUC1 cells, all animals remained tumor-free after challenge with MC38/MUC1 cells (Table 1). Control animals immunized with DCs alone or PBS and then challenged subcutaneously with $2.5 \times 10^5$ MC38 or MC38/MUC1 cells, however, exhibited tumor growth within 10-20 days.

Moreover, immunization with FC/MUC1 or FC/MC38 had no detectable effect on growth of unrelated syngeneic MB49 bladder carcinoma (Table 1). CTLs from mice immunized with FC/MUC1 cells induced lysis of MC38/MUC1, but not MB49 cells. By contrast, CTLs from mice immunized with DCs or PBS exhibited no detectable lysis of the MC38/MUC1 targets.

To further define the effector cells responsible for antitumor activity, mice were injected intraperitoneally with antibodies against $CD4^+$ or $CD8^+$ cells before and after immunization with FC/MUC1. Depletion of the respective population by 80-90% was confirmed by flow cytometric analysis of splenocytes. The finding that injection of anti-CD4 and anti-CD8 antibodies increases tumor incidence indicated that both $CD4^+$ and $CD8^+$ T cells contributed to antitumor activity. Moreover, depletion of $CD4^+$ and $CD8^+$ T cells was associated with reduced lysis of MC38/MUC1 cells in vitro.

TABLE 1

Potency and specificity of antitumor immunity induced with fusion cells

| Immunogen | Tumor Challenge | Animals with tumor |
|---|---|---|
| a, Irradiated MC38/MUC1 ($1 \times 10^6$) | MC38/MUC1 ($1 \times 10^6$) | 2/3 |
|  | MC38/MUC1 ($2 \times 10^6$) | 3/3 |
| b, FC/MUC1 ($2.5 \times 10^5$) | MC38/MUC1 ($1 \times 10^6$) | 0/10 |
|  | MC38/MUC1 ($2 \times 10^6$) | 0/10 |
|  | MB49 ($5 \times 10^6$) | 6/6 |
| c, FC/MC38 ($2.5 \times 10^5$) | MC38 ($1 \times 10^6$) | 0/6 |
|  | mb49 ($5 \times 10^5$) | 6/6 |

The numbers in parentheses represent cells used for immunization or tumor challenge To determine whether immunization with FC/MUC1 cells is effective for the prevention of disseminated disease, a model of MC38/MUC1 pulmonary metastases was used. Immunization with FC/MUC1 intravenously or subcutaneously completely protected against intravenous challenge with MC38/MUC1 cells. By contrast, all unimmunized mice similarly challenged with MC38/MUC1 cells developed over 250 pulmonary metastases.

In a treatment model, MC38/MUC1 pulmonary metastases were established 4 days before immunization with FC/MUC1. While control mice treated with vehicle developed over 250 metastases, nine out of ten mice treated with FC/MUC1 cells had no detectable metastases and one mouse had fewer than 10 nodules. Mice treated with FC/MC38 cells similarly bad no detectable MC38 pulmonary metastases. These findings indicated that FC/MUC1 immunization can be used for both the prevention and treatment of metastatic disease.

EXAMPLE II

Fusion of Human DCs and Myeloma Cells

Leukocytes in buffy coats (or leukopacks) obtained by leukophoresis were fractionated by centrifugation in Ficoll. The fraction containing (peripheral blood) mononuclear cells was incubated in a flask containing RPMI 1640 supplemented with 10% fetal calf serum ("FCS") for 30 mm at 37° C. Nonadherent cells, some of which were dendritic cells, were gently separated from the adherent cells, which were retained. To collect these DCs, the cells were incubated in RPMI 1640 supplemented with 20% FCS for 30 min to 1 hr, after which floating cells were removed and discarded. Both adherent cell samples were then incubated in RPMI 1640 supplemented with 20% FCS for 2-3 days to allow detachment of the loosely adherent cells (DCs). The loosely adherent cells were removed and retained. The remaining adherent cells, which still contained a relatively low proportion of loosely adherent DCs, were incubated with RPMI 1640 supplemented with 10% fetal calf serum overnight to allow detachment of the loosely adherent DCs. These were separated from the remaining adherent cells. The two samples of loosely adherent DCs were then pooled and cultured in a medium containing GM-CSF (1000 U/ml) and IL-4 (100 U/ml) at a density of $10^6$ cells/ml for 5-6 days. The resultant cells were the DCs used in fusion experiments.

DCs were also obtained from bone marrow stem cell cultures. In brief, stem cells were placed in a flask containing RPMI 1640 supplemented with 10% FCS. After 30 min of incubation at 37° C., nonadherent cells were washed away. Fresh RPMI 1640 supplemented with 10% FCS was added to the remaining, adherent cells. After overnight incubation, loosely adherent cells were collected and incubated in RPMI 1640/10% FCS medium containing GM-CSF (1000 U/ml) and IL-4 (100 U/ml) for 5-6 days. The resultant cells were DCs that were ready for use in fusion.

Cell fusion was carried out between DCs and human myeloma cells MY5 to produce fused cells DC/MY5. After fusion, the cells were placed in HAT selection for 10-14 days. IL-6 was also added to the culture at 20-50 ng/ml to promote survival of DC/MY5 cells. Procedures for fusion were essentially the same as described in Example 1, supra, except that the fused cells were separated from unfused myeloma cells based upon the higher degree of surface adherence exhibited by the fused cells.

As shown by flow cytometry, DC/MY5 cells retained the phenotypic characteristics of their parental cells: DC/MY5 were positively stained by mAbs for HLA-DR, CD38 (a myeloma cell-surface marker), DF3 (a tumor cell-surface marker), and CD83 (a DC cell-surface marker), B7-1, and B7-2. Mixed lymphocyte reaction (MLR) assays demonstrated that these fused cells were also potent stimulators of T cells. CD83 is an indicator of the maturity of a DC; more mature DCs express CD83, whereas less mature DCs express little or no CD83.

EXAMPLE III

Reversal of Tolerance to Human MUC1 Antigen in MUC1 Transgenic Mice Immunized with Fusion Cells MUC1 Transgenic Mice A C57BL/6 mouse strain transgenic for human MUC1 was established as described by Rowse et al. (Cancer Res. 58:315-321, 1998). 500 ng of tail DNA was amplified by PCR using MUC1 primers corresponding to nucleotides 745 to 765 and nucleotides 1086 to 1065, respectively, to confirm the presence of MUC1 sequences. The PCR product was detected by electrophoresis in a 1% agarose gel (Rowse et al., supra).

Cell Culture and Fusion

Murine (C57B1/6) MC38 and MB49 carcinoma cells were stably transfected with a MUC1 cDNA (Siddiqui et al., Proc. Natl. Acad. Sci. USA 85:2320-2323, 1988; Akagi et al., J. Immunotherapy 20: 38-47, 1997; Chen et al., J. Immunol. 159:351-359, 1997). Cells were maintained in DMEM supplemented with 10% heat-inactivated FCS, 2 mM L-glutamine, 100 U/ml penicillin, and 100 µg streptomycin. DC were obtained from bone marrow culture and fused to the carcinoma cells as described in Example I.

In Vitro T Cell Proliferation

Single cell preparations of spleen and lymph nodes were suspended in RPMI medium supplemented with 10% heat-inactivated FCS, 50 µm β-mercaptoethanol, 2 mM L-glutamine, 100 U/ml penicillin, and 100 µg/ml streptomycin. The cells were stimulated with 5 U/ml purified MUC1 antigen (Sekine et al., J. Immunol. 135:3610-3616, 1985). After 1, 3 and 5 days of culture, the cells were pulsed with 1 µCi [$^3$H] thymidine per well for 12 hours and collected on filters with a semi-automatic cell harvester. Radioactivity was quantitated by liquid scintillation.

Generation of CD8$^+$ T Cell Lines

Lymph node cells ("LNC") were suspended in complete RPMI medium containing 5 U/ml MUC1 antigen. Ten U/ml murine IL-2 was added after 5 days of culture. On days 10 and 15, the cells were restimulated with 5 U/ml MUC1 antigen and 1:5 irradiated (30 Gy) syngeneic spleen cells as APCs. T cell cultures were analyzed after removal of dead cells by Ficoll centrifugation and depletion of residual APCs by passage through nylon wool. The T cells were stained with FITC-conjugated antibodies against CD3e (145-2C11), CD4 (H129,19), CD8 (53-6.7), γδTcR (H57-597) and γδTcR (UC7-13D5) (PharMingen). After incubation on ice for 1 hour, the cells were washed, fixed and analyzed by FACSCAN (Becton-Dickinson).

Cytotoxicity Assays

In vitro cytotoxicity was measured in a standard $^{51}$Cr-release assay. Briefly, cells were labeled with $^{51}$Cr for 60 minutes at 37° C. and then washed to remove unincorporated isotope. The target cells (1×10$^4$) were added to wells of 96-well v-bottom plates and incubated with effector cells for 5 hours at 37° C. The supernatants were assayed for $^{51}$Cr in a gamma counter. Spontaneous release of $^{51}$Cr was assessed by incubation of target cells in the absence of effectors, while maximum or total release of $^{51}$Cr was determined by incubation of targets in 0.1% Triton-X-100. Percentage of specific $^{51}$Cr release was determined by the following equation: percent specific release=[(experimental-spontaneous)/(maximum-spontaneous)]×100.

Humoral Immune Responses

Microtiter plates were coated overnight at 4° C. with 5 U/well purified MUC1 antigen. The wells were washed with PBS containing 5% horse serum albumin and then incubated for 1 hour with four-fold dilutions of mouse sera. After washing and incubation with goat anti-mouse IgG conjugated to horseradish peroxidase (Amersham Life Sciences), antibody complexes were detected by development with o-phenylenediamine (Sigma) and measurement in an ELISA microplate autoreader EL310 at an OD of 490 nm.

Immunohistology

Freshly removed tissues were frozen in liquid nitrogen. Tissue sections of 5 µm in width were prepared in a cryostat and fixed in acetone for 10 minutes. The sections were then incubated with monoclonal antibody DF3 (anti MUC1), anti-CD4 (H129,19) or anti-CD8 (53-6.7) for 30 minutes at room temperature and then subjected to indirect immunoperoxidase staining using the VECTASTAIN ABC kit (Vector Laboratories).

As shown in Example 1, vaccines derived from fusions of DC and MC38/MUC1 carcinoma cells (FC/MUC1) induce potent anti-tumor immunity. To assess the effects of vaccinating MUC1 transgenic mice with FC/MUC1, the mice were immunized twice with 5×10$^5$ FC/MUC1 and, as controls, with 10$^6$ irradiated MC38/MUC1 cells or PBS. After challenge with 10$^6$ MC38 or MC38/MUC1 cells, all mice immunized with irradiated MC38/MUC1 cells or PBS developed tumors. By contrast, no tumor growth was observed in mice immunized with FC/MUC1. Immunization of the MUC1 transgenic mice with FC/MUC1 had no effect on growth of the unrelated MB49 bladder carcinoma (Chen et al., J. Immunol. 159:351-359, 1997). However, MB49 cells that express MUC1 (MB49/MUC1) failed to grow in the FC/MUC1-immunized mice.

To extend these results, CTLs from the FC/MUC1-immunized mice were assayed for lysis of target cells. CTLs from MUC1 transgenic mice immunized with irradiated MC38/MUC1 cells or PBS exhibited little if any reactivity against MC38/MUC1 cells. By contrast, CTLs from the mice immunized with FC/MUC1 induced lysis of MC38, MC38/MUC1 and MB49/MUC1, but not MB49, cells. As shown in wild-type mice (Example I, supra), immunization with FC/MUC1 induces immunity against MUC1 and other unknown antigens on MC38 cells. Thus, the demonstration that MB49/MUC1, and not MB49, cells are lysed by CTLs confirms that FC/MUC1 induces a MUC1-specific response. Further, immunization of the MUC1 transgenic mice with FC/MUC1, but not irradiated MC38/MUC1 or PBS, induced a specific antibody response against MUC1.

To determine whether T cells from the MUC1 transgenic mice can be primed to induce an anti-MUC1 response, draining LNC were isolated from mice immunized with irradiated MC38/MUC1 cells or FC/MUC1. The LNC were stimulated with MUC1 antigen in vitro. The results demonstrate that LNC from mice immunized with PBS or irradiated MC38/MUC1 cells fail to proliferate in the presence of MUC1 antigen. In contrast, LNC from mice immunized with FC/MUC1 responded to MUC1 with proliferation. To confirm the induction of CTLs against MUC1, draining LNC were isolated from MUC1 transgenic mice immunized with FC/MUC1 and cultured in the presence of MUC1 antigen and irradiated splenocytes. Cells were analyzed by FACSCAN at the beginning and at 10 to 15 days of culture. The results demonstrate the selection of a predominantly CD8$^+$ T cell population after incubation with MUC1 antigen. Unlike naive T cells from unimmunized MUC1 transgenic mice, these CD8$^+$ T cells exhibited specific CTL activity against MC38/

MUC1 and MB49/MUC1 targets. Collectively, the results suggest that immunization with FC/MUC1 reverses unresponsiveness to MUC1 in the MUC1 transgenic mice.

The finding that unresponsiveness to MUC1 can be reversed by immunization with FC/MUC1 suggested that this vaccine could be used to treat disseminated disease in a background of MUC1 expression by normal epithelia. In a treatment model, MC38/MUC1 pulmonary metastases were established by tail vein injection of MC38/MUC1 cells into the MUC1 transgenic mice. Whereas control mice treated with vehicle developed pulmonary metastases, mice immunized with FC/MUC1 on day 2 or 4 bad no detectable metastases. These findings indicate that FC/MUC1 immunizations can be used to treat metastatic disease in the MUC1 transgenic mice. Importantly, mice protected against MC38/MUC1 tumor exhibited persistent expression of MUC1 antigen in normal bronchial epithelium and other tissues that express the transgene (Rowse et al., Cancer Res. 58:315-321, 1998). Also, staining of MUC1-positive tissues with anti-CD4 and anti-CD8 antibodies did not show any T cell infiltration.

Reversal of unresponsiveness against a self-antigen in adult mice has potential importance in the field of antitumor immunotherapy. The present example demonstrates that immunization with the DC-tumor fusion cells induces an immune response that is sufficient to achieve rejection of established metastases. Notably, induction of an anti-MUC1 response, which confers anti-tumor immunity has little, if any, effect on normal secretory epithelia that express MUC1 at apical borders along ducts. These findings demonstrate that the induction of anti-MUC1 immunity represents an effective strategy for the treatment of MUC1-positive human tumors.

EXAMPLE IV

Activation of Tumor-specific CTL by Fusions of Human Dendritic Cells and Breast Carcinoma Cells Breast carcinoma Cell Culture Human MCF-7 breast carcinoma cells (ATCC, Rockville, MD) were grown in DMEM culture medium supplemented with 10% heat-inactivated FCS, 2 mL L-glutamine, 100 U/ml penicillin and 100 μg/ml streptomycin. Human breast carcinoma cells were obtained with Institutional Review Board approval from biopsies of primary tumors and metastatic lesions of skin, lungs and bone marrow. The cells were separated by incubation in $Ca^{2+}/Mg^{2+}$-free Hank's balanced salt solution containing 1 mg/ml collagenase, 0.1 mg/ml hyaluronidase and 1 mg/ml DNase. Breast tumor cells were also isolated from malignant pleural effusions by centrifugation and lysis of contaminating red blood cells. The breast tumor cells were maintained in RPMI 1640 medium supplemented with 10% heat-inactivated autologous-human serum, 2 mM L-glutamine, 100 U/ml penicillin, 100 μg/ml streptomycin and μg/ml insulin (Sigma).

Preparation of DC, Monocytes and T Cells

Peripheral blood mononuclear cells (PBMC) were isolated from patients with metastatic breast cancer by Ficoll-Hypaque density gradient centrifugation. The PBMC were suspended in RPMI 1640 culture medium supplemented with 10% human serum (Sigma) for 1 h. The non-adherent cells were removed and T cells were isolated by nylon wool separation. The adherent cells were cultured for 1 week in RPMI 1640 medium/10% human serum containing 1000 U/ml GM-CSF (Genzyme) and 500 U/ml IL-4 (Genzyme). The GM-CSF/IL-4 stimulated DC expressed MHC class I and II, B7-1, B7-2, ICAM, CD40 and variable amounts of CD83, but not CD14, CD19, cytokeratin or MUC1. Non-adherent and loosely adherent cells were harvested by repeated washes to generate the DC population. Firmly adherent monocytes were released from the plates with trypsin.

Cell Fusion

DCs were mixed with MCF-7 or primary breast cancer cells at a 10:1 ratio and incubated in serum-free RPMI 1640 medium containing 50% polyethyleneglycol (PEG) for 5 min. After slowly diluting with serum-free RPMI 1640 medium, the cells were washed, resuspended in RPMI 1640 medium supplemented with 10% autologous human serum and 500 U/ml GM-CSF, and incubated at 37° C. for 7-14 days.

Flow Cytometry

Cells were washed with PBS and incubated with murine antibodies directed against MUC1 (DF3) (Kufe et al., Hybridoma 3:223-232, 1984), MHC class I (W6/32), MHC class II (HLA-DR), B7-1 (CD80), B7-2 (CD86) or ICAM (CD54) (Pharmingen) for 1 h on ice. After washing with PBS, the cells were incubated with fluorescein-conjugated goat anti-mouse IgG for 30 min. on ice. The cells were washed again and then incubated with PE-conjugated anti-MHC class II or anti-B7-1 for 1 h at 4° C. Samples were then washed, fixed with 2% paraformaldehyde and subjected to bi-dimentional analysis by FACScan (Becton-Dickinson, Mountain View, Calif.).

Immunohistochemistry

Cytospin preparations of the cell populations were fixed in acetone for 10 min. The slides were incubated with MAb DF3 (anti-MUC1) or anti-cytokeratin antibody (AE1/AE3, Boehringer Mannheim, Ind.) for 30 min. at room temperature and then with biotinylated horse anti-mouse Ig for an additional 30 min. Reactivity was detected with ABC solution (Vector Laboratories, Burlingame, Calif.). The cells were then incubated with murine anti-MHC class II for 30 min and alkaline phosphatase labeled anti-mouse Ig for an additional 30 min. AP-ABC solution (Vector) was used to generate a blue counterstain.

Autologous T Cell Stimulation

DC, breast tumor cells and fusion cells were exposed to 30 Gy ionizing radiation and added to autologous T cells in 96-well, flat-bottom culture plates for 5d. [$^3$H]-thymidine uptake by T cells was measured at 12 h after a pulse of 1 μCi/well (New England Nuclear, Wilmington, Del.).

CTL Assays

PBMC were cocultured with autologous breast tumor or fusion cells for 10 days in the presence of 20 U/ml human interleukin-2 (HuIL-2). The stimulated T cells were harvested by nylon wool separation and used as effector cells in CTL assays with cell targets. Primary breast tumor cells, monocytes, MCF-7 cells, primary ovarian cancer cells (OVCA) and K562 cells were labeled with $^{51}$Cr for 60 min. at 37° C. After washing to remove unincorporated isotope, the targets ($2\times10^4$) were cocultured with effector cells for 5 h at 37° C. In the indicated experiment, labeled target cells were incubated with MAb Wb/32 (anti-MHC class I) for 30 min at 37° C. before addition to the effector cells. The supernatants were assayed for $^{51}$Cr release in a gamma counter. Spontaneous release of $^{51}$Cr was assessed by incubation of targets in the absence of effectors, while maximum or total release of $^{51}$Cr was determined by incubation of targets in 0.1% Triton X-100. Percentage of specific $^{51}$Cr release was determined by the following equation: percent specific release=[(experimental−spontaneous)/(maximum−spontaneous)]×100.

Phenotype of Human Breast Tumor/DC Fusions

To determine whether human DCs can be used in the generation of heterokaryons with tumor cells, DC from PBMC of patients with metastatic breast cancer were prepared. The DCs were initially fused to human MCF-7 breast carcinoma cells. Bi-dimensional flow cytometry demonstrated that MCF-7 cells express the MUC1 carcinoma-associated antigen and MHC class I, but not MHC class II-B7-1, B7-2 or ICAM. By contrast, DC expressed MHC class I, class II and costimulatory molecules, but not MUC I. Following fusion of MCF-7 cells and DC, the resulting heterokaryons coexpressed MUC1 and MHC class II. Similar patterns of coexpression of MUC1 with B7. 1, B7-2 and ICAM were observed on the fused cells. Since these findings indicated that it was possible to generate of breast cancer cell/DC fused cells, human breast cancer cells were isolated from patients with primary or metastatic tumors for the purpose of making DC fusion cells with them.

Immunostaining of short-term cultures demonstrated that the breast carcinoma cells expressed MUCI and cytokeratin (CT). The breast tumor cells had no detectable expression of MHC class II, costimulatory or adhesion molecules. The tumor cells were fused with autologous DC and, after culturing for 7 days, the resulting population was analyzed for the presence of fusion cells. Fusion of the tumor cells to autologous DC resulted in the generation of heterokaryons that expressed both MUCI and MHC class II or cytokeratin and MHC class II. Analysis by bi-dimensional flow cytometry confirmed that the breast tumor cells (BT) express MUCI, and not MHC class II, while the autologous DC expressed MHC class II, but not MUC1. By contrast, over 40% of the fused cells (DC/BT) expressed both MUC1 and MHC class II. Similar results obtained by histochemical staining and bi-dimensional flow cytometry further indicated the presence of fusion cells and not aggregates. As assessed by both methods, the efficiency of autologous fusions prepared from six separate breast cancer patients ranged from 30 to 50% of the tumor cell population.

Function of the Breast Tumor/DC Fusions

To determine whether the autologous fusion cells are effective in stimulating autologous T cells, the heterokaryons were cocultured with T cells isolated from nonadherent PBMC. As a control, the T cells were also cocultured with autologous tumor cells. While there was no evidence for a T cell response to autologous tumor, the fusion cells stimulated T cell proliferation and the formation of T cell/fusion cell clusters. To assess the specificity of this response, autologous T cells were incubated with DC, irradiated breast tumor cells, a mixture of unfused DC and breast tumor cells, or DC-breast tumor fusion cells. There was little if any T cell stimulation by autologous DC, tumor or a mixture of the two cell types. As additional controls, autologous T cells exhibited little if any response to PEG-treated DC or DC fused to monocytes, as compared to the response obtained with DC/tumor fusion cells. These findings demonstrate that fusion of breast tumor cells and DC results in stimulation of a specific T cell response.

Generation of CTL Against Human Breast Tumor

To assess the induction of tumor-specific CTL, T cells were stimulated for 10 days and then isolated for assaying lysis of autologous tumor cells. T cells incubated with autologous DC, irradiated breast tumor cells or an unfused mixture of both exhibited a low level of autologous breast tumor cell lysis. Significantly, T cells stimulated with the fusion cells were effective in inducing cytotoxicity of autologous tumor. Similar results were obtained with T cells from three breast cancer patients that had been stimulated with autologous DC/breast tumor cell fusions. Moreover, unstimulated T cells that had been cocultured with autologous breast tumor cells failed to mediate significant tumor cell killing.

To define the specificity of the CTL generated by incubation with fusion cells, we compared their ability to lyse autologous tumor and other cell types. Data was obtained with cells from two individual patients. Incubation of fusion-stimulated T cells with autologous breast tumor or monocytes demonstrated selectivity for lysis of the tumor cells. In addition, T cells stimulated with autologous fusion cells demonstrated significant lysis of autologous breast tumor cells, while lysis of MCF-7 cells, primary ovarian cancer cells and NK-sensitive K562 cells was similar to that obtained with autologous monocytes. The finding that preincubation of the targets with an antibody specific for MHC class 1 resulted in abrogation of autologous breast tumor cell lysis indicated that the killing was MHC class 1 restricted. By contrast, the antibody specific for MHC class I had little if any effect on lysis of the other cell types.

EXAMPLE V

Activation of Tumor-Specific CTL by Fusions of Human Dendritic Cells and Ovarian Carcinoma Cells Isolation of Peripheral Blood Mononuclear Cells (PBMC)

Mononuclear cells were isolated from the peripheral blood of patients with ovarian cancer and normal donors by Ficoll-Hypaque density gradient centrifugation. The PBMC were cultured in RPMI 1640 culture medium containing 1% autologous serum for 1 h. The non-adherent cells were removed and the T cells purified by nylon wool separation. The adherent cells were cultured for 1 week in RPMI 1640 culture medium containing 1% autologous serum, 1000 U/ml GM-CSF (Genzyme) and 500 U/ml IL-4 (Genzyme). DC were harvested from the non-adherent and loosely adherent cells. The firmly adherent monocytes were harvested after treatment with trypsin.

Preparation and Fusion of Ovarian Carcinoma Cells

Ovarian carcinoma (OVCA) cells obtained from primary tumors and malignant ascites were separated from other cells and non-cellular components in Hank's balanced salt solution ($Ca^{++}/Mg^{++}$ free) containing 1 mg/ml collagenase, 0.1 mg/ml hyaluronidase and 1 mg/ml DNase. The cells were cultured in RPMI 1640 culture medium supplemented with 10% heat-inactivated autologous human serum, 2 mM L-glutamine, 100 U/ml penicillin and 100 µg/ml streptomycin until fusion. Autologous or allogeneic DC were incubated with the OVCA cells for 5 min at a ratio of 10:1 in serum-free RPMI 1640 medium containing 50% polyethylene glycol (PEG). RPMI 1640 culture medium was then added slowly to dilute the PEG. After washing, the cells were resuspended in RPMI 1640 culture medium supplemented with 10% autologous serum and 500 U/ml GM-CSF for 7-14days.

Phenotype Analysis

Cells were incubated with mouse monoclonal antibodies (MAb) directed against human DF3/MUCI (MAb DF3) (Kufe et al, Hybridoma 3:223-232, 1984), human CA-125 (MAb OC-125) (Bast et al., N Engl. J Med 309(15):883-887, 1983), human MHC class I (W6/32), human MHC class II (RLA-DR), human B7-1 (CD80), human B7-2 (CD86), human ICAM (CD54; Pharmingen) and human CD83 (Pharmingen) for 1 h on ice. After washing with PBS, the cells were incubated with fluorescein-conjugated goat antibody specific for mouse IgG for 30 min. For dual expression analysis, cells were incubated with MAb OC-125, washed and then incubated with phycoerythrin-conjugated antibody specific for MHC class II, B7-2 or CD83 for 1 h at 4° C. Samples were washed, fixed in 2% paraformaldehyde and analyzed by FAC-Scan (Becton-Dickinson, Mountain View, Calif.).

Immunohistochemical Staining Cytospin cell preparations were fixed in acetone and incubated with MAb OC-125 for 30 min at room temperature. The slides were washed and incubated with biotinylated horse antibody specific for mouse IgG for an additional 30 min. Staining (red color) was achieved with ABC solution (Vector Laboratories, Burlingame, Calif.). The slides were then incubated with murine antibody specific for human MHC class II for 30 min followed by alkaline phosphatase-labeled anti-mouse IgO. AP-ABC solution (Vector Laboratories) was used to generate a blue counterstain.

T cell Proliferation Assays

Cells were exposed to 30 Gy ionizing radiation and added to T cells in 96-well flat-bottom plates for 5 d. Incorporation of [$^3$H]-thymidine by the T cells was measured after incubation in the presence of 1 µCi/well for 12 h.

Cytotoxicity Assays

T cells were stimulated with the indicated cell preparations for 1 week in the presence of 20 U/ml HuIL-2. The T cells were harvested by nylon wool separation and used as effector cells in CTL assays. Autologous OVCA cells, allogeneic OVCA cells, autologous monocytes, MCF-7 breast carcinoma cells and K562 cells were labeled with $^{51}$Cr for 60 min at 37° C. After washing, targets ($2\times10^4$) were cultured with the T cells for 5 h at 37° C. In certain experiments, the labeled target cells were incubated with MAb W6/32 (anti-MHC class I) for 30 min at 37° C. before addition of the effector cells. Supernatants were assayed for $^{51}$Cr release in a gamma counter. Spontaneous release of $^{51}$Cr was assessed by incubation of the targets in the absence of effectors. Maximum or total release of $^{51}$Cr was determined by incubation of the targets in 0.1% Triton X-100. Percentage of specific $^{51}$Cr release was determined by the following equation: percent specific release=[(experimental−spontaneous)/(maximum−spontaneous)]×100.

Characterization of Ovarian Carcinoma (OVCA) Cells Fused With Autologous and Allogeneic DC DC were generated from patients with metastatic ovarian cancer and from normal volunteers. Adherent cells were isolated from PBMC and cultured in the presence of GM-CSF and IL-4 for 1 week. The resulting population was subjected to FACS analysis. The DC displayed a characteristic phenotype with expression of MHC class I class II, costimulatory molecules, CD83 and ICAM, but not the DF3/MUC1 or CA-125 carcinoma-associated antigens. By contrast, OVCA 5 cells isolated from a patient with metastatic ovarian cancer expressed MUCI, CA-125, MHC class I and ICAM, but not MHC class II, B7-I, B7-2 or CD83. Similar findings were obtained with OVCA cells obtained from primary ovarian tumors and from malignant ascites. Fusion of the OVCA cells to autologous DC (OVCA/FC) resulted in the generation of heterokaryons (OVCA/FC) that express the CA-125 and MUCI antigens, MHC class II, B7-1, B7-2 and CD83.

Moreover, the pattern of antigen expression was similar when the OVCA cells were fused to allogeneic DC. Immunostaining confirmed that the DC expressed MHC class II and not CA-125. Conversely, the OVCA cells expressed CA-125 arid not MHC class II. Analysis of the fusion cells (OVCA/FC) demonstrated expression of both antigens.

Bi-dimensional flow cytometry was used to assess the efficiency of the fusions. In contrast to DC, the OVCA cells expressed CA-125, but not MHC class II, B7-2 or CD83. Analysis of OVCA cells fused with autologous DC demonstrated that 32.6% of the population expressed both CA-125 and MHC class II. Assessment of CA-125 and B7-2 expression demonstrated that 30% of the autologous OVCA/FC expressed both antigens. Moreover, 10.8% of the autologous OVCA/FC population expressed both CA-125 and CD83. Fusion of the OVCA cells and allogeneic DC also resulted in cells coexpressing CA-125 and MBC class II, B7-2 or CD83. These findings demonstrate the formation of heterokaryons by fusing OVCA cells to autologous or allogeneic DC.

Stimulation of Anti-tumor CTL by Autologous OVCA/FC

To assess the function of OVCA/FC, the fusion cells were cocultured with autologous PBMC. The experiment was performed with cells from three individual patients. As a control, the PBMC were also cultured with autologous OVCA cells. The fusion cells, but not the tumor cells, stimulated the formation of T cell clusters. After 10 days of stimulation, the T cells were isolated for assessment of cytolytic activity. Using autologous OVCA cells as targets, there was a low level of lysis when assaying T cells that had been incubated with autologous DC, autologous tumor, or a mixture of unfused DC and tumor. By contrast, T cells stimulated with the OVCA/FC were effective in inducing lysis of autologous tumor targets. Similar results were obtained with T cells from the three patients with ovarian cancer. As a control, T cells stimulated with OVCA cells fused to autologous monocytes (OVCA/MC) or DC fused to monocytes (DC/MC) had little effect on stimulation of anti-tumor CTL activity.

Generation of Anti-tumor CTL by OVCA Cells Fused to Allogeneic DC

To assess OVCA/FC function when the fusion is performed with allogeneic DC, autologous PBMC were stimulated with OVCA cells fused to autologous or allogeneic DC. As controls, the autologous PBMC were also stimulated with unfused DC or OVCA cells. Incubation of the T cells with allogeneic DC was associated with greater stimulation than that obtained with autologous DC. The results also demonstrate that T cell proliferation is stimulated to a greater extent by OVCA fused to allogeneic, as compared to autologous, DC. Similar findings were obtained with T cells obtained from the two patients. After stimulation for 10 days, the T cells were isolated and assessed for lysis of autologous tumor. Stimulation with unfused allogeneic or autologous DC had little if any effect on lytic function compared to that obtained with T cells stimulated in the presence of OVCA cells. By contrast, T cells stimulated with OVCA cells fused to allogeneic DC induced lysis of autologous tumor. Moreover, for both patients, T cells stimulated with OVCA cells fused to autologous or allogeneic DC exhibited induction of CTL activity. These findings demonstrate that the anti-tumor activity of autologous CTLs is stimulated by fusions of tumor cells to autologous or allogeneic DC.

Specificity of OVCA/FC-stimulated CTLs

To assess the specificity of CTL induced by fusion cells, T cells stimulated with OVCA cells fused to autologous DC were incubated with autologous tumor, autologous monocytes, MCF-7 breast carcinoma cells, allogeneic OVCA cells and NK-sensitive K562 cells. CTL assay cultures were carried out in the absence or presence of MAb specific for human MHC class I molecules. Incubation of the OVCA/FC stimulated T cells, with autologous tumor or monocytes demonstrated selective lysis of the tumor. In addition, there was no significant lysis of the MCF-7, allogeneic OVCA or K562 cells by these CTL. Preincubation of the targets with an anti-MHC class I antibody blocked lysis of the autologous OVCA cells and had little effect on that obtained for the other cell types in the absence of antibody. T cells stimulated with autologous OVCA cells fused to allogeneic DC also demonstrated selective lysis of the autologous tumor. Moreover, lysis of the autologous tumor was abrogated by preincubation of the targets with anti-MHC class I, thereby indicating that recognition of the tumor by the CTL was restricted by MHC class I molecules.

EXAMPLE VI

Assaying Antigen-Specificity

Preferably, the antigen-specific immune effector cells are CTLs. In other words, they actively lyse the cells expressing the specific antigen. Cytolytic activity of the cells can be measured in various ways, including, but not limited to, tritiated thymidine incorporation (indicative of DNA synthesis), and examination of the population for growth or proliferation, e.g., by identification of colonies. (See, e.g., WO 94/2 1287). In another embodiment, the tetrazolium salt MTT (3-(4,5-dimethyl-thazol-2-yl)-2,5-diphenyl tetrazolium bromide) may be added (Mossman (1983) J. Immunol Methods 65:55-63 and Niks and Otto (1990) J. Immunol Methods 130:140-151). Succinate dehydrogenase, found in mitochondria of viable cells, converts the MiT to formazan blue. Thus, concentrated blue color would indicate metabolically active cells. Similarly, protein synthesis may be shown by incorporation of $^{35}$S-methionine. In still another embodiment, cytotoxicity and cell killing assays, such as the classical chromium release assay, may be employed to evaluate epitope-specific CTL activation. Other suitable assays will be known to those of skill in the art.

As pointed out above, cytokine production or cytolytic $^{51}$Cr-release assays can be used (Coutic et al. (1992) Int. J. Cancer 50:289-291) to identify antigens. Alternatively, antigens can be identified using the method described in PCT WO 97/35035. The following experimental details provide a detailed description of this method.

Strategy I. The supernatant from each well is distributed to replica plates and 1-2×10$^3$ irradiated (1500 rads) foster APCs (expressing the proper MHC allele) are added to each well. Next, the cloned CTLs are added to a total of 10$^3$-10$^4$ cells representing equal amounts of 10-20 different clones of the same MHC restriction such that the total final volume per well is 200 µl and the plates are incubated in a humidified CO$_2$ incubator for 4 days at 37° C. Each well is then pulsed with 18.5 kBq of [$^3$H] dThd to measure CTL proliferation. 16 hours later, the radioactivity incorporated into the DNA of mitotically active CTLs is assayed by scintillation counting (Estaquier et at. (1994) Eur. J Immunol. 24:2789-2795). The magnitude of the proliferative response may serve as a preliminary screen for crossreacting epitopes. The greater the response the more likely it is that more than one CTL clone was stimulated. While all reactive peptides are of interest, the most efficacious vaccine candidates will be those that cross-react with CTLs derived from independent donors and which are restricted by the most common MHC alleles. Note that identification of epitopes containing the HLA B7-like supermotif would be of great value as vaccine candidates since it will bind to many HLA B alleles which are represented in over 40% of individuals from all major ethnic groups (Sidney et at. (1995) J. Immunol 154:247-259).

Strategy 2. Alternatively, the first step is to administer $^{51}$Cr-labeled T2 cells to the wells of the 2° daughter plates, followed by the addition of the CTLs. After 4 hours the released $^{51}$Cr is measured in the standard manner. When a positive well is identified, the 10 wells from the 1° daughter plate that correspond to that well are similarly assayed. At this point, the epitope search is narrowed down to the beads in a single well on one of the master plates.

Wells that register positive will be further analyzed as follows: the beads that correspond to the positive well are manually distributed (1 per well) to new plates and the remaining peptide is released from each. These plates are assayed as before, and in this way the reactive bead(s) are unambiguously isolated. The positive bead(s) can be rapidly and efficiently decoded since the molecular tags that encode the bead's synthesis history has remained on the bead (coupled with a non-photocleavable crosslinker). For example, analysis of the bead(s) by electron capture capillary gas chromatography immediately reveals the peptide sequence that was synthesized on that bead (Ohlmeyer et al., 1993, supra). Thus, the unambiguous identification of an epitope can be achieved in approximately ten days using the $^3$H-thymidine incorporation assay and in as few as two days if a $^{51}$Cr-release assay is used.

Application of the library beads to the surface of freshly poured top agar in a standard tissue culture plate, followed by release of a portion of the peptide, will result in a three dimensional concentration gradient of eluted peptide around each bead. Antigen presenting cells could be present in the top agar or applied to the surface after peptide release. Next, the CTL(s) of interest are plated over the top agar/peptide/APCs, followed by incubation at 37° C. for 4-12 hours. Reactive beads may be detected by the formation of plaques, where the size of the plaque indicates the magnitude of the response. Positive beads can then be taken from the plate, washed, and sequenced. This assay requires very little manual manipulation of the beads and the entire library can be screened simultaneously (in one step) in as little as four hours. Furthermore, the beads can be recovered, washed in 6M guanidiium, and reused.

The described method for the identification of CD8+ MHC Class I restricted CTL epitopes can be applied to the identification of CD4+ MHC Class II restricted helper T cell (Th) epitopes. In this case, MHC Class II allele-specific libraries are synthesized such that haplotype-specific 20 anchor residues are represented at the appropriate positions. MHC Class II agretopic motifs have been identified for the common alleles (Rarnmensee (1995) Curr. Opin. Immunol 7:85-96; Altuvia et al. (1994) Mol Immunol 24:375-379, Reay et al. (1994) J. Immunol 152:3946-3957; Verreck et al. (1994) Eur. J. Immunol 24:375-379; Sinigaglia and Hammer (1994) Curr. Opin. Immunol 6:52-56; Rotzschke and Falk (1994) Curr. Opin. Immunol 6:45-51). The overall length of the peptides will be 12-20 amino acid residues, and previously described methods may be employed to limit library complexity. The screening process is identical to that described for MHC Class I-associated epitopes except that B lymphoblastoid cell lines (B-LCL) are used for antigen presentation rather than T2 cells. In a preferred aspect, previously characterized B-LCLs that are defective in antigen processing (Mellins et al. (1991). Exp. Med 174:1607-1615); thus allowing specific presentation of exogenously added antigen, are employed. The libraries are screened for reactivity with isolated CD4+ MHC Class II allele-specific Th cells. Reactivity may be measured by $^3$H-thymidine incorporation according to the method of Mellins et al. supra., or by any of the methods previously described for MHC Class I-associated epitope screening.

The above methods utilize foster antigen presenting cells. The human cell line 174xCEM.T2, referred to as T2, contains a mutation in its antigen processing pathway that restricts the association of endogenous peptides with cell surface MHC class I molecules (Zweerink et al. (1993) 1. Immunol 150: 1763-1771). This is due to a large homozygous deletion in the MHC class II region encompassing the genes TAP 1, TAP2, LMP1, and LMP2 which are required for antigen presentation to MHC class I-restricted CD8+ CTLs. In effect, only "empty" MHC class I molecules are presented on the surface of these cells. Exogenous peptide added to the culture medium binds to these MHC molecules provided that the peptide contains the allele-specific binding motif. These T2 cells are referred to as "foster" APCs.

EXAMPLE VIII

Immunotherapy

The rationale for immunotherapy is predicated on the observation that non-professional APCs (e.g., tumor cells, virus-infected cells, etc.) toward which active specific immune responses are sought, can serve as lytic targets for educated immune effector cells even though they are inefficient at educating immune effector cells in vivo and in vitro. The molecular basis of this inefficiency is due, at least in part, to the lack of poorly defined costimulatory signals required for T cell priming such as those found in professional APCs (e.g., dendritic cells). Gong et al (PNAS (1998) 95: 6279 and Nat. Med (1997) 3(5):558), have demonstrated that fusion of murine DCs to syngeneic carcinoma cells results in a hybrid cell that substantially retains the immune effector cell priming capacity of the DCs while endogenously expressing and presenting a spectrum of carcinoma-associated tumor antigens. Given the high degree of morphologic, phenotypic and functional homology that exists between murine and human DCs, the present invention extends the utility of DC/tumor fusions to human DCs fused to human tumor cells for the purpose of educating effector T cells directed against tumor antigens in vitro. There are no significant changes to the Gong et al. fusion protocol that are anticipated in order to adapt the process to human DC fusions.

Immunizations. MUC1.Tg mice (transgenic for MUCI, Rowse et al., (1988) Cancer Res. 58:3 15) were injected subcutaneously on day 0 and day 7 with $1 \times 10^6$ MC-38IMUC1 cells exposed to 100 Gy ionizing radiation. FC/MUC1 fusion cells ($5 \times 10^5$) were administered subcutaneously on day 0 and day 7 for tumor prevention studies.

FACS analysis of surface marker expression comparing DCs, MC38/MUC1 tumor cells, and the MC-38/MUC1-DC fusion cells (FC/MUC1) was performed. It is apparent that the fusion cells are equipped with all of the DC markers including MHC I, MHC II, B7-1, B7-2, and ICAM-1 whereas, with the exception of MHC I, none of the markers are upregulated in the parental MC-38/MUC1 cells. This is consistent with the DC-like "veiled" morphology of the fusion cells. In addition, the fusion cells also express the tumor antigen MUCI at the same high level as the parental tumor cells whereas MUC1 expression is not detected in the parental DCs. Thus, the gene expression pattern observed in fusion cells is a composite of the expression patterns observed in the individual parental cell populations and importantly, the expression levels of the DC markers believed to confer potent APC functionality are maintained.

It was also demonstrated that vaccination of MUC1 transgenic mice (MUC1.Tg) with the fusion cells (FC/MUC1 and FC/MC-38) conferred potent and specific protection against tumor rechallenge whereas mice vaccinated with irradiated MC-38/MUC1 cells developed tumors upon rechallenge (Table 1). This is a remarkable demonstration of the immune stimulating potency of the fusion cells since these animals were tolerized from birth with the MUC1 antigen. This reversal of tolerance and concomitant tumor protection was shown to be specific since the fusion cells provided no protection against MB49 cells.

Furthermore, CD8+ lymph node cells from FC/MUC1 vaccinated mice were capable of lysing MC-38 cells, MC-38/MUC1 cells and FC/MUC1 cells, but not the MUC1-negative syngeneic tumor line MB49. Lymph node cells from naive mice were unable to lyse MC-38, MC-38IMUCI, or MB49 cells. Taken together, these data imply that the tumor protection afforded by the fusion cells is mediated by the education of immune effector cells and that these effector cells can lyse the parental tumor cells. It is of interest to note that vaccination with the parental tumor cells does not result in a potent CD8+ anti-tumor response, but when the immune response is provoked with the fusion cells, the MC-38 cells are efficient targets and are rejected.

These studies demonstrate the feasibility of the present invention. That is, DC fusions can educate immune effector cells by presenting the antigens expressed by the tumor cells in the context of a professional APC environment. It is inferred from this data that: (1) the general methods of fusing murine DCs to murine tumor cells will apply to the fusion of human DCs to human tumor cells, and (2) human DC fusion cells will be potent agents at eliciting anti-tumor immune effector cells in vitro, the products of which can be used directly as therapeutics (e.g., adoptive T cell transfer) or to further characterize the nature of the tumor rejection antigens.

We claim:

1. A method of producing a substantially pure cytotoxic population of educated, antigen-specific immune effector cells, wherein the immune effector cells are T-lymphocytes and wherein said population comprises $CD4^+$ immune effector cells and cytotoxic $CD8^+$ immune effector cells, the method comprising contacting immune effector cells with hybrid cells, wherein said hybrid cells are generated by fusion between at least one mammalian dendritic cell and at least one mammalian tumor or cancer cell that expresses a cell-surface antigen, wherein the dendritic cell and the tumor or cancer cell are from the same mammalian species, wherein the dendritic cell can process and present antigens, and wherein at least half of the hybrid cells express, in an amount effective to stimulate an immune system, (a) a MHC class II molecule, (b) B7, and (c) the cell-surface antigen, wherein the contacting causes differentiation of naïve immune effector cells in the population of T lymphocytes to educated immune effector cells, thereby producing the substantially pure cytotoxic population of educated, antigen-specific immune effector cells.

2. The method of claim 1, wherein the antigen-specific immune effector cells are genetically modified cells.

3. The method of claim 1, wherein the hybrid cells are genetically modified cells.

4. The method of claim 2, wherein the genetic modification comprises introduction of a polynucleotide.

5. The method of claim 4, wherein the polynucleotide encodes a peptide, a ribozyme or an antisense sequence.

6. A method of producing a substantially pure cytotoxic population of educated, antigen-specific immune effector cells, wherein the immune effector cells are T lymphocytes, and wherein said population comprises $CD4^+$ immune effector cells and cytotoxic $CD8^+$ immune effector cells, the method comprising culturing immune effector cells with hybrid cells, wherein said hybrid cells are generated by fusion between at least one mammalian dendritic cell and at least one mammalian tumor or cancer cell that expresses a cell-surface antigen, wherein the dendritic cell and the tumor or cancer cell are from the same mammalian species, wherein the dendritic cell can process and present antigens, and wherein at least half of the hybrid cells express, in an amount effective to stimulate an immune system, (a) a MHC class II molecule, (b)

B7, and (c) the cell-surface antigen, wherein the culturing causes differentiation of naïve immune effector cells in the population of T lymphocytes to educated immune effector cells, thereby producing the substantially pure cytotoxic population of educated, antigen-specific immune effector cells.

7. The method of claim 6, wherein the antigen-specific immune effector cells are genetically modified cells.

8. The method of claim 6, wherein the hybrid cells are genetically modified cells.

9. The method of claim 7, wherein the genetic modification comprises introduction of a polynucleotide.

10. The method of claim 9, wherein the polynucleotide encodes a peptide, a ribozyme or an antisense sequence.

11. The method of claim 6, wherein the immune effector cells are naïve prior to culturing with the hybrid cells.

12. The method of claim 6, wherein the immune effector cells are educated prior to culturing with the hybrid cells.

13. The method of claim 6, wherein the immune effector cells are cultured with the hybrid cells in the presence of a cytokine.

14. The method of claim 13, wherein the cytokine is IL-2.

15. The method of claim 1, wherein the immune effector cells are contacted with the hybrid cells in the presence of a cytokine.

16. The method of claim 15, wherein the cytokine is IL-2.

* * * * *